US012235697B2

(12) United States Patent
Jayme et al.

(10) Patent No.: US 12,235,697 B2
(45) Date of Patent: Feb. 25, 2025

(54) BACKPLANE CONNECTOR ATTACHMENT MECHANISM FOR MODULAR ENERGY SYSTEM

(71) Applicant: Cilag GmbH International, Zug (CH)

(72) Inventors: Madeleine C. Jayme, Cincinnati, OH (US); Ryan M. Asher, Cincinnati, OH (US); William B. Weisenburgh, II, Maineville, OH (US); Joshua M. Henderson, Montgomery, OH (US)

(73) Assignee: Cilag GmbH International, Zug (CH)

( * ) Notice: Subject to any disclaimer, the term of this patent is extended or adjusted under 35 U.S.C. 154(b) by 257 days.

(21) Appl. No.: 17/217,402

(22) Filed: Mar. 30, 2021

(65) Prior Publication Data

US 2022/0317750 A1  Oct. 6, 2022

(51) Int. Cl.
*G06F 1/26* (2006.01)
*H02J 1/10* (2006.01)
*H02J 3/00* (2006.01)
*A61B 34/00* (2016.01)
*A61B 90/00* (2016.01)
*H05K 7/02* (2006.01)
*H05K 7/14* (2006.01)

(52) U.S. Cl.
CPC ............. *G06F 1/266* (2013.01); *H02J 1/10* (2013.01); *H02J 3/007* (2020.01); *A61B 34/25* (2016.02); *A61B 90/37* (2016.02); *A61B 2090/372* (2016.02); *H02J 2310/23* (2020.01); *H05K 7/023* (2013.01); *H05K 7/1422* (2013.01)

(58) Field of Classification Search
CPC ....... H05K 7/023; H05K 7/1422; G06F 1/266
See application file for complete search history.

(56) References Cited

U.S. PATENT DOCUMENTS 4,171,700 A 10/1979 Farin
4,378,801 A 4/1983 Oosten
(Continued)

FOREIGN PATENT DOCUMENTS

EP 0408160 A1 1/1991
EP 0473987 A1 3/1992
(Continued)

OTHER PUBLICATIONS

Sorrells, P., "Application Note AN680. Passive RFID Basics," retrieved from http://ww1.microchip.com/downloads/en/AppNotes/00680b.pdf on Feb. 26/2020, Dec. 31, 1998, pp. 1-7.
(Continued)

*Primary Examiner* — Mukundbhai G Patel

(57) ABSTRACT

Disclosed is a modular energy system that comprises a first module, comprising a first panel, and a first connector attached to the first panel. A portion of the first connector extends past a first edge of the first panel. The modular energy system further comprises a second module, comprising a second panel, and a second connector attached to the second panel. The second connector is aligned with a second edge of the second panel, and the second connector defines a cavity. The second module is coupled to the first module, wherein the portion of the first connector that extends past the first edge of the first panel is positioned within the cavity defined by the second connector.

15 Claims, 44 Drawing Sheets

(56) References Cited

U.S. PATENT DOCUMENTS

| | | |
|---|---|---|
| 4,640,279 A | 2/1987 | Beard |
| 4,849,752 A | 7/1989 | Bryant |
| D303,787 S | 10/1989 | Messenger et al. |
| 5,041,110 A | 8/1991 | Fleenor |
| D327,061 S | 6/1992 | Soren et al. |
| 5,189,277 A | 2/1993 | Boisvert et al. |
| 5,204,669 A | 4/1993 | Dorfe et al. |
| 5,318,563 A | 6/1994 | Malis et al. |
| 5,325,270 A | 6/1994 | Wenger et al. |
| 5,383,880 A | 1/1995 | Hooven |
| 5,395,033 A | 3/1995 | Byrne et al. |
| 5,425,375 A | 6/1995 | Chin et al. |
| 5,613,158 A | 3/1997 | Savage |
| D379,346 S | 5/1997 | Mieki |
| 5,667,517 A | 9/1997 | Hooven |
| 5,690,504 A | 11/1997 | Scanlan et al. |
| 5,693,042 A | 12/1997 | Boiarski et al. |
| 5,724,468 A | 3/1998 | Leone et al. |
| 5,788,688 A | 8/1998 | Bauer et al. |
| 5,817,119 A | 10/1998 | Klieman et al. |
| 5,849,020 A | 12/1998 | Long et al. |
| 5,865,361 A | 2/1999 | Milliman et al. |
| 5,872,481 A | 2/1999 | Sevic et al. |
| 5,901,150 A | 5/1999 | Jhuboo et al. |
| 5,910,139 A | 6/1999 | Cochran et al. |
| 5,941,846 A | 8/1999 | Duffy et al. |
| 6,019,745 A | 2/2000 | Gray |
| 6,049,467 A | 4/2000 | Tamarkin et al. |
| 6,055,062 A | 4/2000 | Dina et al. |
| 6,055,458 A | 4/2000 | Cochran et al. |
| 6,068,627 A | 5/2000 | Orszulak et al. |
| D431,811 S | 10/2000 | Nishio et al. |
| 6,172,875 B1 * | 1/2001 | Suzuki ............... H05K 7/1465 361/752 |
| 6,179,136 B1 | 1/2001 | Kluge et al. |
| 6,269,411 B1 | 7/2001 | Reasoner |
| 6,273,750 B1 * | 8/2001 | Malkowski, Jr. .... H01R 9/2491 439/620.01 |
| 6,288,606 B1 | 9/2001 | Ekman et al. |
| H2037 H | 7/2002 | Yates et al. |
| 6,416,471 B1 | 7/2002 | Kumar et al. |
| 6,546,270 B1 | 4/2003 | Goldin et al. |
| 6,584,358 B2 | 6/2003 | Carter et al. |
| 6,592,387 B2 * | 7/2003 | Komenda .......... H01R 13/6315 439/247 |
| 6,611,793 B1 | 8/2003 | Burnside et al. |
| 6,731,514 B2 | 5/2004 | Evans |
| 6,760,218 B2 | 7/2004 | Fan |
| 6,839,238 B2 | 1/2005 | Derr et al. |
| 6,843,657 B2 | 1/2005 | Driscoll et al. |
| 6,888,848 B2 | 5/2005 | Beshai et al. |
| 6,913,471 B2 | 7/2005 | Smith |
| 7,009,511 B2 | 3/2006 | Mazar et al. |
| 7,044,949 B2 | 5/2006 | Orszulak et al. |
| 7,074,205 B1 | 7/2006 | Duffy et al. |
| 7,134,994 B2 | 11/2006 | Alpert et al. |
| 7,171,784 B2 | 2/2007 | Eenigenburg |
| 7,217,269 B2 | 5/2007 | El-Galley et al. |
| 7,252,664 B2 | 8/2007 | Nasab et al. |
| 7,268,684 B2 | 9/2007 | Tethrake et al. |
| 7,331,699 B2 | 2/2008 | Gawalkiewicz et al. |
| 7,344,532 B2 | 3/2008 | Goble et al. |
| 7,353,068 B2 | 4/2008 | Tanaka et al. |
| D575,792 S | 8/2008 | Benson |
| 7,408,439 B2 | 8/2008 | Wang et al. |
| 7,443,296 B2 | 10/2008 | Mezhinsky et al. |
| D579,876 S | 11/2008 | Novotney et al. |
| D583,328 S | 12/2008 | Chiang |
| 7,496,418 B2 | 2/2009 | Kim et al. |
| D589,447 S | 3/2009 | Sasada et al. |
| 7,500,747 B2 | 3/2009 | Howell et al. |
| 7,518,502 B2 | 4/2009 | Austin et al. |
| 7,563,259 B2 | 7/2009 | Takahashi |
| 7,601,149 B2 | 10/2009 | DiCarlo et al. |
| 7,637,907 B2 | 12/2009 | Blaha |
| 7,656,671 B2 | 2/2010 | Liu et al. |
| 7,695,485 B2 | 4/2010 | Whitman et al. |
| 7,722,603 B2 | 5/2010 | McPherson |
| 7,757,028 B2 | 7/2010 | Druke et al. |
| 7,794,457 B2 | 9/2010 | McPherson et al. |
| D631,252 S | 1/2011 | Leslie |
| 7,932,826 B2 | 4/2011 | Fritchie et al. |
| 7,945,065 B2 | 5/2011 | Menzl et al. |
| 7,945,342 B2 | 5/2011 | Tsai et al. |
| 7,982,776 B2 | 7/2011 | Dunki-Jacobs et al. |
| 7,995,045 B2 | 8/2011 | Dunki-Jacobs |
| 8,019,094 B2 | 9/2011 | Hsieh et al. |
| 8,057,492 B2 | 11/2011 | Ortiz et al. |
| D655,678 S | 3/2012 | Kobayashi et al. |
| D657,368 S | 4/2012 | Magee et al. |
| 8,187,263 B2 | 5/2012 | Behnke et al. |
| 8,218,279 B2 | 7/2012 | Liao et al. |
| 8,231,614 B2 | 7/2012 | Dunning et al. |
| 8,239,066 B2 | 8/2012 | Jennings et al. |
| D667,838 S | 9/2012 | Magee et al. |
| D675,164 S | 1/2013 | Kobayashi et al. |
| D676,392 S | 2/2013 | Gassauer |
| D678,196 S | 3/2013 | Miyauchi et al. |
| D678,304 S | 3/2013 | Yakoub et al. |
| 8,423,182 B2 | 4/2013 | Robinson et al. |
| D687,146 S | 7/2013 | Juzkiw et al. |
| 8,504,136 B1 | 8/2013 | Sun et al. |
| 8,540,709 B2 | 9/2013 | Allen |
| 8,551,088 B2 | 10/2013 | Falkenstein et al. |
| 8,567,393 B2 | 10/2013 | Hickle et al. |
| D704,839 S | 5/2014 | Juzkiw et al. |
| 8,795,001 B1 | 8/2014 | Lam et al. |
| 8,819,581 B2 | 8/2014 | Nakamura et al. |
| 8,840,609 B2 | 9/2014 | Stuebe |
| D716,333 S | 10/2014 | Chotin et al. |
| 8,911,437 B2 | 12/2014 | Horlle et al. |
| 8,917,513 B1 | 12/2014 | Hazzard |
| 8,920,186 B2 | 12/2014 | Shishikura |
| 8,923,012 B2 | 12/2014 | Kaufman et al. |
| 8,961,441 B2 | 2/2015 | Cioanta et al. |
| 8,968,296 B2 | 3/2015 | McPherson |
| 8,986,288 B2 | 3/2015 | Konishi |
| 9,017,326 B2 | 4/2015 | DiNardo et al. |
| D729,267 S | 5/2015 | Yoo et al. |
| 9,055,870 B2 | 6/2015 | Meador et al. |
| 9,065,394 B2 | 6/2015 | Lim et al. |
| 9,129,054 B2 | 9/2015 | Nawana et al. |
| 9,160,853 B1 | 10/2015 | Daddi et al. |
| 9,168,054 B2 | 10/2015 | Turner et al. |
| 9,168,091 B2 | 10/2015 | Janssen et al. |
| 9,198,711 B2 | 12/2015 | Joseph |
| 9,226,766 B2 | 1/2016 | Aldridge et al. |
| 9,226,791 B2 | 1/2016 | McCarthy et al. |
| 9,237,921 B2 | 1/2016 | Messerly et al. |
| 9,265,429 B2 | 2/2016 | St. Pierre et al. |
| 9,277,961 B2 | 3/2016 | Panescu et al. |
| 9,277,969 B2 | 3/2016 | Brannan et al. |
| 9,281,615 B1 | 3/2016 | Plaza et al. |
| 9,320,646 B2 | 4/2016 | Todd et al. |
| 9,345,481 B2 | 5/2016 | Hall et al. |
| 9,345,900 B2 | 5/2016 | Wu et al. |
| 9,351,653 B1 | 5/2016 | Harrison |
| 9,370,361 B2 | 6/2016 | Viola et al. |
| 9,391,670 B2 | 7/2016 | Brukalo et al. |
| 9,427,255 B2 | 8/2016 | Griffith et al. |
| 9,430,438 B2 | 8/2016 | Biskup |
| 9,463,646 B2 | 10/2016 | Payne et al. |
| 9,474,565 B2 | 10/2016 | Shikhman et al. |
| D772,252 S | 11/2016 | Myers et al. |
| 9,486,271 B2 | 11/2016 | Dunning |
| 9,491,895 B2 | 11/2016 | Steeves et al. |
| 9,532,827 B2 | 1/2017 | Morgan et al. |
| 9,589,720 B2 | 3/2017 | Akahane |
| 9,600,031 B2 | 3/2017 | Kaneko et al. |
| 9,603,277 B2 | 3/2017 | Morgan et al. |
| D783,675 S | 4/2017 | Yagisawa et al. |
| D784,270 S | 4/2017 | Bhattacharya |
| 9,666,974 B2 | 5/2017 | Bopp |
| 9,713,503 B2 | 7/2017 | Goldschmidt |

(56) References Cited

U.S. PATENT DOCUMENTS

| | | |
|---|---|---|
| 9,715,271 B2 | 7/2017 | Kaestner |
| 9,750,563 B2 | 9/2017 | Shikhman et al. |
| 9,770,103 B2 | 9/2017 | Cochran et al. |
| 9,773,093 B2 | 9/2017 | Bernini et al. |
| 9,782,214 B2 | 10/2017 | Houser et al. |
| 9,788,907 B1 | 10/2017 | Alvi et al. |
| 9,804,977 B2 | 10/2017 | Ghosh et al. |
| D806,721 S | 1/2018 | Fischer |
| 9,867,670 B2 | 1/2018 | Brannan et al. |
| 9,892,483 B2 | 2/2018 | Lee et al. |
| 9,892,564 B1 | 2/2018 | Cvetko et al. |
| 9,907,196 B2 | 2/2018 | Susini et al. |
| 9,971,395 B2 | 4/2018 | Chenault et al. |
| 9,974,595 B2 | 5/2018 | Anderson et al. |
| 9,987,068 B2 | 6/2018 | Anderson et al. |
| 9,987,072 B2 | 6/2018 | McPherson |
| 10,028,402 B1 | 7/2018 | Walker |
| 10,039,589 B2 | 8/2018 | Virshek et al. |
| D832,211 S | 10/2018 | Ladd et al. |
| 10,098,527 B2 | 10/2018 | Weisenburgh, II et al. |
| 10,105,470 B2 | 10/2018 | Reasoner et al. |
| 10,109,835 B2 | 10/2018 | Yang |
| D834,541 S | 11/2018 | You et al. |
| 10,117,702 B2 | 11/2018 | Danziger et al. |
| 10,128,612 B1 | 11/2018 | Casto |
| 10,136,954 B2 | 11/2018 | Johnson et al. |
| 10,137,245 B2 | 11/2018 | Melker et al. |
| 10,147,148 B2 | 12/2018 | Wu et al. |
| 10,166,061 B2 | 1/2019 | Berry et al. |
| 10,170,205 B2 | 1/2019 | Curd et al. |
| 10,201,365 B2 | 2/2019 | Boudreaux et al. |
| 10,219,858 B2 | 3/2019 | Danek et al. |
| 10,339,496 B2 | 7/2019 | Matson et al. |
| 10,357,184 B2 | 7/2019 | Crawford et al. |
| 10,386,990 B2 | 8/2019 | Shikhman et al. |
| 10,441,345 B2 | 10/2019 | Aldridge et al. |
| 10,449,004 B2 | 10/2019 | Ferro et al. |
| 10,475,244 B2 | 11/2019 | Cvetko et al. |
| 10,493,287 B2 | 12/2019 | Yoder et al. |
| 10,499,794 B2 | 12/2019 | Gilreath et al. |
| 10,499,847 B2 | 12/2019 | Latimer et al. |
| 10,499,996 B2 | 12/2019 | de Almeida Barreto |
| 10,523,122 B2 | 12/2019 | Han et al. |
| 10,531,579 B2 | 1/2020 | Hsiao et al. |
| D876,466 S | 2/2020 | Kobayashi et al. |
| 10,561,753 B2 | 2/2020 | Thompson et al. |
| 10,602,007 B2 | 3/2020 | Takano |
| 10,624,667 B2 | 4/2020 | Faller et al. |
| 10,624,691 B2 | 4/2020 | Wiener et al. |
| 10,675,027 B2 | 6/2020 | Aldridge et al. |
| 10,675,100 B2 | 6/2020 | Frushour |
| 10,687,884 B2 | 6/2020 | Wiener et al. |
| 10,729,502 B1 | 8/2020 | Wolf et al. |
| 10,743,872 B2 | 8/2020 | Leimbach et al. |
| 10,758,309 B1 | 9/2020 | Chow et al. |
| 10,758,310 B2 | 9/2020 | Shelton, IV et al. |
| 10,772,673 B2 | 9/2020 | Allen, IV et al. |
| 10,838,386 B1* | 11/2020 | Wrobel ............... G06F 11/1616 |
| 10,878,966 B2 | 12/2020 | Wolf et al. |
| 10,881,399 B2 | 1/2021 | Shelton, IV et al. |
| 10,898,256 B2 | 1/2021 | Yates et al. |
| 10,898,279 B2 | 1/2021 | Yang |
| 10,925,598 B2 | 2/2021 | Scheib et al. |
| 10,932,705 B2 | 3/2021 | Muhsin et al. |
| 10,932,772 B2 | 3/2021 | Shelton, IV et al. |
| 10,950,982 B2 | 3/2021 | Regnier et al. |
| 10,987,176 B2 | 4/2021 | Poltaretskyi et al. |
| 10,989,724 B1 | 4/2021 | Holmes et al. |
| 11,000,270 B2 | 5/2021 | Scheib et al. |
| D924,139 S | 7/2021 | Jayme |
| 11,056,244 B2 | 7/2021 | Shelton, IV et al. |
| 11,065,079 B2 | 7/2021 | Wolf et al. |
| 11,071,595 B2 | 7/2021 | Johnson et al. |
| D928,725 S | 8/2021 | Oberkircher et al. |
| D928,726 S | 8/2021 | Asher et al. |
| 11,077,312 B2 | 8/2021 | Sturman et al. |
| 11,083,489 B2 | 8/2021 | Fujii et al. |
| 11,116,587 B2 | 9/2021 | Wolf et al. |
| 11,129,669 B2 | 9/2021 | Stulen et al. |
| 11,185,379 B2 | 11/2021 | Shuma et al. |
| D939,545 S | 12/2021 | Oberkircher et al. |
| 11,259,793 B2 | 3/2022 | Scheib et al. |
| 11,259,875 B2 | 3/2022 | Boutin et al. |
| 11,272,839 B2 | 3/2022 | Al-Ali et al. |
| 11,272,975 B2 | 3/2022 | Tonn et al. |
| 11,284,963 B2 | 3/2022 | Shelton, IV et al. |
| 11,296,540 B2 | 4/2022 | Kirleis et al. |
| 11,304,763 B2 | 4/2022 | Shelton, IV et al. |
| 11,314,846 B1 | 4/2022 | Colin et al. |
| 11,369,366 B2 | 6/2022 | Scheib et al. |
| 11,382,699 B2 | 7/2022 | Wassall et al. |
| 11,382,700 B2 | 7/2022 | Calloway et al. |
| 11,419,604 B2 | 8/2022 | Scheib et al. |
| 11,424,027 B2 | 8/2022 | Shelton, IV |
| 11,432,877 B2 | 9/2022 | Nash et al. |
| 11,464,581 B2 | 10/2022 | Calloway |
| 11,478,820 B2 | 10/2022 | Bales, Jr. et al. |
| 11,504,192 B2 | 11/2022 | Shelton, IV et al. |
| 11,510,750 B2 | 11/2022 | Dulin et al. |
| 11,559,307 B2 | 1/2023 | Shelton, IV et al. |
| 11,564,678 B2 | 1/2023 | Scheib et al. |
| 11,571,205 B2 | 2/2023 | Scheib et al. |
| 11,576,677 B2 | 2/2023 | Shelton, IV et al. |
| 11,589,888 B2 | 2/2023 | Shelton, IV et al. |
| 11,659,023 B2 | 5/2023 | Shelton, IV et al. |
| 11,712,309 B2 | 8/2023 | Barak et al. |
| 2001/0029315 A1 | 10/2001 | Sakurai et al. |
| 2001/0031975 A1 | 10/2001 | Whitman et al. |
| 2002/0022836 A1 | 2/2002 | Goble et al. |
| 2002/0052563 A1 | 5/2002 | Penn et al. |
| 2002/0148942 A1 | 10/2002 | Payne et al. |
| 2002/0151770 A1 | 10/2002 | Noll et al. |
| 2002/0183734 A1 | 12/2002 | Bommannan et al. |
| 2003/0007321 A1* | 1/2003 | Dayley ............... G06F 1/181 361/679.6 |
| 2003/0040670 A1 | 2/2003 | Govari |
| 2003/0050654 A1 | 3/2003 | Whitman et al. |
| 2003/0078631 A1 | 4/2003 | Nelson et al. |
| 2003/0093103 A1 | 5/2003 | Malackowski et al. |
| 2003/0114851 A1 | 6/2003 | Truckai et al. |
| 2003/0130677 A1 | 7/2003 | Whitman et al. |
| 2003/0199794 A1 | 10/2003 | Sakurai et al. |
| 2003/0199864 A1 | 10/2003 | Eick |
| 2004/0030328 A1 | 2/2004 | Eggers et al. |
| 2004/0059323 A1 | 3/2004 | Sturm et al. |
| 2004/0094597 A1 | 5/2004 | Whitman et al. |
| 2004/0111045 A1 | 6/2004 | Sullivan et al. |
| 2004/0111081 A1 | 6/2004 | Whitman et al. |
| 2004/0153724 A1 | 8/2004 | Nicholson et al. |
| 2004/0164983 A1 | 8/2004 | Khozai |
| 2005/0010209 A1 | 1/2005 | Lee et al. |
| 2005/0013459 A1 | 1/2005 | Maekawa |
| 2005/0021026 A1 | 1/2005 | Baily |
| 2005/0070800 A1 | 3/2005 | Takahashi |
| 2005/0090730 A1 | 4/2005 | Cortinovis et al. |
| 2005/0113815 A1 | 5/2005 | Ritchie et al. |
| 2005/0113823 A1 | 5/2005 | Reschke et al. |
| 2005/0127868 A1 | 6/2005 | Calhoon et al. |
| 2005/0127869 A1 | 6/2005 | Calhoon et al. |
| 2005/0131390 A1 | 6/2005 | Heinrich et al. |
| 2005/0159778 A1 | 7/2005 | Heinrich et al. |
| 2005/0165390 A1 | 7/2005 | Mauti et al. |
| 2005/0173490 A1 | 8/2005 | Shelton, IV |
| 2005/0229110 A1 | 10/2005 | Gegner et al. |
| 2005/0251233 A1 | 11/2005 | Kanzius |
| 2006/0020213 A1 | 1/2006 | Whitman et al. |
| 2006/0085049 A1 | 4/2006 | Cory et al. |
| 2006/0136622 A1 | 6/2006 | Rouvelin et al. |
| 2006/0149418 A1 | 7/2006 | Anvari |
| 2006/0212069 A1 | 9/2006 | Shelton, IV |
| 2006/0256516 A1 | 11/2006 | Cho |
| 2006/0278680 A1 | 12/2006 | Viola et al. |
| 2006/0278681 A1 | 12/2006 | Viola et al. |
| 2006/0289600 A1 | 12/2006 | Wales et al. |

(56) References Cited

U.S. PATENT DOCUMENTS

| | | |
|---|---|---|
| 2007/0061393 A1 | 3/2007 | Moore |
| 2007/0076363 A1 | 4/2007 | Liang et al. |
| 2007/0085602 A1 | 4/2007 | Park et al. |
| 2007/0136218 A1 | 6/2007 | Bauer et al. |
| 2007/0282321 A1 | 12/2007 | Shah et al. |
| 2008/0072896 A1 | 3/2008 | Setzer et al. |
| 2008/0090652 A1 | 4/2008 | Kuehling et al. |
| 2008/0129465 A1 | 6/2008 | Rao |
| 2008/0249377 A1 | 10/2008 | Molducci et al. |
| 2008/0316304 A1 | 12/2008 | Claus et al. |
| 2009/0036884 A1 | 2/2009 | Gregg et al. |
| 2009/0054908 A1 | 2/2009 | Zand et al. |
| 2009/0101692 A1 | 4/2009 | Whitman et al. |
| 2009/0131929 A1 | 5/2009 | Shimizu |
| 2009/0216091 A1 | 8/2009 | Arndt |
| 2009/0228024 A1 | 9/2009 | Whitfield et al. |
| 2009/0234352 A1 | 9/2009 | Behnke et al. |
| 2009/0273353 A1 | 11/2009 | Kroh et al. |
| 2010/0036405 A1 | 2/2010 | Giordano et al. |
| 2010/0069939 A1 | 3/2010 | Konishi |
| 2010/0076453 A1 | 3/2010 | Morris et al. |
| 2010/0092006 A1 | 4/2010 | Rosen |
| 2010/0120266 A1 | 5/2010 | Rimborg |
| 2010/0198200 A1 | 8/2010 | Horvath |
| 2010/0312239 A1 | 12/2010 | Sclig |
| 2011/0015660 A1 | 1/2011 | Wiener et al. |
| 2011/0092972 A1 | 4/2011 | Allen |
| 2011/0093796 A1 | 4/2011 | Plummer et al. |
| 2011/0106567 A1 | 5/2011 | Asher |
| 2011/0125149 A1 | 5/2011 | El-Galley et al. |
| 2011/0130689 A1 | 6/2011 | Cohen et al. |
| 2011/0238063 A1 | 9/2011 | Gregg |
| 2011/0245630 A1 | 10/2011 | St. Pierre et al. |
| 2011/0273465 A1 | 11/2011 | Konishi et al. |
| 2011/0288451 A1 | 11/2011 | Sanai et al. |
| 2011/0306840 A1 | 12/2011 | Allen et al. |
| 2012/0029304 A1 | 2/2012 | Medina et al. |
| 2012/0116380 A1 | 5/2012 | Madan et al. |
| 2012/0132661 A1 | 5/2012 | Gu et al. |
| 2012/0319890 A1 | 12/2012 | McCormack et al. |
| 2013/0031201 A1 | 1/2013 | Kagan et al. |
| 2013/0176220 A1 | 7/2013 | Merschon et al. |
| 2013/0197503 A1 | 8/2013 | Orszulak |
| 2013/0267975 A1 | 10/2013 | Timm et al. |
| 2013/0268283 A1 | 10/2013 | Vann et al. |
| 2014/0009894 A1* | 1/2014 | Yu .................. H05K 7/1465 361/735 |
| 2014/0058714 A1 | 2/2014 | Boyer |
| 2014/0087573 A1 | 3/2014 | Kroeckel |
| 2014/0097903 A1 | 4/2014 | Aoki et al. |
| 2014/0108048 A1 | 4/2014 | Cohn |
| 2014/0155721 A1 | 6/2014 | Hauck et al. |
| 2014/0180274 A1 | 6/2014 | Kabaya et al. |
| 2014/0194683 A1 | 7/2014 | Nakaguchi |
| 2014/0226572 A1 | 8/2014 | Thota et al. |
| 2014/0262598 A1 | 9/2014 | Miki et al. |
| 2014/0263552 A1 | 9/2014 | Hall et al. |
| 2014/0378958 A1 | 12/2014 | Leussler |
| 2015/0190189 A1 | 7/2015 | Yates et al. |
| 2015/0272575 A1 | 10/2015 | Leimbach et al. |
| 2015/0289929 A1 | 10/2015 | Toth et al. |
| 2015/0300923 A1 | 10/2015 | Halbert |
| 2015/0334879 A1 | 11/2015 | Fricker |
| 2015/0373115 A1 | 12/2015 | Breakstone et al. |
| 2016/0000495 A1 | 1/2016 | Elliott et al. |
| 2016/0045247 A1 | 2/2016 | Heim et al. |
| 2016/0045365 A1 | 2/2016 | Foster et al. |
| 2016/0058286 A1 | 3/2016 | Joshua et al. |
| 2016/0062954 A1 | 3/2016 | Ruff et al. |
| 2016/0074096 A1 | 3/2016 | Lieu |
| 2016/0120591 A1 | 5/2016 | Smith et al. |
| 2016/0164466 A1 | 6/2016 | Briffa et al. |
| 2016/0199240 A1 | 7/2016 | Newkirk et al. |
| 2016/0225192 A1 | 8/2016 | Jones et al. |
| 2016/0249945 A1 | 9/2016 | Shelton, IV et al. |
| 2016/0287312 A1 | 10/2016 | Tegg et al. |
| 2016/0287337 A1 | 10/2016 | Aram et al. |
| 2017/0000553 A1 | 1/2017 | Wiener et al. |
| 2017/0007146 A1 | 1/2017 | Schulhauser et al. |
| 2017/0024978 A1 | 1/2017 | Gulrez et al. |
| 2017/0078455 A1 | 3/2017 | Fisher et al. |
| 2017/0080346 A1 | 3/2017 | Abbas |
| 2017/0086911 A1 | 3/2017 | Wiener et al. |
| 2017/0090507 A1 | 3/2017 | Wiener et al. |
| 2017/0151011 A1 | 6/2017 | Brustad et al. |
| 2017/0189096 A1 | 7/2017 | Danziger et al. |
| 2017/0202595 A1 | 7/2017 | Shelton, IV |
| 2017/0209718 A1 | 7/2017 | Tanis |
| 2017/0251305 A1 | 8/2017 | Fathollahi |
| 2017/0252091 A1 | 9/2017 | Honda |
| 2017/0296213 A1 | 10/2017 | Swensgard et al. |
| 2017/0319259 A1 | 11/2017 | Dunning |
| 2017/0360466 A1 | 12/2017 | Brown et al. |
| 2018/0014872 A1 | 1/2018 | Dickerson |
| 2018/0042659 A1 | 2/2018 | Rupp et al. |
| 2018/0049795 A1 | 2/2018 | Swayze et al. |
| 2018/0065248 A1 | 3/2018 | Barral et al. |
| 2018/0078216 A1 | 3/2018 | Baker et al. |
| 2018/0082480 A1 | 3/2018 | White et al. |
| 2018/0099161 A1 | 4/2018 | Honda |
| 2018/0166809 A1 | 6/2018 | Brogan et al. |
| 2018/0206909 A1 | 7/2018 | Brustad et al. |
| 2018/0221005 A1 | 8/2018 | Hamel et al. |
| 2018/0228528 A1 | 8/2018 | Fraasch et al. |
| 2018/0239856 A1 | 8/2018 | Takeuchi et al. |
| 2018/0262916 A1 | 9/2018 | Polley et al. |
| 2018/0263557 A1 | 9/2018 | Kahlman |
| 2018/0296283 A1 | 10/2018 | Crawford et al. |
| 2018/0333207 A1 | 11/2018 | Moctezuma De La Barrera |
| 2018/0367870 A1 | 12/2018 | Shih |
| 2019/0000478 A1 | 1/2019 | Messerly et al. |
| 2019/0069957 A1 | 3/2019 | Barral et al. |
| 2019/0110855 A1 | 4/2019 | Barral et al. |
| 2019/0117322 A1 | 4/2019 | Laubenthal et al. |
| 2019/0125455 A1 | 5/2019 | Shelton, IV et al. |
| 2019/0197712 A1 | 6/2019 | Talbert et al. |
| 2019/0200844 A1 | 7/2019 | Shelton, IV et al. |
| 2019/0200906 A1 | 7/2019 | Shelton, IV et al. |
| 2019/0200981 A1 | 7/2019 | Harris et al. |
| 2019/0201102 A1 | 7/2019 | Shelton, IV et al. |
| 2019/0201140 A1 | 7/2019 | Yates et al. |
| 2019/0201158 A1 | 7/2019 | Shelton, IV et al. |
| 2019/0206563 A1 | 7/2019 | Shelton, IV et al. |
| 2019/0224434 A1 | 7/2019 | Silver et al. |
| 2019/0236840 A1 | 8/2019 | Zuckerman et al. |
| 2019/0247141 A1 | 8/2019 | Batchelor et al. |
| 2019/0247664 A1 | 8/2019 | Irazoqui et al. |
| 2019/0269457 A1 | 9/2019 | Schofield et al. |
| 2019/0278262 A1 | 9/2019 | Taylor et al. |
| 2019/0279524 A1 | 9/2019 | Stoyanov et al. |
| 2019/0348169 A1 | 11/2019 | Gibby et al. |
| 2019/0371012 A1 | 12/2019 | Flexman et al. |
| 2020/0004487 A1 | 1/2020 | Hanajima et al. |
| 2020/0015899 A1 | 1/2020 | Scheib et al. |
| 2020/0015900 A1 | 1/2020 | Scheib et al. |
| 2020/0015907 A1 | 1/2020 | Scheib |
| 2020/0015924 A1 | 1/2020 | Scheib et al. |
| 2020/0030044 A1 | 1/2020 | Wang et al. |
| 2020/0038120 A1 | 2/2020 | Ziraknejad et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078077 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078083 A1 | 3/2020 | Sprinkle et al. |
| 2020/0078089 A1 | 3/2020 | Henderson et al. |
| 2020/0078106 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |

(56) References Cited

U.S. PATENT DOCUMENTS

| | | |
|---|---|---|
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0129223 A1 | 4/2020 | Angeles et al. |
| 2020/0159313 A1 | 5/2020 | Gibby et al. |
| 2020/0237422 A1 | 7/2020 | Canady |
| 2020/0265398 A1 | 8/2020 | Lembo |
| 2020/0268472 A1 | 8/2020 | Wolf et al. |
| 2020/0305924 A1 | 10/2020 | Carroll |
| 2020/0305945 A1 | 10/2020 | Morgan et al. |
| 2020/0314569 A1 | 10/2020 | Morgan et al. |
| 2020/0342228 A1 | 10/2020 | Prevrhal et al. |
| 2020/0405375 A1 | 12/2020 | Shelton, IV et al. |
| 2021/0045804 A1 | 2/2021 | Schofield et al. |
| 2021/0121246 A1 | 4/2021 | Gudalo |
| 2021/0169578 A1 | 6/2021 | Calloway et al. |
| 2021/0196383 A1 | 7/2021 | Shelton, IV et al. |
| 2021/0203889 A1 | 7/2021 | Fung et al. |
| 2021/0212717 A1 | 7/2021 | Yates et al. |
| 2021/0236755 A1 | 8/2021 | King et al. |
| 2021/0264680 A1 | 8/2021 | Cvetko, Ph.D et al. |
| 2021/0313938 A1 | 10/2021 | Tanaka et al. |
| 2021/0338343 A1 | 11/2021 | Swaffield et al. |
| 2021/0385889 A1 | 12/2021 | Patel |
| 2022/0032442 A1 | 2/2022 | Sheffield et al. |
| 2022/0104867 A1 | 4/2022 | Shelton, IV et al. |
| 2022/0104896 A1 | 4/2022 | Shelton, IV et al. |
| 2022/0104897 A1 | 4/2022 | Shelton, IV et al. |
| 2022/0104911 A1 | 4/2022 | Shelton, IV et al. |
| 2022/0151704 A1 | 5/2022 | Nikou |
| 2022/0155910 A1 | 5/2022 | Jeong |
| 2022/0261056 A1 | 8/2022 | Motoi et al. |
| 2022/0313338 A1 | 10/2022 | Carroll et al. |
| 2022/0313341 A1 | 10/2022 | Wiener et al. |
| 2022/0313342 A1 | 10/2022 | Leuck et al. |
| 2022/0313357 A1 | 10/2022 | Geresy et al. |
| 2022/0313369 A1 | 10/2022 | Oberkircher et al. |
| 2022/0313370 A1 | 10/2022 | Morgan et al. |
| 2022/0313371 A1 | 10/2022 | Morgan et al. |
| 2022/0313372 A1 | 10/2022 | Herman et al. |
| 2022/0313373 A1 | 10/2022 | Morgan et al. |
| 2022/0317751 A1 | 10/2022 | Samuel et al. |
| 2022/0318179 A1 | 10/2022 | Morgan et al. |
| 2022/0319685 A1 | 10/2022 | Vachon et al. |
| 2022/0319693 A1 | 10/2022 | Oberkircher et al. |
| 2022/0321059 A1 | 10/2022 | Samuel et al. |
| 2022/0322523 A1 | 10/2022 | Jayme et al. |
| 2022/0331013 A1 | 10/2022 | Shelton, IV et al. |
| 2022/0331047 A1 | 10/2022 | Shelton, IV et al. |
| 2022/0331048 A1 | 10/2022 | Shelton, IV et al. |
| 2022/0331049 A1 | 10/2022 | Shelton, IV et al. |
| 2022/0331050 A1 | 10/2022 | Shelton, IV et al. |
| 2022/0331051 A1 | 10/2022 | Shelton, IV et al. |
| 2022/0331052 A1 | 10/2022 | Shelton, IV et al. |
| 2022/0331053 A1 | 10/2022 | Kimball et al. |
| 2022/0331054 A1 | 10/2022 | Kimball et al. |
| 2022/0331056 A1 | 10/2022 | Shelton, IV et al. |
| 2022/0334787 A1 | 10/2022 | Jogan et al. |
| 2022/0335604 A1 | 10/2022 | Vanosdoll et al. |
| 2022/0335660 A1 | 10/2022 | Shelton, IV et al. |
| 2022/0335696 A1 | 10/2022 | Shelton, IV et al. |
| 2022/0336078 A1 | 10/2022 | Wise et al. |
| 2022/0336097 A1 | 10/2022 | Shelton, IV et al. |
| 2022/0337891 A1 | 10/2022 | Burnley et al. |
| 2022/0338049 A1 | 10/2022 | Ross et al. |
| 2023/0038130 A1 | 2/2023 | Cvetko et al. |
| 2023/0039037 A1 | 2/2023 | Henderson et al. |
| 2023/0069787 A1 | 3/2023 | Henderson et al. |
| 2023/0072423 A1 | 3/2023 | Osborn et al. |
| 2023/0346446 A1 | 11/2023 | Henderson et al. |
| 2023/0397941 A1 | 12/2023 | Henderson et al. |

FOREIGN PATENT DOCUMENTS

| | | |
|---|---|---|
| EP | 0929263 B1 | 7/1999 |
| EP | 1006892 B1 | 6/2009 |
| EP | 2942023 A2 | 11/2015 |
| JP | S635457 A | 1/1988 |
| JP | H03041943 A | 2/1991 |
| JP | H8280706 A | 10/1996 |
| JP | H1069453 A | 3/1998 |
| JP | H11318921 A | 11/1999 |
| JP | 2000089850 A | 3/2000 |
| JP | 2000217836 A | 8/2000 |
| JP | 2000515050 A | 11/2000 |
| JP | 2001029353 A | 2/2001 |
| JP | 2001128993 A | 5/2001 |
| JP | 2002336194 A | 11/2002 |
| JP | 2004008581 A | 1/2004 |
| JP | 2004097474 A | 4/2004 |
| JP | 2004290516 A | 10/2004 |
| JP | 2006303167 A | 11/2006 |
| JP | 2007174666 A | 7/2007 |
| JP | 2009291308 A | 12/2009 |
| JP | 2010063883 A | 3/2010 |
| JP | 2014210052 A | 11/2014 |
| JP | 2015535193 A | 12/2015 |
| KR | 20110081018 A | 7/2011 |
| WO | WO-0112089 A1 | 2/2001 |
| WO | WO-2008053485 A1 | 5/2008 |
| WO | WO-2014031800 A1 | 2/2014 |
| WO | WO-2014071184 A1 | 5/2014 |
| WO | WO-2015047693 A1 | 4/2015 |
| WO | WO-2017058617 | 4/2017 |
| WO | WO-2018116247 A1 | 6/2018 |
| WO | WO-2019215354 A1 | 11/2019 |
| WO | WO-2021044136 A1 | 3/2021 |

OTHER PUBLICATIONS

IEEE Std 802.Mar. 2012 (Revision of IEEE Std 802.3-2008, published Dec. 28, 2012.
"ATM-MPLS Network Interworking Version 2.0, af-aic-0178.001" ATM Standard, The ATM Forum Technical Committe, published Aug. 2003.
Zhu et al. "Haptic-feedback smart glove as a creative human-machine interface (HMI) for virtual/augmented reality applications," Sci. Adv, vol. 6, No. 19, May 8, 2020.
Qian, et al., "A Review of Augmented Reality in Robotic-Assisted Surgery", IEEE Transactions On Medical Robotics and Bionics, IEEE, vol. 2, No. 1, pp. 1-16, Feb. 2020.
Yu et al., "Skin-Integrated Wireless Haptic Interfaces for Virtual and Augmented Reality," Nature, vol. 575, pp. 473-479, Nov. 21, 2019.
Li et al., "Wearable Energy Harvesters Generating Electricity From Low-Frequency Human Limb Movement," Microsystems & Nanoengineering (2018), vol. 4(24), 13 pages.
"BOWA ARC 400" Oct. 30, 2018, posted at bowa-medical.com, [site visited Aug. 6, 2021], https://www.bowa-medical.com/tradepro/shopru/artikel/allgemein/BOWA_BRO_11181_ARC400_V2.1_2018_10_30_EN.pdf (Year: 2018).
"Electrosurgical Generator ECONT-0201.3" Mar. 18, 2018, posted at contact-endoscopy.com, [site visited Aug. 6, 2021], https://contact-endoscopy.com/electrosurgical-system (Year: 2018).

* cited by examiner

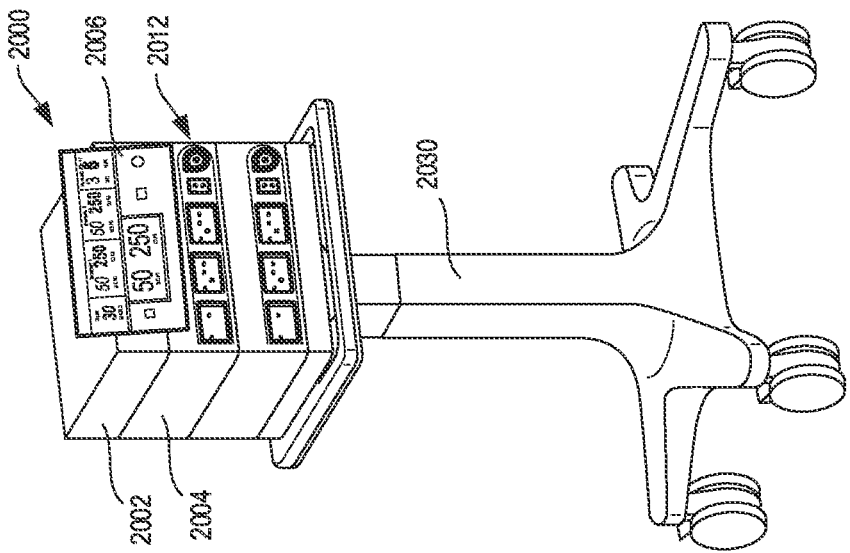
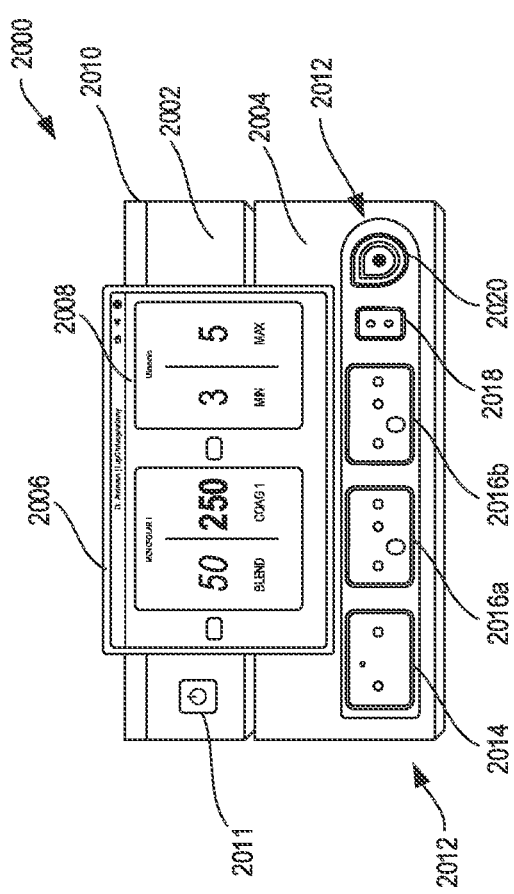
FIG. 7B
FIG. 7A

BACKPLANE CONNECTOR ATTACHMENT MECHANISM FOR MODULAR ENERGY SYSTEM

BACKGROUND

The present disclosure relates to various surgical systems, including modular electrosurgical and/or ultrasonic surgical systems. Operating rooms (ORs) are in need of streamlined capital solutions because ORs are a tangled web of cords, devices, and people due to the number of different devices that are needed to complete each surgical procedure. This is a reality of every OR in every market throughout the globe. Capital equipment is a major offender in creating clutter within ORs because most capital equipment performs one task or job, and each type of capital equipment requires unique techniques or methods to use and has a unique user interface. Accordingly, there are unmet consumer needs for capital equipment and other surgical technology to be consolidated in order to decrease the equipment footprint within the OR, streamline the equipment's interfaces, and improve surgical staff efficiency during a surgical procedure by reducing the number of devices that surgical staff members need to interact with.

SUMMARY

In one general aspect, the present disclosure provides a modular energy system that comprises a first module, comprising a first panel, and a first connector attached to the first panel. A portion of the first connector extends past a first edge of the first panel. The modular energy system further comprises a second module, comprising a second panel, and a second connector attached to the second panel. The second connector is aligned with a second edge of the second panel, and the second connector defines a cavity. The second module is coupled to the first module, wherein the portion of the first connector that extends past the first edge of the first panel is positioned within the cavity defined by the second connector.

In another aspect, the present disclosure provides a modular energy system, comprising a first module. The first module comprises a first panel. The first panel comprises a first support member attached to the panel, and a second support member attached to the panel, wherein the second support member is offset from the first support member. The first panel further comprises a support ledge attached to the first panel, wherein the support ledge is located between the first support member and the second support member. The first module further comprises a first connector, defining a first hole in the first connector. The first connector comprises a support rib that extends away from the first connector. The first connector is slidably attachable to the first panel, wherein the first support member is slidably insertable into the first hole. In the attached configuration, the support rib is configured to rest against the support ledge. In the attached configuration, a portion of the first connector extends past a first edge of the first panel. The first module further comprises a second connector defining a cavity and a second hole. The second connector is slidably attachable to the first panel, wherein the second support member is slidably receivable into the second hole. In the attached configuration the second connector is aligned with a second edge of the first panel, wherein the second edge of the first panel is opposite the first edge of the first panel.

In another aspect, the present disclosure provides a module for a modular energy system, the module comprises a panel. The panel comprises a first support member attached to and extending away from the panel, a second support member attached to and extending away from the panel, wherein the second support member is offset from the first support member. The module further comprises a first connector defining a first hole in the first connector. The first connector is slidably attachable to the panel, wherein the first support member is slidably receivable into the first hole. In the attached configuration a portion of the first connector extends past a first edge of the panel. The module further comprises a second connector defining a cavity and a second hole. The second connector is slidably attachable to the first panel, wherein the second support member is slidably receivable into the second hole. In the attached configuration the second connector is aligned with a second edge of the panel, and wherein the second edge of the first panel is opposite the first edge of the panel.

In yet another aspect, the present disclosure provides a modular energy system that comprises a header module, wherein the header module is configured to supply power to one or more connected dependent modules. The a modular energy system further comprises at least one dependent module connected to the header module and powered by the header module, and a power module connected to the dependent module, wherein the power module is configured to supply power to one or more other connected dependent modules.

FIGURES

The various aspects described herein, both as to organization and methods of operation, together with further objects and advantages thereof, may best be understood by reference to the following description, taken in conjunction with the accompanying drawings as follows.

FIG. 7A is a first illustrative modular energy system configuration including a header module and a display screen that renders a graphical user interface (GUI) for relaying information regarding modules connected to the header module, in accordance with at least one aspect of the present disclosure.

FIG. 7B is the modular energy system shown in FIG. 7A mounted to a cart, in accordance with at least one aspect of the present disclosure.

Corresponding reference characters indicate corresponding parts throughout the several views. The exemplifications set out herein illustrate various disclosed aspects, in one form, and such exemplifications are not to be construed as limiting the scope thereof in any manner.

DESCRIPTION

Figure 1:
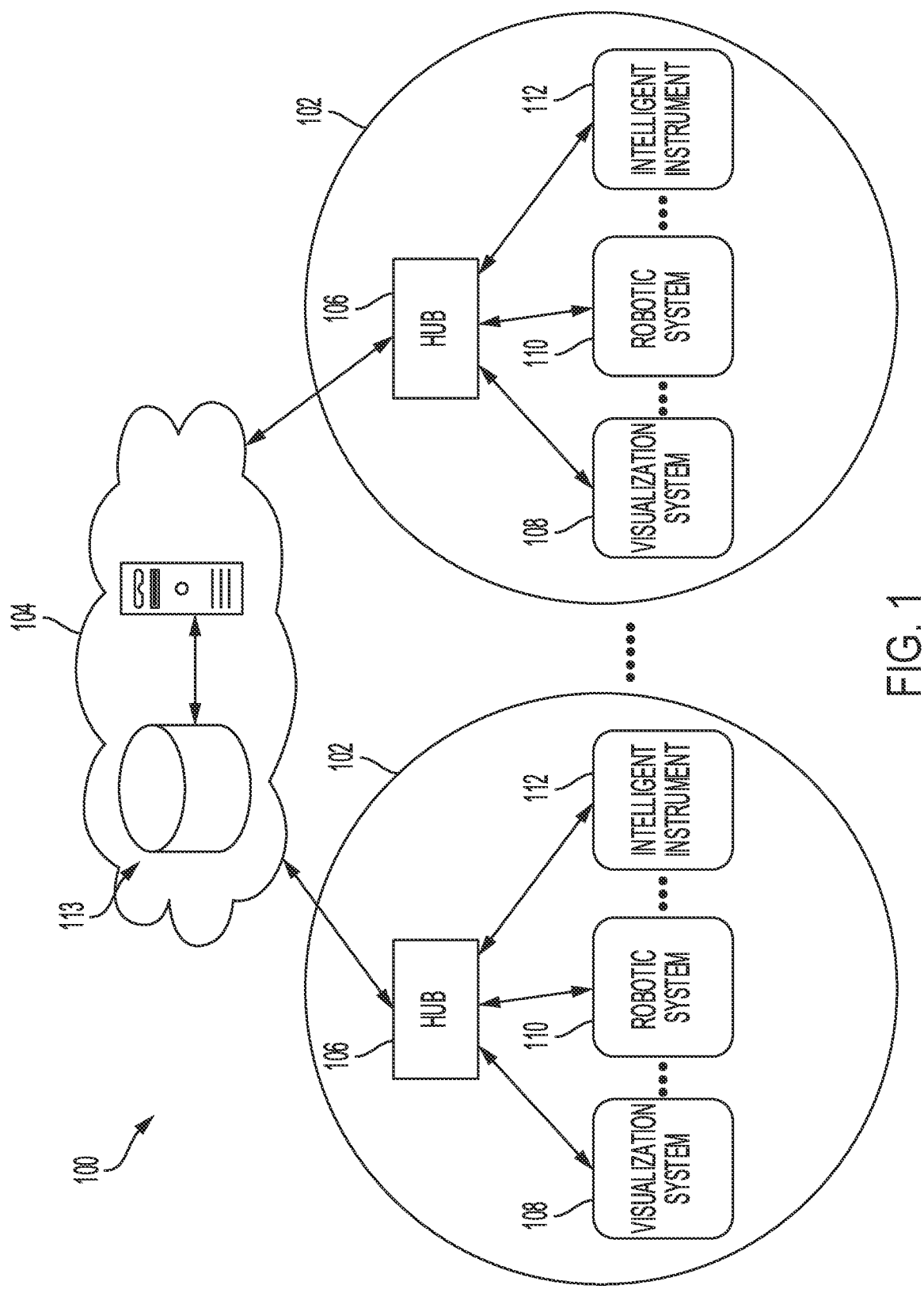
FIG. 1 is a block diagram of a computer-implemented interactive surgical system, in accordance with at least one aspect of the present disclosure.

Applicant of the present application owns the following U.S. Patent Applications filed on Mar. 30, 2021, the disclosure of each of which is herein incorporated by reference in its entirety:
- U.S. patent application Ser. No. 17/217,394, titled METHOD FOR MECHANICAL PACKAGING FOR MODULAR ENERGY SYSTEM, now U.S. Patent Application Publication No. 2022/0322523;
- U.S. patent application Ser. No. 17/217,436, titled BEZEL WITH LIGHT BLOCKING FEATURES FOR MODULAR ENERGY SYSTEM, now U.S. Pat. No. 11,857,252;
- U.S. patent application Ser. No. 17/217,446, titled HEADER FOR MODULAR ENERGY SYSTEM, now U.S. Patent Application Publication No. 2022/0313342;
- U.S. patent application Ser. No. 17/217,403, titled SURGICAL PROCEDURALIZATION VIA MODULAR ENERGY SYSTEM, now U.S. Patent Application Publication No. 2022/0313341;
- U.S. patent application Ser. No. 17/217,424, titled METHOD FOR ENERGY DELIVERY FOR MODULAR ENERGY SYSTEM, now U.S. Patent Application Publication No. 2022/0317751;
- U.S. patent application Ser. No. 17/217,439, titled MODULAR ENERGY SYSTEM WITH DUAL AMPLIFIERS AND TECHNIQUES FOR UPDATING PARAMETERS THEREOF, now U.S. Patent Application Publication No. 2022/0321059;
- U.S. patent application Ser. No. 17/217,471, titled MODULAR ENERGY SYSTEM WITH MULTI-ENERGY PORT SPLITTER FOR MULTIPLE ENERGY DEVICES, now U.S. Patent Application Publication No. 2022/0313373;
- U.S. patent application Ser. No. 17/217,385, titled METHOD FOR INTELLIGENT INSTRUMENTS FOR MODULAR ENERGY SYSTEM, now U.S. Patent Application Publication No. 2022/0313369;
- U.S. patent application Ser. No. 17/217,392, titled RADIO FREQUENCY IDENTIFICATION TOKEN FOR WIRELESS SURGICAL INSTRUMENTS, now U.S. Patent Application Publication No. 2022/0319693;
- U.S. patent application Ser. No. 17/217,397, titled INTELLIGENT DATA PORTS FOR MODULAR ENERGY SYSTEMS, now U.S. Patent Application Publication No. 2022/0318179;
- U.S. patent application Ser. No. 17/217,405, titled METHOD FOR SYSTEM ARCHITECTURE FOR MODULAR ENERGY SYSTEM, now U.S. Patent Application Publication No. 2022/0313370;
- U.S. patent application Ser. No. 17/217,423, titled USER INTERFACE MITIGATION TECHNIQUES FOR MODULAR ENERGY SYSTEMS, now U.S. Patent Application Publication No. 2022/0313371;
- U.S. patent application Ser. No. 17/217,429, titled ENERGY DELIVERY MITIGATIONS FOR MODULAR ENERGY SYSTEMS, now U.S. Patent Application Publication No. 2022/0313338;
- U.S. patent application Ser. No. 17/217,449, titled ARCHITECTURE FOR MODULAR ENERGY SYSTEM, now U.S. Patent Application Publication No. 2022/0313372; and
- U.S. patent application Ser. No. 17/217,461, titled MODULAR ENERGY SYSTEM WITH HARDWARE MITIGATED COMMUNICATION, now U.S. Patent Application Publication No. 2022/0319685.

Applicant of the present application owns the following U.S. Patent Applications filed Sep. 5, 2019, the disclosure of each of which is herein incorporated by reference in its entirety:
- U.S. patent application Ser. No. 16/562,144, titled METHOD FOR CONTROLLING A MODULAR ENERGY SYSTEM USER INTERFACE, now U.S. Patent Application Publication No. 2020/0078106;
- U.S. patent application Ser. No. 16/562,151, titled PASSIVE HEADER MODULE FOR A MODULAR ENERGY SYSTEM, now U.S. Patent Application Publication No. 2020/0078110;
- U.S. patent application Ser. No. 16/562,157, titled CONSOLIDATED USER INTERFACE FOR MODULAR ENERGY SYSTEM, now U.S. Patent Application Publication No. 2020/0081585;
- U.S. patent application Ser. No. 16/562,159, titled AUDIO TONE CONSTRUCTION FOR AN ENERGY MODULE OF A MODULAR ENERGY SYSTEM, now U.S. Patent Application Publication No. 2020/0314569;
- U.S. patent application Ser. No. 16/562,163, titled ADAPTABLY CONNECTABLE AND REASSIGNABLE SYSTEM ACCESSORIES FOR MODULAR ENERGY SYSTEM, now U.S. Patent Application Publication No. 2020/0078111;
- U.S. patent application Ser. No. 16/562,123, titled METHOD FOR CONSTRUCTING AND USING A MODULAR SURGICAL ENERGY SYSTEM WITH MULTIPLE DEVICES, now U.S. Patent Application Publication No. 2020/0100830;
- U.S. patent application Ser. No. 16/562,135, titled METHOD FOR CONTROLLING AN ENERGY MODULE OUTPUT, now U.S. Patent Application Publication No. 2020/0078076;
- U.S. patent application Ser. No. 16/562,180, titled ENERGY MODULE FOR DRIVING MULTIPLE ENERGY MODALITIES, now U.S. Patent Application Publication No. 2020/0078080;
- U.S. patent application Ser. No. 16/562,184, titled GROUNDING ARRANGEMENT OF ENERGY MODULES, now U.S. Patent Application Publication No. 2020/0078081;
- U.S. patent application Ser. No. 16/562,188, titled BACKPLANE CONNECTOR DESIGN TO CONNECT STACKED ENERGY MODULES, now U.S. Patent Application Publication No. 2020/0078116;
- U.S. patent application Ser. No. 16/562,195, titled ENERGY MODULE FOR DRIVING MULTIPLE ENERGY MODALITIES THROUGH A PORT, now U.S. Patent Application Publication No. 20200078117;
- U.S. patent application Ser. No. 16/562,202 titled SURGICAL INSTRUMENT UTILIZING DRIVE SIGNAL TO POWER SECONDARY FUNCTION, now U.S. Patent Application Publication No. 2020/0078082;
- U.S. patent application Ser. No. 16/562,142, titled METHOD FOR ENERGY DISTRIBUTION IN A SURGICAL MODULAR ENERGY SYSTEM, now U.S. Patent Application Publication No. 2020/0078070;

U.S. patent application Ser. No. 16/562,169, titled SURGICAL MODULAR ENERGY SYSTEM WITH A SEGMENTED BACKPLANE, now U.S. Patent Application Publication No. 2020/0078112;

U.S. patent application Ser. No. 16/562,185, titled SURGICAL MODULAR ENERGY SYSTEM WITH FOOTER MODULE, now U.S. Patent Application Publication No. 2020/0078115;

U.S. patent application Ser. No. 16/562,203, titled POWER AND COMMUNICATION MITIGATION ARRANGEMENT FOR MODULAR SURGICAL ENERGY SYSTEM, now U.S. Patent Application Publication No. 2020/0078118;

U.S. patent application Ser. No. 16/562,212, titled MODULAR SURGICAL ENERGY SYSTEM WITH MODULE POSITIONAL AWARENESS SENSING WITH VOLTAGE DETECTION, now U.S. Patent Application Publication No. 2020/0078119;

U.S. patent application Ser. No. 16/562,234, titled MODULAR SURGICAL ENERGY SYSTEM WITH MODULE POSITIONAL AWARENESS SENSING WITH TIME COUNTER, now U.S. Patent Application Publication No. 2020/0305945;

U.S. patent application Ser. No. 16/562,243, titled MODULAR SURGICAL ENERGY SYSTEM WITH MODULE POSITIONAL AWARENESS WITH DIGITAL LOGIC, now U.S. Patent Application Publication No. 2020/0078120;

U.S. patent application Ser. No. 16/562,125, titled METHOD FOR COMMUNICATING BETWEEN MODULES AND DEVICES IN A MODULAR SURGICAL SYSTEM, now U.S. Patent Application Publication No. 2020/0100825;

U.S. patent application Ser. No. 16/562,137, titled FLEXIBLE HAND-SWITCH CIRCUIT, now U.S. Patent Application Publication No. 2020/0106220;

U.S. patent application Ser. No. 16/562,143, titled FIRST AND SECOND COMMUNICATION PROTOCOL ARRANGEMENT FOR DRIVING PRIMARY AND SECONDARY DEVICES THROUGH A SINGLE PORT, now U.S. Patent Application Publication No. 2020/0090808;

U.S. patent application Ser. No. 16/562,148, titled FLEXIBLE NEUTRAL ELECTRODE, now U.S. Patent Application Publication No. 2020/0078077;

U.S. patent application Ser. No. 16/562,154, titled SMART RETURN PAD SENSING THROUGH MODULATION OF NEAR FIELD COMMUNICATION AND CONTACT QUALITY MONITORING SIGNALS, now U.S. Patent Application Publication No. 2020/0078089;

U.S. patent application Ser. No. 16/562,162, titled AUTOMATIC ULTRASONIC ENERGY ACTIVATION CIRCUIT DESIGN FOR MODULAR SURGICAL SYSTEMS, now U.S. Patent Application Publication No. 2020/0305924;

U.S. patent application Ser. No. 16/562,167, titled COORDINATED ENERGY OUTPUTS OF SEPARATE BUT CONNECTED MODULES, now U.S. Patent Application Publication No. 2020/0078078;

U.S. patent application Ser. No. 16/562,170, titled MANAGING SIMULTANEOUS MONOPOLAR OUTPUTS USING DUTY CYCLE AND SYNCHRONIZATION, now U.S. Patent Application Publication No. 2020/0078079;

U.S. patent application Ser. No. 16/562,172, titled PORT PRESENCE DETECTION SYSTEM FOR MODULAR ENERGY SYSTEM, now U.S. Patent Application Publication No. 2020/0078113;

U.S. patent application Ser. No. 16/562,175, titled INSTRUMENT TRACKING ARRANGEMENT BASED ON REAL TIME CLOCK INFORMATION, now U.S. Patent Application Publication No. 2020/0078071;

U.S. patent application Ser. No. 16/562,177, titled REGIONAL LOCATION TRACKING OF COMPONENTS OF A MODULAR ENERGY SYSTEM, now U.S. Patent Application Publication No. 2020/0078114;

U.S. Design patent application Ser. No. 29/704,610, titled ENERGY MODULE;

U.S. Design patent application Ser. No. 29/704,614, titled ENERGY MODULE MONOPOLAR PORT WITH FOURTH SOCKET AMONG THREE OTHER SOCKETS;

U.S. Design patent application Ser. No. 29/704,616, titled BACKPLANE CONNECTOR FOR ENERGY MODULE; and U.S. Design Patent application serial Ser. No. 29/704,617, titled ALERT SCREEN FOR ENERGY MODULE.

Applicant of the present application owns the following U.S. Patent Provisional Applications filed Mar. 29, 2019, the disclosure of each of which is herein incorporated by reference in its entirety:

U.S. Provisional Patent Application Ser. No. 62/826,584, titled MODULAR SURGICAL PLATFORM ELECTRICAL ARCHITECTURE;

U.S. Provisional Patent Application Ser. No. 62/826,587, titled MODULAR ENERGY SYSTEM CONNECTIVITY;

U.S. Provisional Patent Application Ser. No. 62/826,588, titled MODULAR ENERGY SYSTEM INSTRUMENT COMMUNICATION TECHNIQUES; and U.S. Provisional Patent Application Ser. No. 62/826,592, titled MODULAR ENERGY DELIVERY SYSTEM.

Applicant of the present application owns the following U.S. Patent Provisional Application filed Sep. 7, 2018, the disclosure of each of which is herein incorporated by reference in its entirety:

U.S. Provisional Patent Application Ser. No. 62/728,480, titled MODULAR ENERGY SYSTEM AND USER INTERFACE.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to improved ultrasonic surgical devices, electrosurgical devices and generators for use therewith. Aspects of the ultrasonic surgical devices can be configured for transecting and/or coagulating tissue during surgical procedures, for example. Aspects of the electrosurgical devices can be configured for transecting, coagulating, scaling, welding and/or desiccating tissue during surgical procedures, for example.

Surgical System Hardware

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 2:
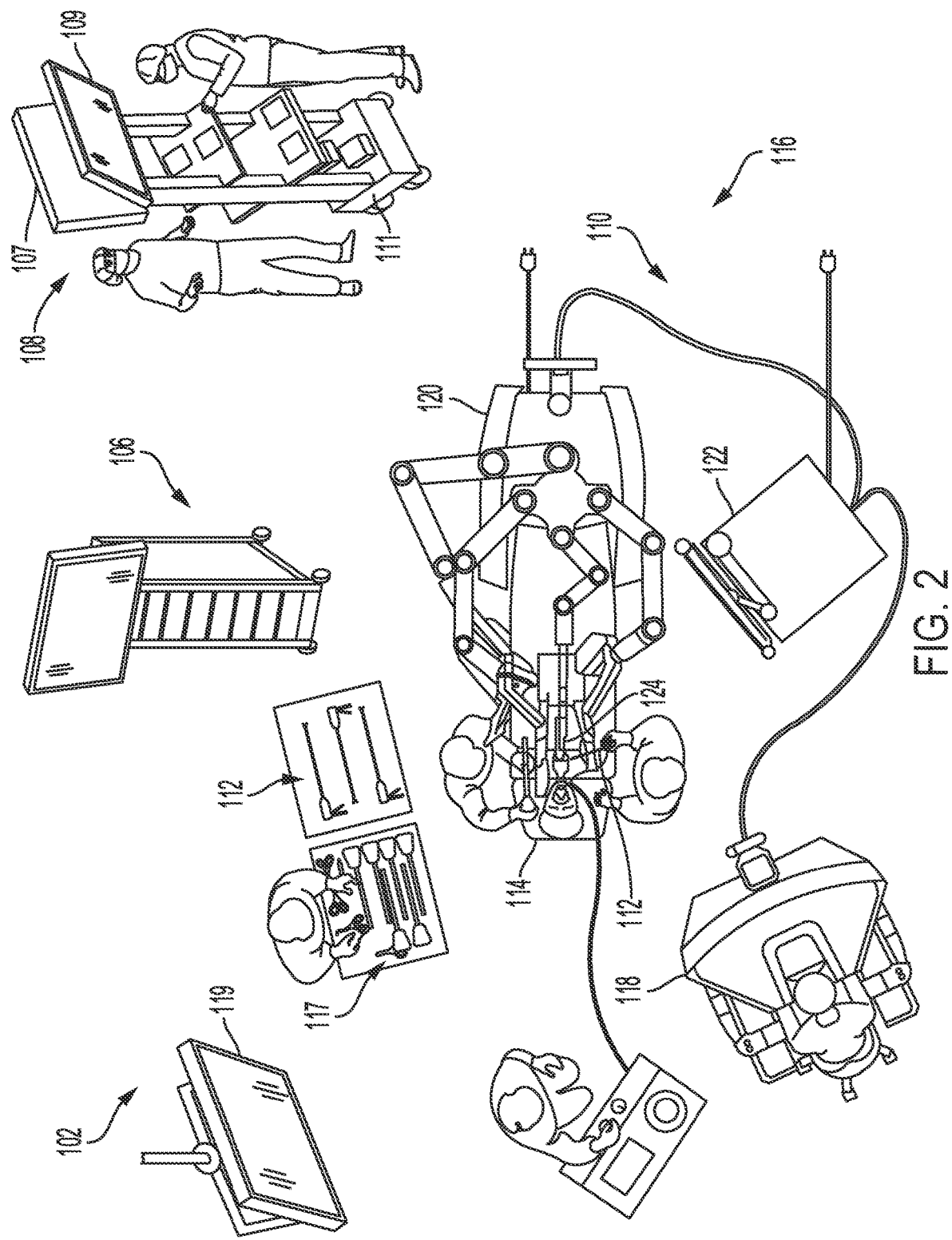
FIG. 2 is a surgical system being used to perform a surgical procedure in an operating room, in accordance with at least one aspect of the present disclosure.

FIG. 2 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading SURGICAL INSTRUMENT HARDWARE and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 3:
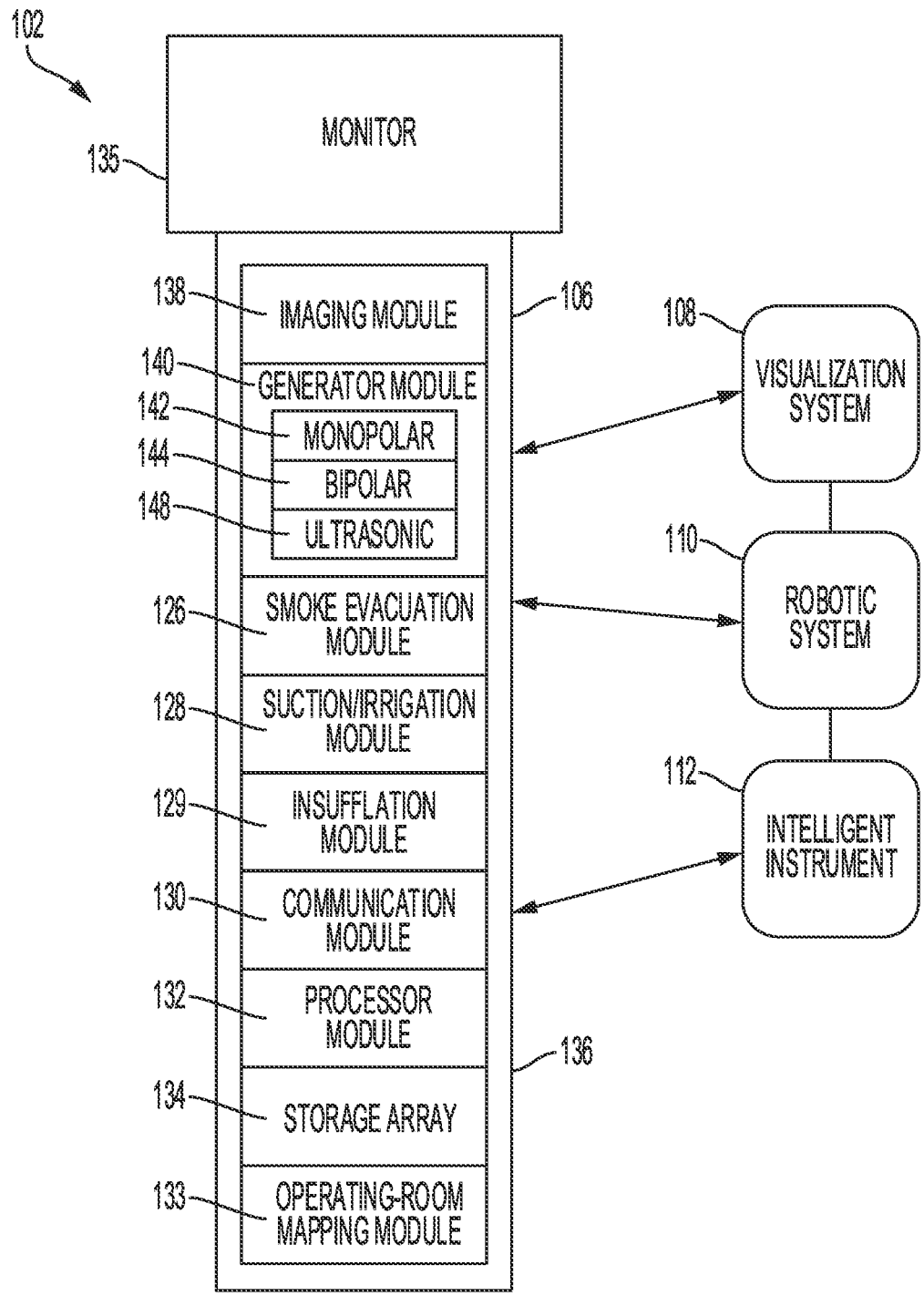
FIG. 3 is a surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. In some aspects, the visualization system 108 may be a separable piece of equipment. In alternative aspects, the visualization system 108 could be contained within the hub 106 as a functional module. The hub 106 includes a hub display 135, an imaging module 138, a generator module 140, a communication module 130, a processor module 132, a storage array 134, and an operating room mapping module 133. In certain aspects, as illustrated in FIG. 3, the hub 106 further includes a smoke evacuation module 126, a suction/irrigation module 128, and/or an insufflation module 129. In certain aspects, any of the modules in the hub 106 may be combined with each other into a single module.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes one or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts. In one aspect, the first energy-generator module is slidably movable into an electrical engagement with the power and data contacts and wherein the first energy-generator module is slidably movable out of the electrical engagement with the first power and data contacts. In an alternative aspect, the first energy-generator module is stackably movable into an electrical engagement with the power and data contacts and wherein the first energy-generator module is stackably movable out of the electrical engagement with the first power and data contacts.

Further to the above, the modular surgical enclosure also includes a second energy-generator module configured to generate a second energy, either the same or different than the first energy, for application to the tissue, and a second docking station comprising a second docking port that includes second data and power contacts. In one aspect, the second energy-generator module is slidably movable into an electrical engagement with the power and data contacts, and wherein the second energy-generator module is slidably movable out of the electrical engagement with the second power and data contacts. In an alternative aspect, the second energy-generator module is stackably movable into an electrical engagement with the power and data contacts, and wherein the second energy-generator module is stackably movable out of the electrical engagement with the second power and data contacts.

In addition, the modular surgical enclosure also includes a communication bus between the first docking port and the second docking port, configured to facilitate communication between the first energy-generator module and the second energy-generator module.

Referring to FIG. 3, aspects of the present disclosure are presented for a hub modular enclosure 136 that allows the modular integration of a generator module 140, a smoke evacuation module 126, a suction/irrigation module 128, and an insufflation module 129. The hub modular enclosure 136 further facilitates interactive communication between the modules 140, 126, 128, 129. The generator module 140 can be a generator module with integrated monopolar, bipolar, and ultrasonic components supported in a single housing unit slidably insertable into the hub modular enclosure 136. The generator module 140 can be configured to connect to a monopolar device 142, a bipolar device 144, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128, 129 and interactive communication therebetween.

Generator Hardware

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; a SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4× known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIG. 3, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Figure 4:
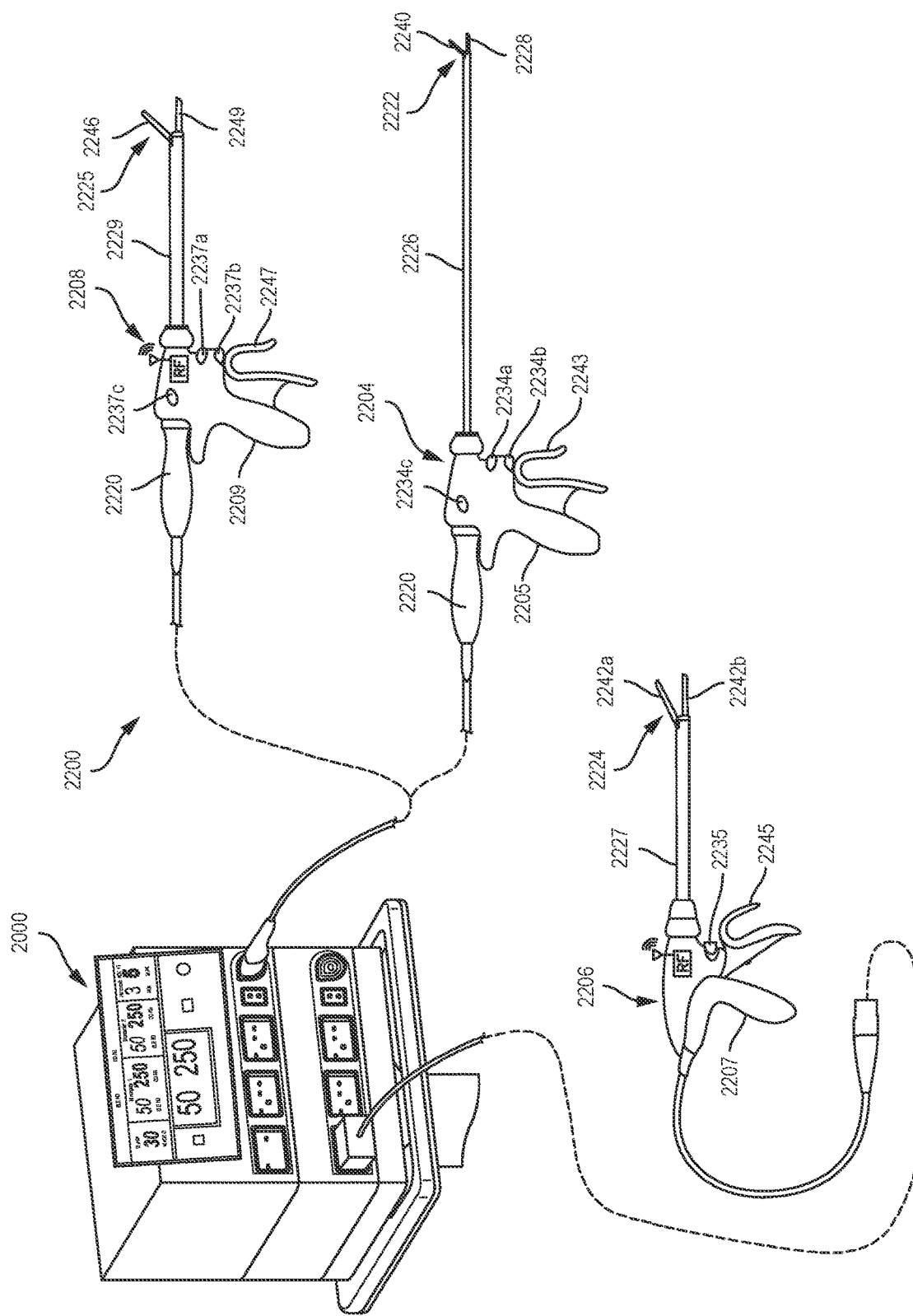
FIG. 4 is a surgical system comprising a generator and various surgical instruments usable therewith, in accordance with at least one aspect of the present disclosure.

FIG. 4 illustrates one form of a surgical system 2200 comprising a modular energy system 2000 and various surgical instruments 2204, 2206, 2208 usable therewith, where the surgical instrument 2204 is an ultrasonic surgical instrument, the surgical instrument 2206 is an RF electrosurgical instrument, and the multifunction surgical instrument 2208 is a combination ultrasonic/RF electrosurgical instrument. The modular energy system 2000 is configurable for use with a variety of surgical instruments. According to various forms, the modular energy system 2000 may be configurable for use with different surgical instruments of different types including, for example, ultrasonic surgical instruments 2204, RF electrosurgical instruments 2206, and multifunction surgical instruments 2208 that integrate RF and ultrasonic energies delivered individually or simultaneously from the modular energy system 2000. Although in the form of FIG. 4 the modular energy system 2000 is shown separate from the surgical instruments 2204, 2206, 2208 in one form, the modular energy system 2000 may be formed integrally with any of the surgical instruments 2204, 2206, 2208 to form a unitary surgical system. The modular energy system 2000 may be configured for wired or wireless communication.

The modular energy system 2000 is configured to drive multiple surgical instruments 2204, 2206, 2208. The first surgical instrument is an ultrasonic surgical instrument 2204 and comprises a handpiece 2205 (HP), an ultrasonic transducer 2220, a shaft 2226, and an end effector 2222. The end effector 2222 comprises an ultrasonic blade 2228 acoustically coupled to the ultrasonic transducer 2220 and a clamp arm 2240. The handpiece 2205 comprises a trigger 2243 to operate the clamp arm 2240 and a combination of the toggle buttons 2234a, 2234b, 2234c to energize and drive the ultrasonic blade 2228 or other function. The toggle buttons 2234a, 2234b, 2234c can be configured to energize the ultrasonic transducer 2220 with the modular energy system 2000.

The modular energy system 2000 also is configured to drive a second surgical instrument 2206. The second surgical instrument 2206 is an RF electrosurgical instrument and comprises a handpiece 2207 (HP), a shaft 2227, and an end effector 2224. The end effector 2224 comprises electrodes in clamp arms 2242a, 2242b and return through an electrical conductor portion of the shaft 2227. The electrodes are coupled to and energized by a bipolar energy source within the modular energy system 2000. The handpiece 2207 comprises a trigger 2245 to operate the clamp arms 2242a, 2242b and an energy button 2235 to actuate an energy switch to energize the electrodes in the end effector 2224.

The modular energy system 2000 also is configured to drive a multifunction surgical instrument 2208. The multifunction surgical instrument 2208 comprises a handpiece 2209 (HP), a shaft 2229, and an end effector 2225. The end effector 2225 comprises an ultrasonic blade 2249 and a clamp arm 2246. The ultrasonic blade 2249 is acoustically coupled to the ultrasonic transducer 2220. The ultrasonic transducer 2220 may be separable from or integral to the handpiece 2209. The handpiece 2209 comprises a trigger 2247 to operate the clamp arm 2246 and a combination of the toggle buttons 2237a, 2237b, 2237c to energize and drive the ultrasonic blade 2249 or other function. The toggle buttons 2237a, 2237b, 2237c can be configured to energize the ultrasonic transducer 2220 with the modular energy system 2000 and energize the ultrasonic blade 2249 with a bipolar energy source also contained within the modular energy system 2000.

The modular energy system 2000 is configurable for use with a variety of surgical instruments. According to various forms, the modular energy system 2000 may be configurable for use with different surgical instruments of different types including, for example, the ultrasonic surgical instrument 2204, the RF electrosurgical instrument 2206, and the multifunction surgical instrument 2208 that integrates RF and ultrasonic energies delivered individually or simultaneously from the modular energy system 2000. Although in the form of FIG. 4 the modular energy system 2000 is shown separate from the surgical instruments 2204, 2206, 2208, in another form the modular energy system 2000 may be formed integrally with any one of the surgical instruments 2204, 2206, 2208 to form a unitary surgical system. Further aspects of generators for digitally generating electrical signal waveforms and surgical instruments are described in U.S. Patent Application Publication No. 2017/0086914, which is herein incorporated by reference in its entirety.

Situational Awareness

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or sub optimally given the particular context-free sensed data. For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

Figure 5:
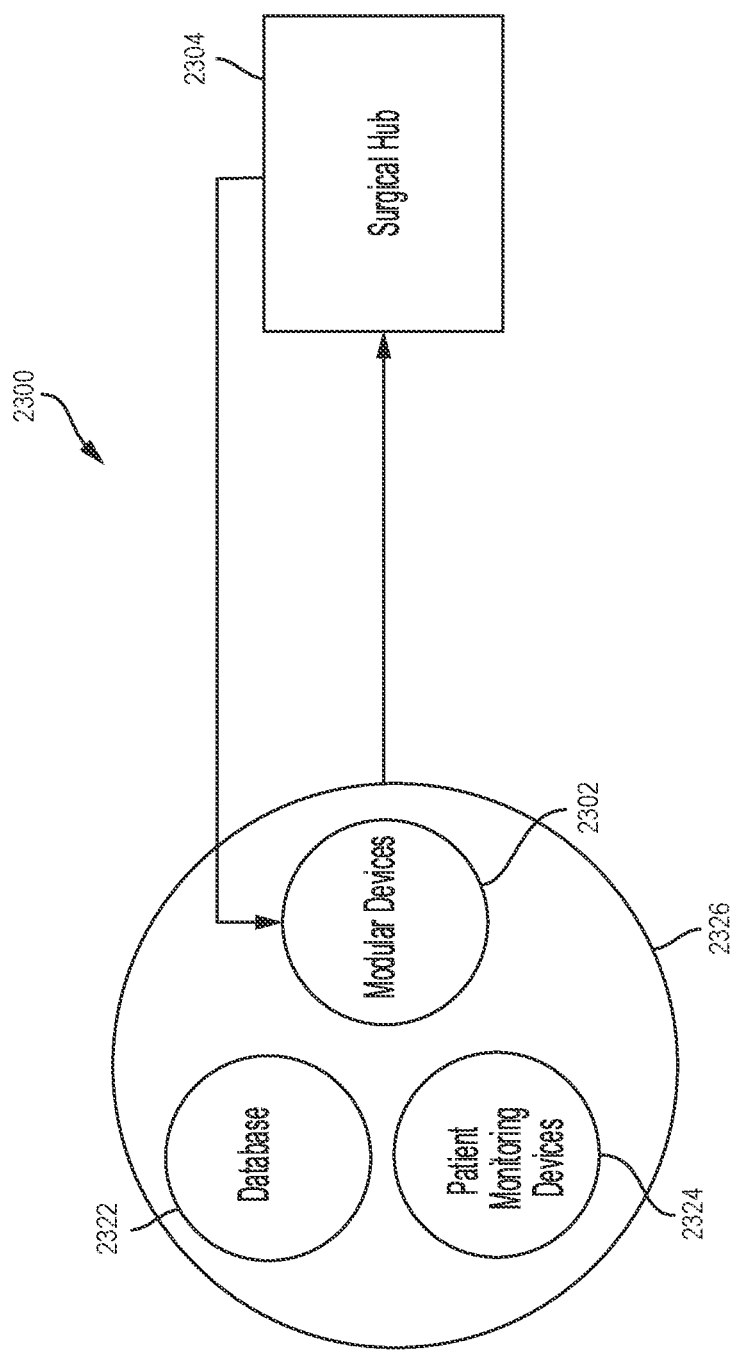
FIG. 5 is a diagram of a situationally aware surgical system, in accordance with at least one aspect of the present disclosure.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 5 illustrates a diagram of a situationally aware surgical system 2300, in accordance with at least one aspect of the present disclosure. In some exemplifications, the data sources 2326 include, for example, the modular devices 2302 (which can include sensors configured to detect parameters associated with the patient and/or the modular device itself), databases 2322 (e.g., an EMR database containing patient records), and patient monitoring devices 2324 (e.g., a blood pressure (BP) monitor and an electrocardiography (EKG) monitor). The surgical hub 2304 can be configured to derive the contextual information pertaining to the surgical procedure from the data based upon, for example, the particular combination(s) of received data or the particular order in which the data is received from the data sources 2326. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 2304 to derive or infer information related to the surgical procedure from received data can be referred to as "situational awareness." In one exemplification, the surgical hub 2304 can incorporate a situational awareness system, which is the hardware and/or programming associated with the surgical hub 2304 that derives contextual information pertaining to the surgical procedure from the received data.

The situational awareness system of the surgical hub 2304 can be configured to derive the contextual information from the data received from the data sources 2326 in a variety of different ways. In one exemplification, the situational awareness system includes a pattern recognition system, or machine learning system (e.g., an artificial neural network), that has been trained on training data to correlate various inputs (e.g., data from databases 2322, patient monitoring devices 2324, and/or modular devices 2302) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 2302. In one exemplification, the contextual information received by the situational awareness system of the surgical hub 2304 is associated with a particular control adjustment or set of control adjustments for one or more modular devices 2302. In another exemplification, the situational awareness system includes a further machine learning system, lookup table, or other such system, which generates or retrieves one or more control adjustments for one or more modular devices 2302 when provided the contextual information as input.

A surgical hub 2304 incorporating a situational awareness system provides a number of benefits for the surgical system 2300. One benefit includes improving the interpretation of sensed and collected data, which would in turn improve the processing accuracy and/or the usage of the data during the course of a surgical procedure. To return to a previous example, a situationally aware surgical hub 2304 could determine what type of tissue was being operated on; therefore, when an unexpectedly high force to close the surgical instrument's end effector is detected, the situationally aware surgical hub 2304 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 2304 could infer whether a surgical procedure being performed is a thoracic or an abdominal procedure, allowing the surgical hub 2304 to determine whether the tissue clamped by an end effector of the surgical stapling and cutting instrument is lung (for a thoracic procedure) or stomach (for an abdominal procedure) tissue. The surgical hub 2304 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 2304 could determine whether the surgical site is under pressure (by determining that the surgical procedure is utilizing insufflation) and determine the procedure type. As a procedure type is generally performed in a specific body cavity, the surgical hub 2304 could then control the motor rate of the smoke evacuator appropriately for the body cavity being operated in. Thus, a situationally aware surgical hub 2304 could provide a consistent amount of smoke evacuation for both thoracic and abdominal procedures.

As yet another example, the type of procedure being performed can affect the optimal energy level at which an ultrasonic surgical instrument or radio frequency (RF) electrosurgical instrument operates. Arthroscopic procedures, for example, require higher energy levels because the end effector of the ultrasonic surgical instrument or RF electrosurgical instrument is immersed in fluid. A situationally aware surgical hub 2304 could determine whether the surgical procedure is an arthroscopic procedure. The surgical hub 2304 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 2304 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 2304 can be configured to adjust the energy level for the ultrasonic surgical instrument or RF electrosurgical instrument throughout the course of a surgical procedure, rather than just on a procedure-by-procedure basis. A situationally aware surgical hub 2304 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 2326 to improve the conclusions that the surgical hub 2304 draws from one data source 2326. A situationally aware surgical hub 2304 could augment data that it receives from the modular devices 2302 with contextual information that it has built up regarding the surgical procedure from other data sources 2326. For example, a situationally aware surgical hub 2304 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 2304 can be further configured to compare a physiologic measurement (e.g., blood pressure sensed by a BP monitor communicably connected to the surgical hub 2304) with the visual or image data of hemostasis (e.g., from a medical imaging device 124 (FIG. 2) communicably coupled to the surgical hub 2304) to make a determination on the integrity of the staple line or tissue weld. In other words, the situational awareness system of the surgical hub 2304 can consider the physiological measurement data to provide additional context in analyzing the visualization data. The additional context can be useful when the visualization data may be inconclusive or incomplete on its own.

Another benefit includes proactively and automatically controlling the paired modular devices 2302 according to the particular step of the surgical procedure that is being performed to reduce the number of times that medical personnel are required to interact with or control the surgical system 2300 during the course of a surgical procedure. For example, a situationally aware surgical hub 2304 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 2304 could determine whether the current or subsequent step of the surgical procedure requires a different view or degree of magnification on the display according to the feature(s) at the surgical site that the surgeon is expected to need to view. The surgical hub 2304 could then proactively change the displayed view (supplied by, e.g., a medical imaging device for the visualization system 108) accordingly so that the display automatically adjusts throughout the surgical procedure.

As yet another example, a situationally aware surgical hub 2304 could determine which step of the surgical procedure is being performed or will subsequently be performed and whether particular data or comparisons between data will be required for that step of the surgical procedure. The surgical hub 2304 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 2304 could determine whether the operating theater is setup properly or optimally for the surgical procedure to be performed. The surgical hub 2304 can be configured to determine the type of surgical procedure being performed, retrieve the corresponding checklists, product location, or setup needs (e.g., from a memory), and then compare the current operating theater layout to the standard layout for the type of surgical procedure that the surgical hub 2304 determines is being performed. In one exemplification, the surgical hub 2304 can be configured to compare the list of items for the procedure (scanned by a scanner, for example) and/or a list of devices paired with the surgical hub 2304 to a recommended or anticipated manifest of items and/or devices for the given surgical procedure. If there are any discontinuities between the lists, the surgical hub 2304 can be configured to provide an alert indicating that a particular modular device 2302, patient monitoring device 2324, and/or other surgical item is missing. In one exemplification, the surgical hub 2304 can be configured to determine the relative distance or position of the modular devices 2302 and patient monitoring devices 2324 via proximity sensors, for example. The surgical hub 2304 can compare the relative positions of the devices to a recommended or anticipated layout for the particular surgical procedure. If there are any discontinuities between the layouts, the surgical hub 2304 can be configured to provide an alert indicating that the current layout for the surgical procedure deviates from the recommended layout.

As another example, a situationally aware surgical hub 2304 could determine whether the surgeon (or other medical personnel) was making an error or otherwise deviating from the expected course of action during the course of a surgical procedure. For example, the surgical hub 2304 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 2304 determined is being performed. In one exemplification, the surgical hub 2304 can be configured to provide an alert indicating that an unexpected action is being performed or an unexpected device is being utilized at the particular step in the surgical procedure.

Overall, the situational awareness system for the surgical hub 2304 improves surgical procedure outcomes by adjusting the surgical instruments (and other modular devices 2302) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 2302 in the surgical theater according to the specific context of the procedure.

Modular Energy System

ORs everywhere in the world are a tangled web of cords, devices, and people due to the amount of equipment required to perform surgical procedures. Surgical capital equipment tends to be a major contributor to this issue because most surgical capital equipment performs a single, specialized task. Due to their specialized nature and the surgeons' needs to utilize multiple different types of devices during the course of a single surgical procedure, an OR may be forced to be stocked with two or even more pieces of surgical capital equipment, such as energy generators. Each of these pieces of surgical capital equipment may need to be individually plugged into a power source and may be connected to one or more other devices that are being passed between OR personnel, creating a tangle of cords that have to be navigated. Another issue faced in modern ORs is that each of these specialized pieces of surgical capital equipment has its own user interface and needs to be independently controlled from the other pieces of equipment within the OR. This creates complexity in properly controlling multiple different devices in connection with each other and forces users to be trained on and memorize different types of user interfaces (which may further change based upon the task or surgical procedure being performed, in addition to changing between each piece of capital equipment). This cumbersome, complex process can necessitate the need for even more individuals to be present within the OR and can create danger if multiple devices are not properly controlled in tandem with each other. Therefore, consolidating surgical capital equipment technology into singular systems that are able to flexibly address surgeons' needs to reduce the footprint of surgical capital equipment within ORs would simplify the user experience, reduce the amount of clutter in ORs, and prevent difficulties and dangers associated with simultaneously controlling multiple pieces of capital equipment. Further, making such systems expandable or customizable would allow for new technology to be conveniently incorporated into existing surgical systems, obviating the need to replace entire surgical systems or for OR personnel to learn new user interfaces or equipment controls with each new technology.

As described in FIGS. 1-3, a surgical hub 106 can be configured to interchangeably receive a variety of modules, which can in turn interface with surgical devices (e.g., a surgical instrument or a smoke evacuator) or provide various other functions (e.g., communications). In one aspect, a surgical hub 106 can be embodied as a modular energy system 2000, which is illustrated in connection with FIGS. 6-12. The modular energy system 2000 can include a variety of different modules 2001 that are connectable together in a stacked configuration. In one aspect, the modules 2001 can be both physically and communicably coupled together when stacked or otherwise connected together into a singular assembly. Further, the modules 2001 can be interchangeably connectable together in different combinations or arrangements. In one aspect, each of the modules 2001 can include a consistent or universal array of connectors disposed along their upper and lower surfaces, thereby allowing any module 2001 to be connected to another module 2001 in any arrangement (except that, in some aspects, a particular module type, such as the header module 2002, can be configured to serve as the uppermost module within the stack, for example). In an alternative aspect, the modular energy system 2000 can include a housing that is configured to receive and retain the modules 2001, as is shown in FIG. 3. The modular energy system 2000 can also include a variety of different components or accessories that are also connectable to or otherwise associatable with the modules 2001. In another aspect, the modular energy system 2000 can be embodied as a generator module 140 (FIG. 3) of a surgical hub 106. In yet another aspect, the modular energy system 2000 can be a distinct system from a surgical hub 106. In such aspects, the modular energy system 2000 can be communicably couplable to a surgical hub 206 for transmitting and/or receiving data therebetween.

Figure 6:
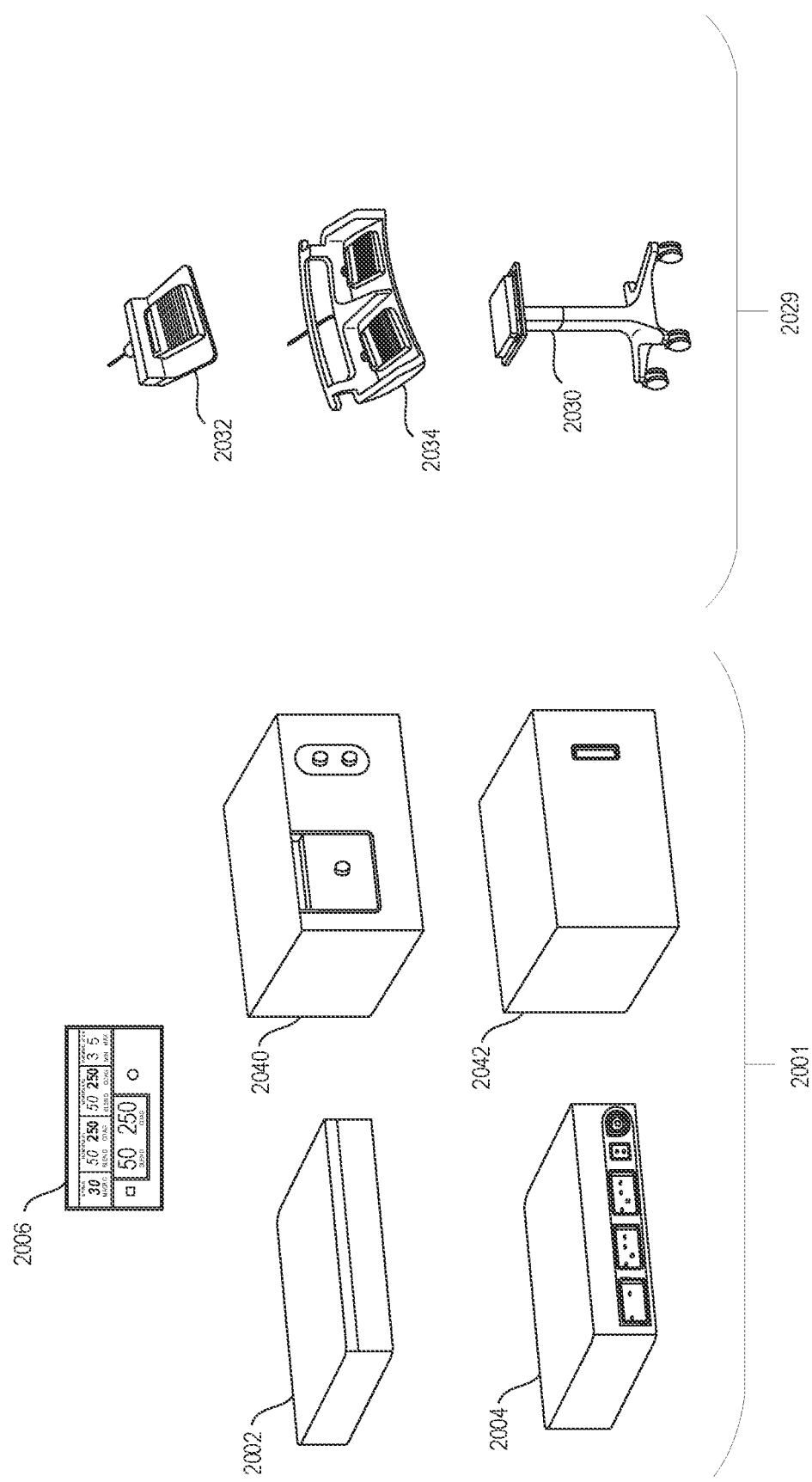
FIG. 6 is a diagram of various modules and other components that are combinable to customize modular energy systems, in accordance with at least one aspect of the present disclosure.

The modular energy system 2000 can be assembled from a variety of different modules 2001, some examples of which are illustrated in FIG. 6. Each of the different types of modules 2001 can provide different functionality, thereby allowing the modular energy system 2000 to be assembled into different configurations to customize the functions and capabilities of the modular energy system 2000 by customizing the modules 2001 that are included in each modular energy system 2000. The modules 2001 of the modular energy system 2000 can include, for example, a header module 2002 (which can include a display screen 2006), an energy module 2004, a technology module 2040, and a visualization module 2042. In the depicted aspect, the header module 2002 is configured to serve as the top or uppermost module within the modular energy system stack and can thus lack connectors along its top surface. In another aspect, the header module 2002 can be configured to be positioned at the bottom or the lowermost module within the modular energy system stack and can thus lack connectors along its bottom surface. In yet another aspect, the header module 2002 can be configured to be positioned at an intermediate position within the modular energy system stack and can thus include connectors along both its bottom and top surfaces. The header module 2002 can be configured to control the system-wide settings of each module 2001 and component connected thereto through physical controls 2011 thereon and/or a graphical user interface (GUI) 2008 rendered on the display screen 2006. Such settings could include the activation of the modular energy system 2000, the volume of alerts, the footswitch settings, the settings icons, the appearance or configuration of the user interface, the surgeon profile logged into the modular energy system 2000, and/or the type of surgical procedure being performed. The header module 2002 can also be configured to provide communications, processing, and/or power for the modules 2001 that are connected to the header module 2002. The energy module 2004, which can also be referred to as a generator module 140 (FIG. 3), can be configured to generate one or multiple energy modalities for driving electrosurgical and/or ultrasonic surgical instruments connected thereto. The technology module 2040 can be configured to provide additional or expanded control algorithms (e.g., electrosurgical or ultrasonic control algorithms for controlling the energy output of the energy module 2004). The visualization module 2042 can be configured to interface with visualization devices (i.e., scopes) and accordingly provide increased visualization capabilities.

The modular energy system 2000 can further include a variety of accessories 2029 that are connectable to the modules 2001 for controlling the functions thereof or that are otherwise configured to work on conjunction with the modular energy system 2000. The accessories 2029 can include, for example, a single-pedal footswitch 2032, a dual-pedal footswitch 2034, and a cart 2030 for supporting the modular energy system 2000 thereon. The footswitches 2032,2034 can be configured to control the activation or function of particular energy modalities output by the energy module 2004, for example.

By utilizing modular components, the depicted modular energy system 2000 provides a surgical platform that grows with the availability of technology and is customizable to the needs of the facility and/or surgeons. Further, the modular energy system 2000 supports combo devices (e.g., dual electrosurgical and ultrasonic energy generators) and supports software-driven algorithms for customized tissue effects. Still further, the surgical system architecture reduces the capital footprint by combining multiple technologies critical for surgery into a single system.

The various modular components utilizable in connection with the modular energy system 2000 can include monopolar energy generators, bipolar energy generators, dual electrosurgical/ultrasonic energy generators, display screens, and various other modules and/or other components, some of which are also described above in connection with FIGS. 1-3.

Figure 11:
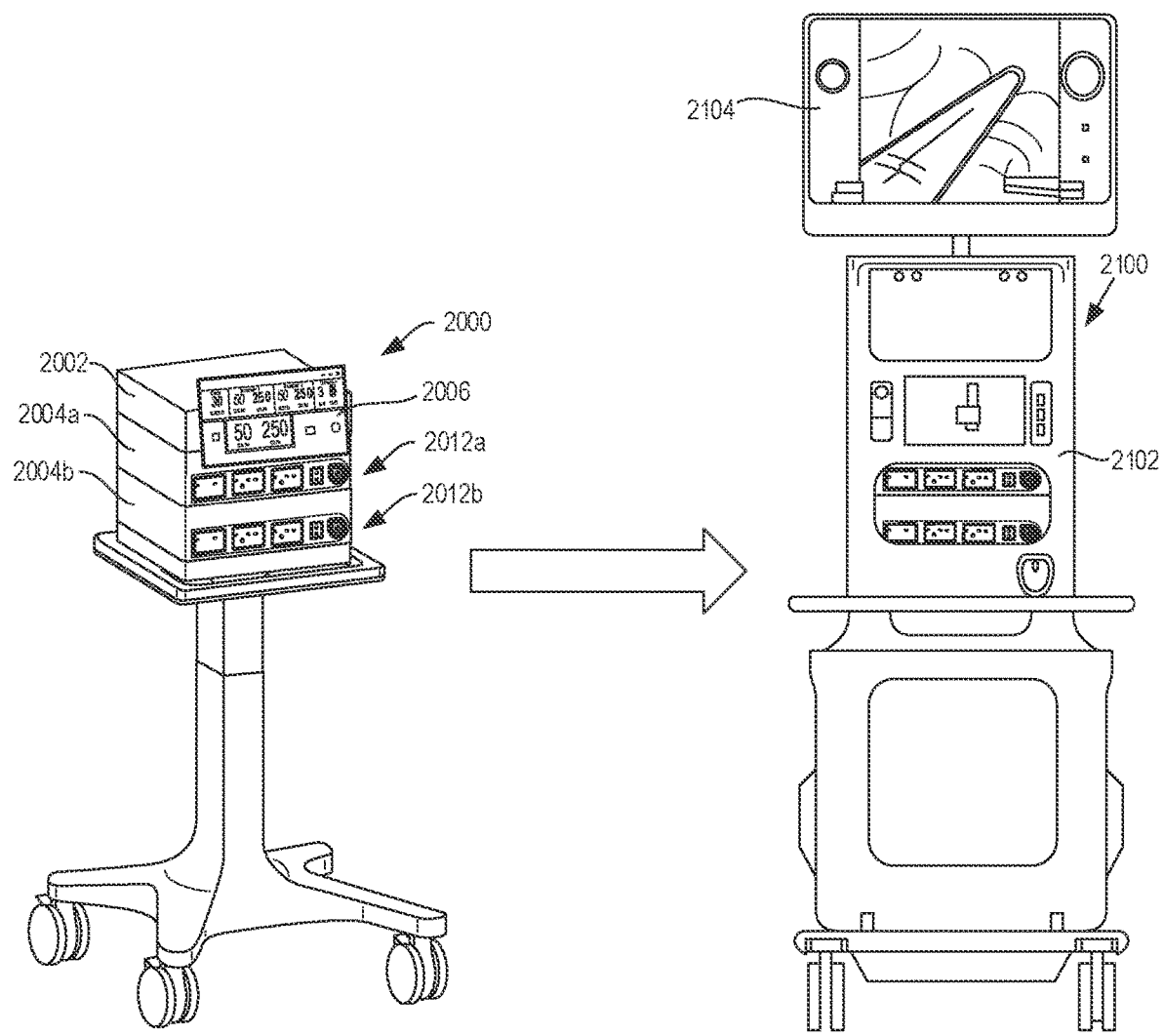
FIG. 11 is a diagram of a modular energy system including communicably connectable surgical platforms, in accordance with at least one aspect of the present disclosure.

Referring now to FIG. 7A, the header module 2002 can, in some aspects, include a display screen 2006 that renders a GUI 2008 for relaying information regarding the modules 2001 connected to the header module 2002. In some aspects, the GUI 2008 of the display screen 2006 can provide a consolidated point of control of all of the modules 2001 making up the particular configuration of the modular energy system 2000. Various aspects of the GUI 2008 are discussed in fuller detail below in connection with FIG. 12. In alternative aspects, the header module 2002 can lack the display screen 2006 or the display screen 2006 can be detachably connected to the housing 2010 of the header module 2002. In such aspects, the header module 2002 can be communicably couplable to an external system that is configured to display the information generated by the modules 2001 of the modular energy system 2000. For example, in robotic surgical applications, the modular energy system 2000 can be communicably couplable to a robotic cart or robotic control console, which is configured to display the information generated by the modular energy system 2000 to the operator of the robotic surgical system. As another example, the modular energy system 2000 can be communicably couplable to a mobile display that can be carried or secured to a surgical staff member for viewing thereby. In yet another example, the modular energy system 2000 can be communicably couplable to a surgical hub 2100 or another computer system that can include a display 2104, as is illustrated in FIG. 11. In aspects utilizing a user interface that is separate from or otherwise distinct from the modular energy system 2000, the user interface can be wirelessly connectable with the modular energy system 2000 as a whole or one or more modules 2001 thereof such that the user interface can display information from the connected modules 2001 thereon.

Referring still to FIG. 7A, the energy module 2004 can include a port assembly 2012 including a number of different ports configured to deliver different energy modalities to corresponding surgical instruments that are connectable thereto. In the particular aspect illustrated in FIGS. 6-12, the port assembly 2012 includes a bipolar port 2014, a first monopolar port 2016*a*, a second monopolar port 2016*b*, a neutral electrode port 2018 (to which a monopolar return pad is connectable), and a combination energy port 2020. However, this particular combination of ports is simply provided for illustrative purposes and alternative combinations of ports and/or energy modalities may be possible for the port assembly 2012.

As noted above, the modular energy system 2000 can be assembled into different configurations. Further, the different configurations of the modular energy system 2000 can also be utilizable for different surgical procedure types and/or different tasks. For example, FIGS. 7A and 7B illustrate a first illustrative configuration of the modular energy system 2000 including a header module 2002 (including a display screen 2006) and an energy module 2004 connected together. Such a configuration can be suitable for laparoscopic and open surgical procedures, for example.

Figure 8A:
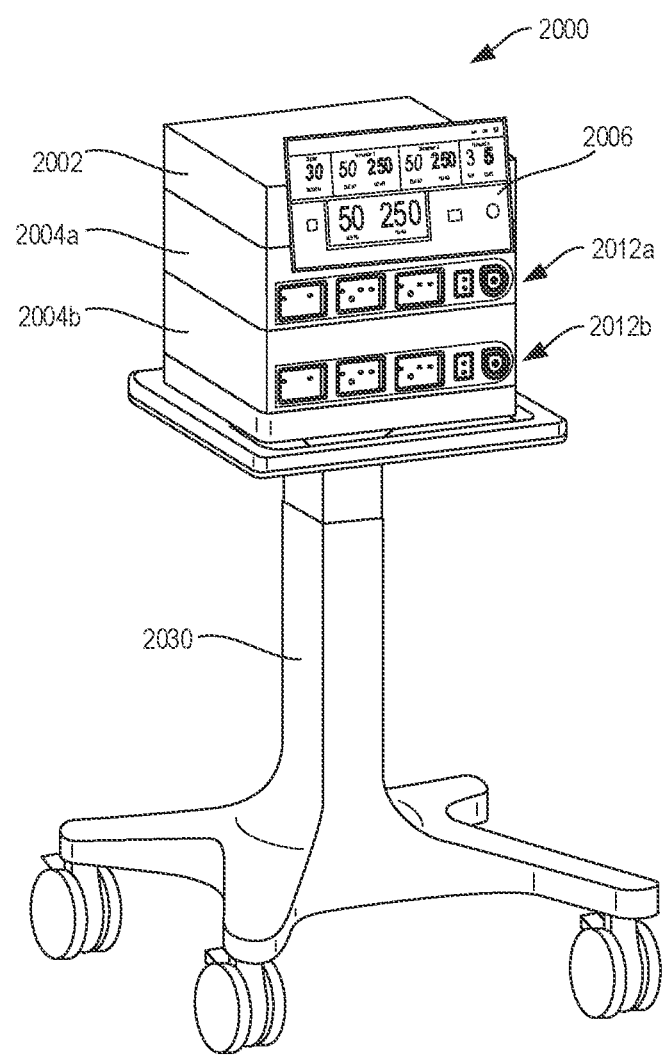
FIG. 8A is a second illustrative modular energy system configuration including a header module, a display screen, an energy module, and an expanded energy module connected together and mounted to a cart, in accordance with at least one aspect of the present disclosure.
Figure 8B:
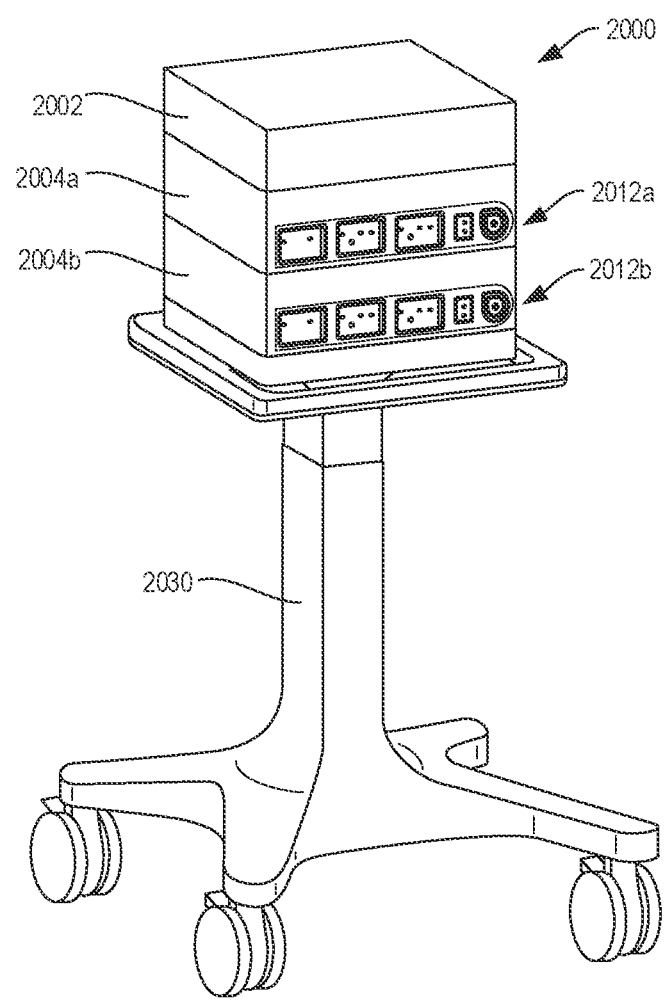
FIG. 8B is a third illustrative modular energy system configuration that is similar to the second configuration shown in FIG. 7A, except that the header module lacks a display screen, in accordance with at least one aspect of the present disclosure.

FIG. 8A illustrates a second illustrative configuration of the modular energy system 2000 including a header module 2002 (including a display screen 2006), a first energy module 2004*a*, and a second energy module 2004*b* connected together. By stacking two energy modules 2004*a*, 2004*b*, the modular energy system 2000 can provide a pair of port assemblies 2012*a*, 2012*b* for expanding the array of energy modalities deliverable by the modular energy system 2000 from the first configuration. The second configuration of the modular energy system 2000 can accordingly accommodate more than one bipolar/monopolar electrosurgical instrument, more than two bipolar/monopolar electrosurgical instruments, and so on. Such a configuration can be suitable for particularly complex laparoscopic and open surgical procedures. FIG. 8B illustrates a third illustrative configuration that is similar to the second configuration, except that the header module 2002 lacks a display screen 2006. This configuration can be suitable for robotic surgical applications or mobile display applications, as noted above.

Figure 9:
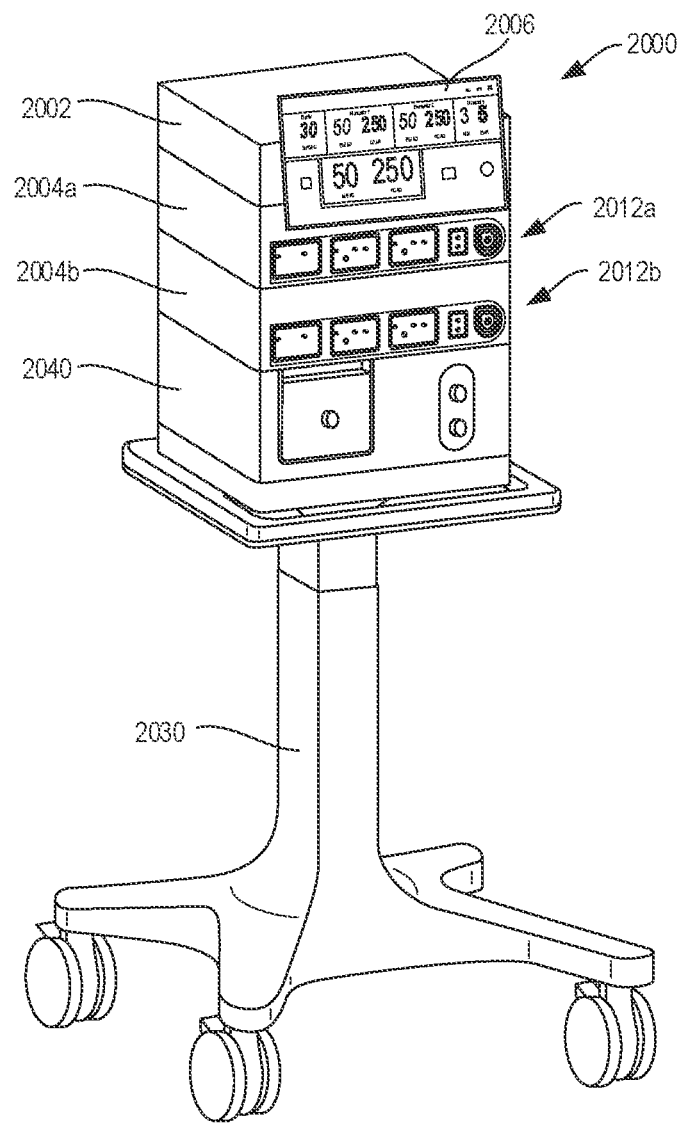
FIG. 9 is a fourth illustrative modular energy system configuration including a header module, a display screen, an energy module, ae expanded energy module, and a technology module connected together and mounted to a cart, in accordance with at least one aspect of the present disclosure.

FIG. 9 illustrates a fourth illustrative configuration of the modular energy system 2000 including a header module 2002 (including a display screen 2006), a first energy module 2004*a*, a second energy module 2004*b*, and a technology module 2040 connected together. Such a configuration can be suitable for surgical applications where particularly complex or computation-intensive control algorithms are required. Alternatively, the technology module 2040 can be a newly released module that supplements or expands the capabilities of previously released modules (such as the energy module 2004).

Figure 10:
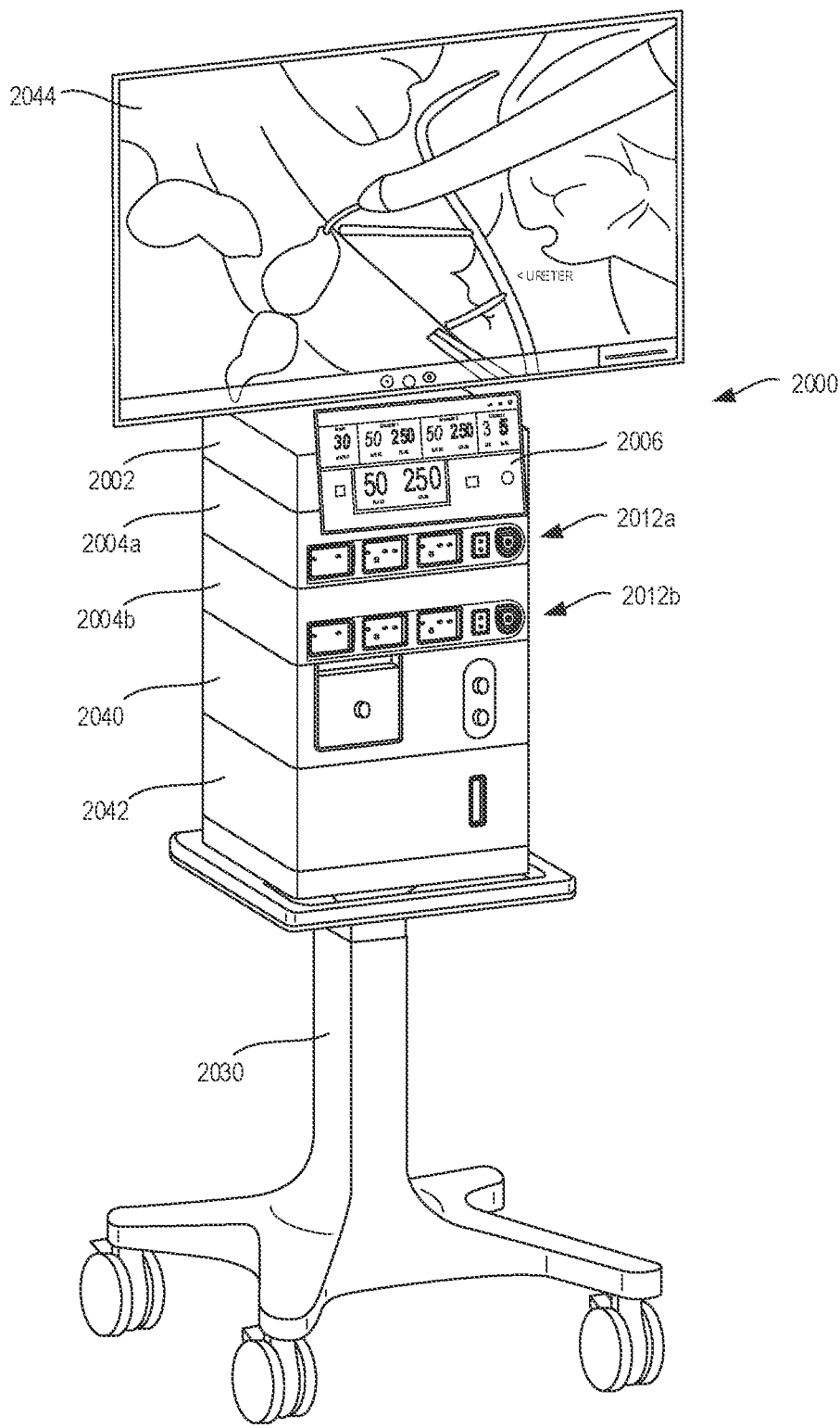
FIG. 10 is a fifth illustrative modular energy system configuration including a header module, a display screen, an energy module, an expanded energy module, a technology module, and a visualization module connected together and mounted to a cart, in accordance with at least one aspect of the present disclosure.

FIG. 10 illustrates a fifth illustrative configuration of the modular energy system 2000 including a header module 2002 (including a display screen 2006), a first energy module 2004*a*, a second energy module 2004*b*, a technology module 2040, and a visualization module 2042 connected together. Such a configuration can be suitable for endoscopic procedures by providing a dedicated surgical display 2044 for relaying the video feed from the scope coupled to the visualization module 2042. It should be noted that the configurations illustrated in FIGS. 7A-11 and described above are provided simply to illustrate the various concepts of the modular energy system 2000 and should not be interpreted to limit the modular energy system 2000 to the particular aforementioned configurations.

As noted above, the modular energy system 2000 can be communicably couplable to an external system, such as a surgical hub 2100 as illustrated in FIG. 11. Such external systems can include a display screen 2104 for displaying a visual feed from an endoscope (or a camera or another such visualization device) and/or data from the modular energy system 2000. Such external systems can also include a computer system 2102 for performing calculations or otherwise analyzing data generated or provided by the modular energy system 2000, controlling the functions or modes of the modular energy system 2000, and/or relaying data to a cloud computing system or another computer system. Such external systems could also coordinate actions between multiple modular energy systems 2000 and/or other surgical systems (e.g., a visualization system 108 and/or a robotic system 110 as described in connection with FIGS. 1 and 2).

Figure 12:
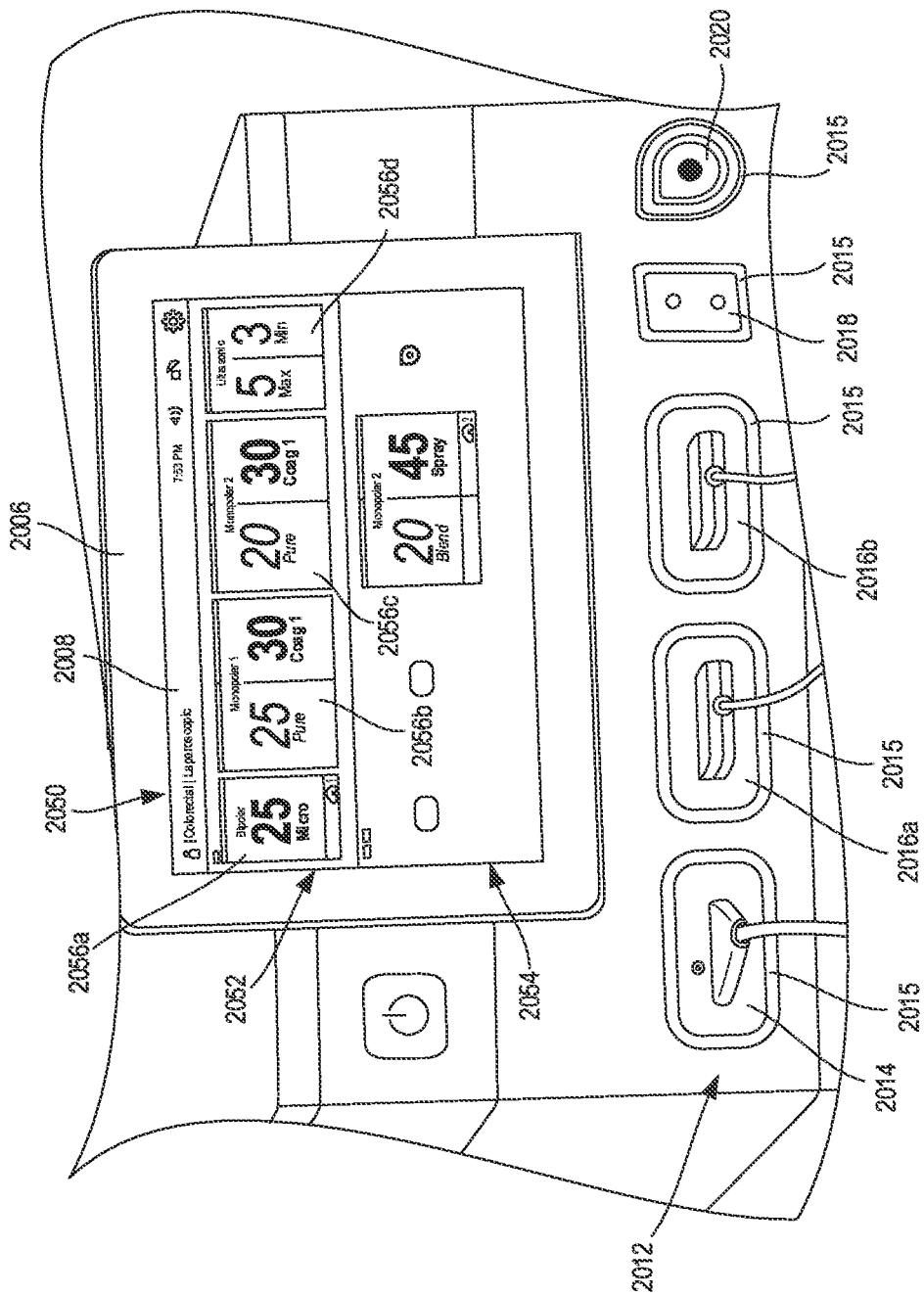
FIG. 12 is a perspective view of a header module of a modular energy system including a user interface, in accordance with at least one aspect of the present disclosure.

Referring now to FIG. 12, in some aspects, the header module 2002 can include or support a display 2006 configured for displaying a GUI 2008, as noted above. The display screen 2006 can include a touchscreen for receiving input from users in addition to displaying information. The controls displayed on the GUI 2008 can correspond to the module(s) 2001 that are connected to the header module 2002. In some aspects, different portions or areas of the GUI 2008 can correspond to particular modules 2001. For example, a first portion or area of the GUI 2008 can correspond to a first module and a second portion or area of the GUI 2008 can correspond to a second module. As different and/or additional modules 2001 are connected to the modular energy system stack, the GUI 2008 can adjust to accommodate the different and/or additional controls for each newly added module 2001 or remove controls for each module 2001 that is removed. Each portion of the display corresponding to a particular module connected to the header module 2002 can display controls, data, user prompts, and/or other information corresponding to that module. For example, in FIG. 12, a first or upper portion 2052 of the depicted GUI 2008 displays controls and data associated with an energy module 2004 that is connected to the header module 2002. In particular, the first portion 2052 of the GUI 2008 for the energy module 2004 provides first widget 2056a corresponding to the bipolar port 2014, a second widget 2056b corresponding to the first monopolar port 2016a, a third widget 2056c corresponding to the second monopolar port 2016b, and a fourth widget 2056d corresponding to the combination energy port 2020. Each of these widgets 2056a-d provides data related to its corresponding port of the port assembly 2012 and controls for controlling the modes and other features of the energy modality delivered by the energy module 2004 through the respective port of the port assembly 2012. For example, the widgets 2056a-d can be configured to display the power level of the surgical instrument connected to the respective port, change the operational mode of the surgical instrument connected to the respective port (e.g., change a surgical instrument from a first power level to a second power level and/or change a monopolar surgical instrument from a "spray" mode to a "blend" mode), and so on.

In one aspect, the header module 2002 can include various physical controls 2011 in addition to or in lieu of the GUI 2008. Such physical controls 2011 can include, for example, a power button that controls the application of power to each module 2001 that is connected to the header module 2002 in the modular energy system 2000. Alternatively, the power button can be displayed as part of the GUI 2008. Therefore, the header module 2002 can serve as a single point of contact and obviate the need to individually activate and deactivate each individual module 2001 from which the modular energy system 2000 is constructed.

In one aspect, the header module 2002 can display still images, videos, animations, and/or information associated with the surgical modules 2001 of which the modular energy system 2000 is constructed or the surgical devices that are communicably coupled to the modular energy system 2000. The still images and/or videos displayed by the header module 2002 can be received from an endoscope or another visualization device that is communicably coupled to the modular energy system 2000. The animations and/or information of the GUI 2008 can be overlaid on or displayed adjacent to the images or video feed.

In one aspect, the modules 2001 other than the header module 2002 can be configured to likewise relay information to users. For example, the energy module 2004 can include light assemblies 2015 disposed about each of the ports of the port assembly 2012. The light assemblies 2015 can be configured to relay information to the user regarding the port according to their color or state (e.g., flashing). For example, the light assemblies 2015 can change from a first color to a second color when a plug is fully seated within the respective port. In one aspect, the color or state of the light assemblies 2015 can be controlled by the header module 2002. For example, the header module 2002 can cause the light assembly 2015 of each port to display a color corresponding to the color display for the port on the GUI 2008.

Figure 13:
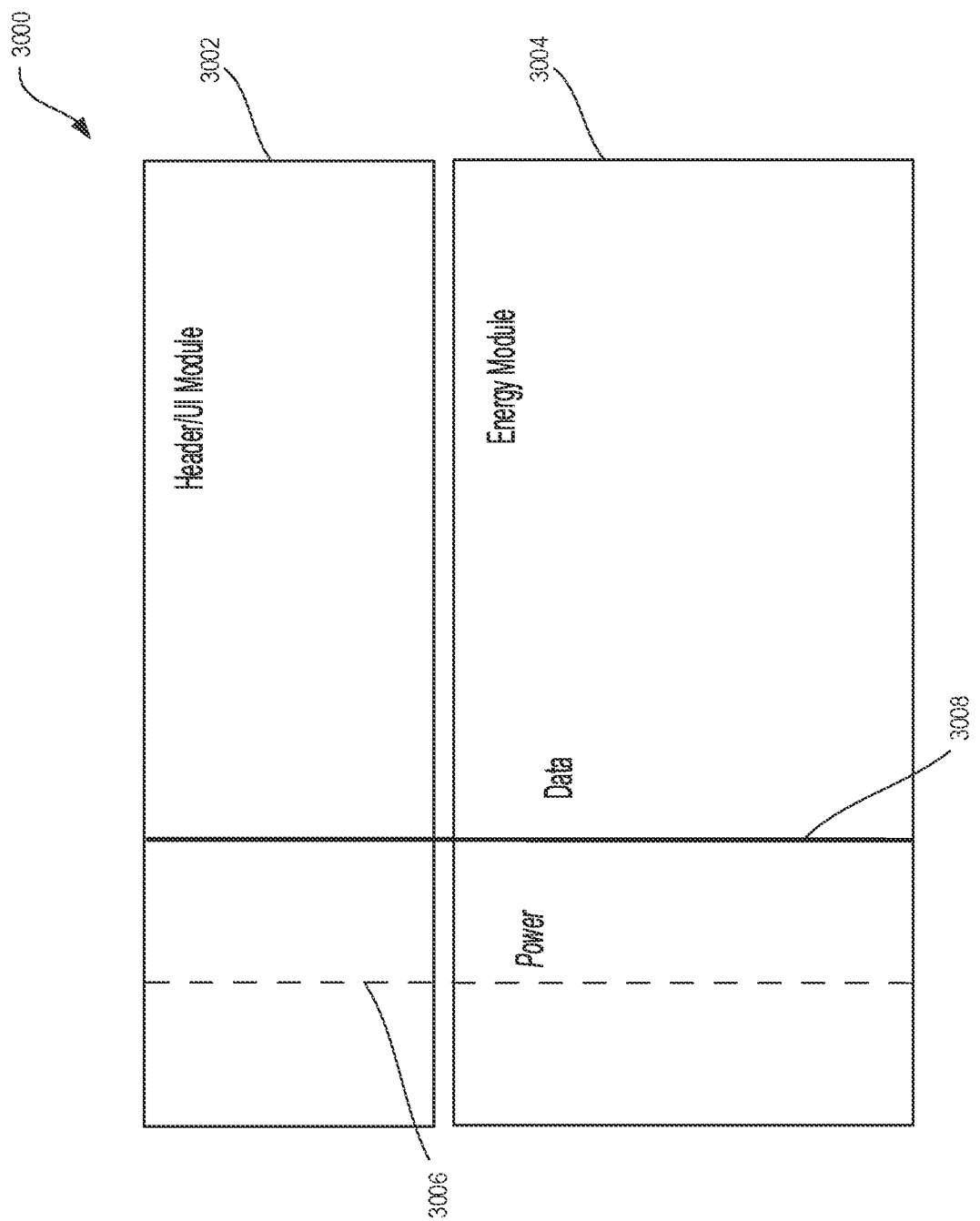
FIG. 13 is a block diagram of a stand-alone hub configuration of a modular energy system, in accordance with at least one aspect of the present disclosure.
Figure 14:
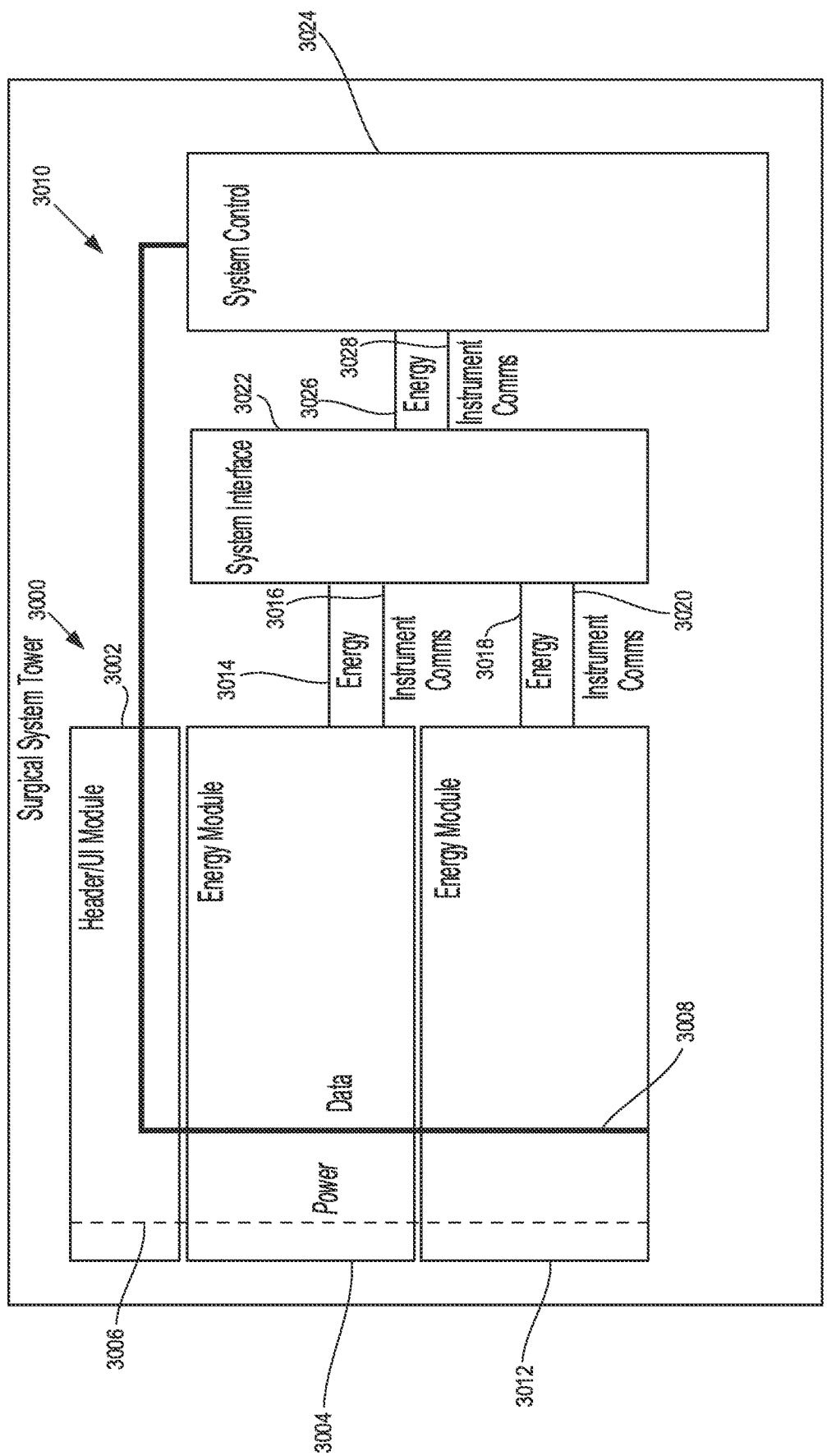
FIG. 14 is a block diagram of a hub configuration of a modular energy system integrated with a surgical control system, in accordance with at least one aspect of the present disclosure.

FIG. 13 is a block diagram of a stand-alone hub configuration of a modular energy system 3000, in accordance with at least one aspect of the present disclosure and FIG. 14 is a block diagram of a hub configuration of a modular energy system 3000 integrated with a surgical control system 3010, in accordance with at least one aspect of the present disclosure. As depicted in FIGS. 13 and 14, the modular energy system 3000 can be either utilized as stand-alone units or integrated with a surgical control system 3010 that controls and/or receives data from one or more surgical hub units. In the examples illustrated in FIGS. 13 and 14, the integrated header/UI module 3002 of the modular energy system 3000 includes a header module and a UI module integrated together as a singular module. In other aspects, the header module and the UI module can be provided as separate components that are communicatively coupled though a data bus 3008.

As illustrated in FIG. 13, an example of a stand-alone modular energy system 3000 includes an integrated header module/user interface (UI) module 3002 coupled to an energy module 3004. Power and data are transmitted between the integrated header/UI module 3002 and the energy module 3004 through a power interface 3006 and a data interface 3008. For example, the integrated header/UI module 3002 can transmit various commands to the energy module 3004 through the data interface 3008. Such commands can be based on user inputs from the UI. As a further example, power may be transmitted to the energy module 3004 through the power interface 3006.

In FIG. 14, a surgical hub configuration includes a modular energy system 3000 integrated with a control system 3010 and an interface system 3022 for managing, among other things, data and power transmission to and/or from the modular energy system 3000. The modular energy system depicted in FIG. 14 includes an integrated header module/UI module 3002, a first energy module 3004, and a second energy module 3012. In one example, a data transmission pathway is established between the system control unit 3024 of the control system 3010 and the second energy module 3012 through the first energy module 3004 and the header/UI module 3002 through a data interface 3008. In addition, a power pathway extends between the integrated header/UI module 3002 and the second energy module 3012 through the first energy module 3004 through a power interface 3006. In other words, in one aspect, the first energy module 3004 is configured to function as a power and data interface between the second energy module 3012 and the integrated header/UI module 3002 through the power interface 3006 and the data interface 3008. This arrangement allows the modular energy system 3000 to expand by seamlessly connecting additional energy modules to energy modules 3004, 3012 that are already connected to the integrated header/UI module 3002 without the need for dedicated power and energy interfaces within the integrated header/UI module 3002.

The system control unit 3024, which may be referred to herein as a control circuit, control logic, microprocessor, microcontroller, logic, or FPGA, or various combinations thereof, is coupled to the system interface 3022 via energy interface 3026 and instrument communication interface 3028. The system interface 3022 is coupled to the first energy module 3004 via a first energy interface 3014 and a first instrument communication interface 3016. The system interface 3022 is coupled to the second energy module 3012 via a second energy interface 3018 and a second instrument communication interface 3020. As additional modules, such as additional energy modules, are stacked in the modular energy system 3000, additional energy and communications interfaces are provided between the system interface 3022 and the additional modules.

The energy modules 3004, 3012 are connectable to a hub and can be configured to generate electrosurgical energy (e.g., bipolar or monopolar), ultrasonic energy, or a combination thereof (referred to herein as an "advanced energy" module) for a variety of energy surgical instruments. Generally, the energy modules 3004, 3012 include hardware/software interfaces, an ultrasonic controller, an advanced energy RF controller, bipolar RF controller, and control algorithms executed by the controller that receives outputs from the controller and controls the operation of the various energy modules 3004, 3012 accordingly. In various aspects of the present disclosure, the controllers described herein may be implemented as a control circuit, control logic, microprocessor, microcontroller, logic, or FPGA, or various combinations thereof.

In one aspect, with reference to FIGS. 13 and 14, the modules of the modular energy system 3000 can include an optical link allowing high speed communication (10-50 Mb/s) across the patient isolation boundary. This link would carry device communications, mitigation signals (watchdog, etc.), and low bandwidth run-time data. In some aspects, the optical link(s) will not contain real-time sampled data, which can be done on the non-isolated side.

In one aspect, with reference to FIGS. 13 and 14, the modules of the modular energy system 3000 can include a multi-function circuit block which can: (i) read presence resistor values via A/D and current source, (ii) communicate with legacy instruments via hand switch Q protocols, (iii) communicate with instruments via local bus 1-Wire protocols, and (iv) communicate with CAN FD-enabled surgical instruments. When a surgical instrument is properly identified by an energy generator module, the relevant pin functions and communications circuits are enabled, while the other unused functions are disabled or disconnected, and set to a high impedance state.

In one aspect, with reference to FIGS. 13 and 14, the modules of the modular energy system 3000 can include a pulse/stimulation/auxiliary amplifier. This is a flexible-use amplifier based on a full-bridge output and incorporates functional isolation. This allows its differential output to be referenced to any output connection on the applied part (except, in some aspects, a monopolar active electrode). The amplifier output can be either small signal linear (pulse/stim) with waveform drive provided by a DAC or a square wave drive at moderate output power for DC applications such as DC motors, illumination, FET drive, etc. The output voltage and current are sensed with functionally isolated voltage and current feedback to provide accurate impedance and power measurements to the FPGA. Paired with a CAN FD-enabled instrument, this output can offer motor/motion control drive, while position or velocity feedback is provided by the CAN FD interface for closed loop control.

As described in greater detail herein, a modular energy system comprises a header module and one or more functional or surgical modules. In various instances, the modular energy system is a modular energy system. In various instances, the surgical modules include energy modules, communication modules, user interface modules; however, the surgical modules are envisioned to be any suitable type of functional or surgical module for use with the modular energy system.

Figure 15:
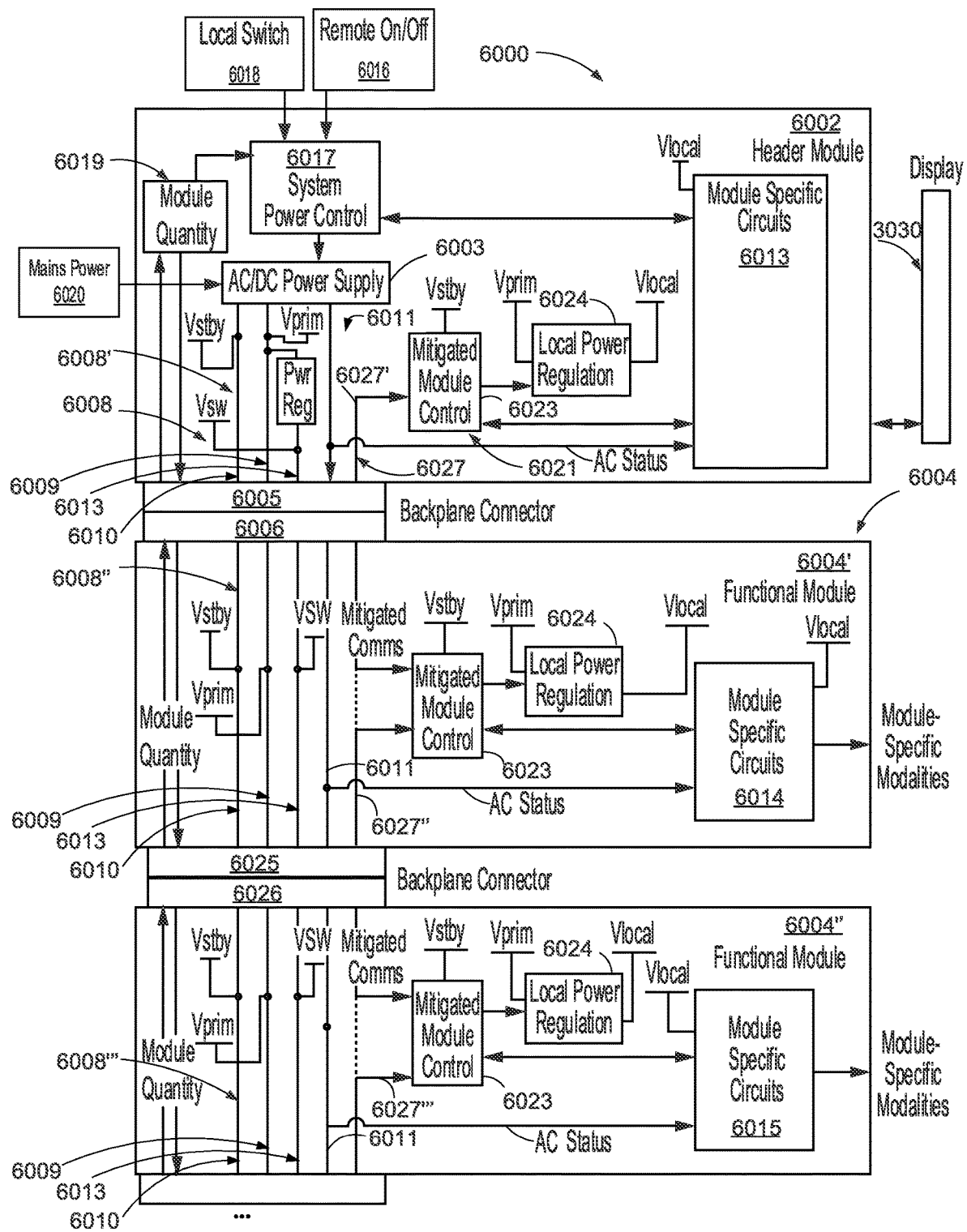
FIG. 15 is a schematic diagram of a modular energy system stack illustrating a power backplane, in accordance with at least one aspect of the present disclosure.

Modular energy system offers many advantages in a surgical procedure, as described above in connection with the modular energy systems 2000 (FIGS. 6-12), 3000 (FIGS. 13-15). However, cable management and setup/teardown time can be a significant deterrent. Various aspects of the present disclosure provide a modular energy system with a single power cable and a single power switch to control startup and shutdown of the entire modular energy system, which obviated the need to individually activate and deactivate each individual module from which the modular energy system is constructed. Also, various aspects of the present disclosure provide a modular energy system with power management schemes that facilitate a safe and, in some instances, concurrent delivery of power to the modules of a modular energy system.

In various aspects, as illustrated in FIG. 15, a modular energy system 6000 that is similar in many respects to the modular energy systems 2000 (FIGS. 6-12), 3000 (FIGS. 13-15). For the sake of brevity, various details of the modular energy system 6000, which are similar to the modular energy system 2000 and/or the modular energy system 3000, are not repeated herein.

The modular energy system 6000 comprises a header module 6002 and an "N" number of surgical modules 6004, where "N" is an integer greater than or equal to one. In various examples, the modular energy system 6000 includes a UI module such as, for example, the UI module 3030 and/or a communication module such as, for example, the communication module 3032. Furthermore, pass-through hub connectors couple individual modules to one another in a stack configuration. In the example of FIG. 15, the header module 6002 is coupled to a surgical module 6004 via pass-through hub connectors 6005, 6006.

The modular energy system 6000 comprises an example power architecture that consists of a single AC/DC power supply 6003 that provides power to all the surgical modules in the stack. The AC/DC power supply 6003 is housed in the header module 6002, and utilizes a power backplane 6008 to distribute power to each module in the stack. The example of FIG. 15 demonstrates three separate power domains on the power backplane 6008: a primary power domain 6009, a standby power domain 6010, and an Ethernet switch power domain 6013.

In the example illustrated in FIG. 15, the power backplane 6008 extends from the header module 6002 through a number of intermediate modules 6004 to a most bottom, or farthest, module in the stack. In various aspects, the power backplane 6008 is configured to deliver power to a surgical module 6004 through one or more other surgical modules 6004 that are ahead of it in the stack. The surgical module 6004 receiving power from the header module 6002 can be coupled to a surgical instrument or tool configured to deliver therapeutic energy to a patient.

The primary power domain 6009 is the primary power source for the functional module-specific circuits 6013, 6014, 6015 of the modules 6002, 6004. It consists of a single voltage rail that is provided to every module. In at least one example, a nominal voltage of 60V can be selected to be higher than the local rails needed by any module, so that the modules can exclusively implement buck regulation, which is generally more efficient than boost regulation.

In various aspects, the primary power domain 6009 is controlled by the header module 6002. In certain instances, as illustrated in FIG. 15, a local power switch 6018 is positioned on the header module 6002. In certain instances, a remote on/off interface 6016 can be configured to control a system power control 6017 on the header module 6002, for example. In at least one example, the remote on/off interface 6016 is configured to transmit pulsed discrete commands (separate commands for On and Off) and a power status telemetry signal. In various instances, the primary power domain 6009 is configured to distribute power to all the modules in the stack configuration following a user-initiated power-up.

Figure 16:
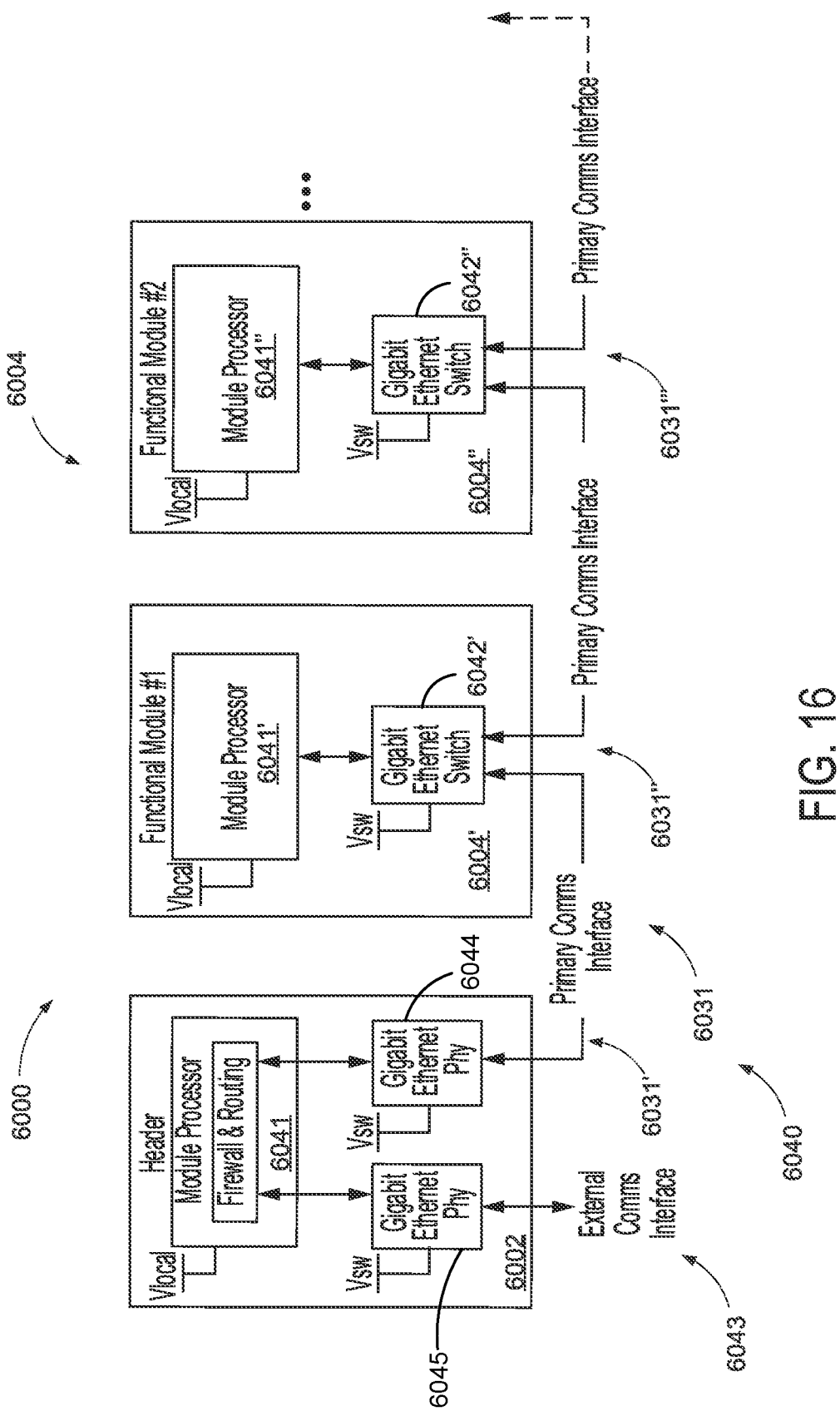
FIG. 16 is a schematic diagram of a modular energy system, in accordance with at least one aspect of the present disclosure.

In various aspects, as illustrated in FIG. 16, the modules of the modular energy system 6000 can be communicably coupled to the header module 6002 and/or to each other via a communication (Serial bus/Ethernet) interface 6040 such that data or other information is shared by and between the modules of which the modular energy system is constructed. An Ethernet switch domain 6013 can be derived from the primary power domain 6009, for example. The Ethernet switch power domain 6013 is segregated into a separate power domain, which is configured to power Ethernet switches within each of the modules in the stack configuration, so that the primary communications interface 6040 will remain alive when local power to a module is removed. In at least one example, the primary communication interface 6040 comprises a 1000BASE-T Ethernet network, where each module represents a node on the network, and each module downstream from the header module 6002 contains a 3-port Ethernet switch for routing traffic to the local module or passing the data up or downstream as appropriate.

Furthermore, in certain examples, the modular energy system 6000 includes secondary, low speed, communication interface between modules for critical, power related functions including module power sequencing and module power status. The secondary communications interface can, for example, be a multi-drop Local Interconnect Network (LIN), where the header module is the master and all downstream modules are slaves.

In various aspects, as illustrated in FIG. 15, a standby power domain 6010 is a separate output from the AC/DC power supply 6003 that is always live when the supply is connected to mains power 6020. The standby power domain 6010 is used by all the modules in the system to power circuitry for a mitigated communications interface, and to control the local power to each module. Further, the standby power domain 6010 is configured to provide power to circuitry that is critical in a standby mode such as, for example, on/off command detection, status LEDs, secondary communication bus, etc.

In various aspects, as illustrated in FIG. 15, the individual surgical modules 6004 lack independent power supplies and, as such, rely on the header module 6002 to supply power in the stack configuration. Only the header module 6002 is directly connected to the mains power 6020. The surgical modules 6004 lack direct connections to the mains power 6020, and can receive power only in the stack configuration. This arrangement improves the safety of the individual surgical modules 6004, and reduces the overall footprint of the modular energy system 6000. This arrangement further reduces the number of cords required for proper operation of the modular energy system 6000, which can reduce clutter and footprint in the operating room.

Accordingly, a surgical instrument connected to surgical modules 6004 of a modular energy system 6000, in the stack configuration, receives therapeutic energy for tissue treatment that is generated by the surgical module 6004 from power delivered to the surgical module 6004 from the AC/DC power supply 6003 of the header module 6002.

In at least one example, while a header module 6002 is assembled in a stack configuration with a first surgical module 6004', energy can flow from the AC/DC power supply 6003 to the first surgical module 6004'. Further, while a header module 6002 is assembled in a stack configuration with a first surgical module 6004' (connected to the header module 6002) and a second surgical module 6004" (connected to the first surgical module 6004'), energy can flow from the AC/DC power supply 6003 to the second surgical module 6004" through the first surgical module 6004'.

The energy generated by the AC/DC power supply 6003 of the header module 6002 is transmitted through a segmented power backplane 6008 defined through the modular energy system 6000. In the example of FIG. 15, the header module 6002 houses a power backplane segment 6008', the first surgical module 6004' houses a power backplane segment 6008", and the second surgical module 6004" houses a power backplane segment 6008'''. The power backplane segment 6008' is detachably coupled to the power backplane segment 6008" in the stack configuration. Further, the power backplane 6008" is detachably coupled to the power backplane segment 6008''' in the stack configuration. Accordingly, energy flows from the AC/DC power supply 6003 to the power backplane segment 6008', then to the power backplane segment 6008", and then to the power backplane segment 6008'''.

In the example of FIG. 15, the power backplane segment 6008' is detachably connected to the power backplane segment 6008" via pass-through hub connectors 6005, 6006 in the stack configuration. Further, the power backplane segment 6008" is detachably connected to the power backplane segment 6008''' via pass-through hub connectors 6025, 6056 in the stack configuration. In certain instances, removing a surgical module from the stack configuration severs its connection to the power supply 6003. For example, separating the second surgical module 6004" from the first surgical module 6004' disconnects the power backplane segment 6008''' from the power backplane segment 6008". However, the connection between the power backplane segment 6008" and the power backplane segment 6008''' remains intact as long as the header module 6002 and the first surgical module 6004' remain in the stack configuration. Accordingly, energy can still flow to the first surgical module 6004' after disconnecting the second surgical module 6004" through the connection between the header module 6002 and the first surgical module 6004'. Separating connected modules can be achieved, in certain instances, by simply pulling the surgical modules 6004 apart.

In the example of FIG. 15, each of the modules 6002, 6004 includes a mitigated module control 6023. The mitigated module controls 6023 are coupled to corresponding local power regulation modules 6024 that are configured to regulate power based on input from the mitigated module controls 6023. In certain aspects, the mitigated module controls 6023 allow the header module 6002 to independently control the local power regulation modules 6024.

The modular energy system 6000 further includes a mitigated communications interface 6021 that includes a segmented communication backplane 6027 extending between the mitigated module controls 6023. The segmented communication backplane 6027 is similar in many respects to the segmented power backplane 6008. Mitigated Communication between the mitigated module controls 6023 of the header module 6002 and the surgical modules 6004 can be achieved through the segmented communication backplane 6027 defined through the modular energy system 6000. In the example of FIG. 15, the header module 6002 houses a communication backplane segment 6027', the first surgical module 6004' houses a communication backplane segment 6027", and the second surgical module 6004" houses a communication backplane segment 6027'". The communication backplane segment 6027' is detachably coupled to the communication backplane segment 6027" in the stack configuration via the pass-through hub connectors 6005, 6006. Further, the communication backplane 6027" is detachably coupled to the communication backplane segment 6027" in the stack configuration via the pass-through hub connectors 6025, 6026.

Although the example of FIG. 15 depicts a modular energy system 6000 includes a header module 6002 and two surgical modules 6004' 6004", this is not limiting. Modular energy systems with more or less surgical modules are contemplated by the present disclosure. In some aspects, the modular energy system 6000 includes other modules such as, for example, a communications module. In some aspects, the header module 6502 supports a display screen such as, for example, the display 2006 (FIG. 7A) that renders a GUI such as, for example, the GUI 2008 for relaying information regarding the modules connected to the header module 6002. The GUI 2008 of the display screen 2006 can provide a consolidated point of control all of the modules making up the particular configuration of a modular energy system.

FIG. 16 depicts a simplified schematic diagram of the modular energy system 6000, which illustrates a primary communications interface 6040 between the header module 6002 and the surgical modules 6004. The primary communications interface 6040 communicably connects module processors 6041, 6041', 6041" of the header module 6002 and the surgical modules 6004. Commands generated by the module processor 6041 of the header module are transmitted downstream to a desired functional surgical module via the primary communications interface 6040. In certain instances, the primary communications interface 6040 is configured to establish a two-way communication pathway between neighboring modules. In other instances, the primary communications interface 6040 is configured to establish a one-way communication pathway between neighboring modules.

Furthermore, the primary communications interface 6040 includes a segmented communication backplane 6031, which is similar in many respects to the segmented power backplane 6008. Communication between the header module 6002 and the surgical modules 6004 can be achieved through the segmented communication backplane 6031 defined through the modular energy system 6000. In the example of FIG. 16, the header module 6002 houses a communication backplane segment 6031', the first surgical module 6004' houses a communication backplane segment 6031", and the second surgical module 6004" houses a communication backplane segment 6031'". The communication backplane segment 6031' is detachably coupled to the communication backplane segment 6031" in the stack configuration via the pass-through hub connectors 6005, 6006. Further, the communication backplane 6031" is detachably coupled to the communication backplane segment 6031" in the stack configuration via the pass-through hub connectors 6025, 6026.

In at least one example, as illustrated in FIG. 16, the primary communications interface 6040 is implemented using the DDS framework running on a Gigabit Ethernet interface. The module processors 6041, 6041', 6041" are connected to Gigabit Ethernet Phy 6044, and Gigabit Ethernet Switches 6042', 6042". In the example of FIG. 16, the segmented communication backplane 6031 connects the Gigabit Ethernet Phy 6044 and the Gigabit Ethernet Switches 6042 of the neighboring modules.

In various aspects, as illustrated in FIG. 16, the header module 6002 includes a separate Gigabit Ethernet Phy 6045 for an external communications interface 6043 with the processor module 6041 of the header module 6002. In at least one example, the processor module 6041 of the header module 6002 handles firewalls and information routing.

Referring to FIG. 15, the AC/DC power supply 6003 may provide an AC Status signal 6011 that indicates a loss of AC power supplied by the AC/DC power supply 6003. The AC status signal 6011 can be provided to all the modules of the modular energy system 6000 via the segmented power backplane 6008 to allow each module as much time as possible for a graceful shutdown, before primary output power is lost. The AC status signal 6011 is received by the module specific circuits 6013, 6014, 6015, for example. In various examples, the system power control 6017 can be configured to detect AC power loss. In at least one example, the AC power loss is detected via one or more suitable sensors.

Referring to FIGS. 15 and 16, to ensure that a local power failure in one of the modules of the modular energy system 6000 does not disable the entire power bus, the primary power input to all modules can be fused or a similar method of current limiting can be used (e-fuse, circuit breaker, etc.). Further, Ethernet switch power is segregated into a separate power domain 6013 so that the primary communications interface 6040 remains alive when local power to a module is removed. In other words, primary power can be removed and/or diverted from a surgical module without losing its ability to communicate with other surgical modules 6004 and/or the header module 6002.

Having described a general implementation the header and modules of modular energy systems 2000, 3000, 6000, the disclosure now turns to describe various aspects of other modular energy systems. The other modular energy systems are substantially similar to the modular energy system 2000, the modular energy system 3000, and/or the modular energy system 6000. For the sake of brevity, various details of the other modular energy systems being described in the following sections, which are similar to the modular energy system 2000, the modular energy system 3000, and/or the modular energy system 6000, are not repeated herein. Any aspect of the other modular energy systems described below can be brought into the modular energy system 2000, the modular energy system 3000, or the modular energy system 6000.

Mechanical Attachment Feature of the Modular Energy System Backplane Connector

Having described a general implementation of a modular energy systems 2000, 3000, 6000, the disclosure now turns to various aspects of the backplane connector of the modular energy systems 2000, 3000, 6000. In one aspect, the below described backplane connector can be added to any module of any of the modular energy systems 2000, 3000, 6000 accommodating modules of varying heights. In another aspect, the back plane connector can be built into a module enclosure. In another aspect the back plane connector can electrically and physically connect stacked modules of any of the modular energy systems 2000, 3000, 6000 with low profile cabling. In another aspect, the back plane connector can be attached to a module of any of the modular energy systems 2000, 3000, 6000 with snapping features.

The modular energy system can have multiple modules stacked on top of one another. The modules of the module energy system may contain a backplane connector subassembly that physically and electrically connect the stacked modules. In one aspect, each backplane connector subassembly may be required to withstand the weight of two modules, which could occur due to misalignment by the user when stacking a module. Accordingly, to withstand the weight of two modules the backplane connectors may require a robust attachment that can withstand the weight. Additionally, in one aspect, the backplane connector subassembly may be required to be adapted to different heights of future modules without modifying the connector design. Additionally, the attachment features may be required to not be visible from the outside of the unit to maintain an ideal aesthetic.

The back panel of the backplane connector subassembly could have, in one aspect, support members attached to it. The support members could be used to attach the upstream and downstream connectors via mating holes in the sides of each connector. The back panel attachment features or support members, in one aspect, could be fastener inserts that are attached to a sheet metal back panel. Such fastener inserts include inserts manufactured by PennEngineering known under the tradename PEM. Such fasteners include any one or more fasteners that utilize self-clinching, broaching, flaring, surface mount, or weld technology to provide strong, reusable, and permanent threads and mounting points in thin sheet metal, PCB materials, and other ductile or non-ductile thin material, for example. The upstream connector once attached may have ribs that extend down and may touch off on square fastener inserts, for example support ledges, attached to the back panel for added mechanical support.

In one aspect, fastener inserts are designed to be used for attaching components via threads, zip ties, etc. so this is a non-traditional way to use these inserts. From a Preliminary Finite Element Analysis the design may withstand loads of at least 60 lbs without yielding. In one aspect, by using fastener inserts to attach the support members to the panel, the attachment to the panel is nearly invisible from the rear of the panel which satisfies aesthetic requirements. The design may be adaptable for future modules as the support members can be attached to a sheet metal back panel of another module without the need to modify the backplane connectors themselves.

Figure 17:
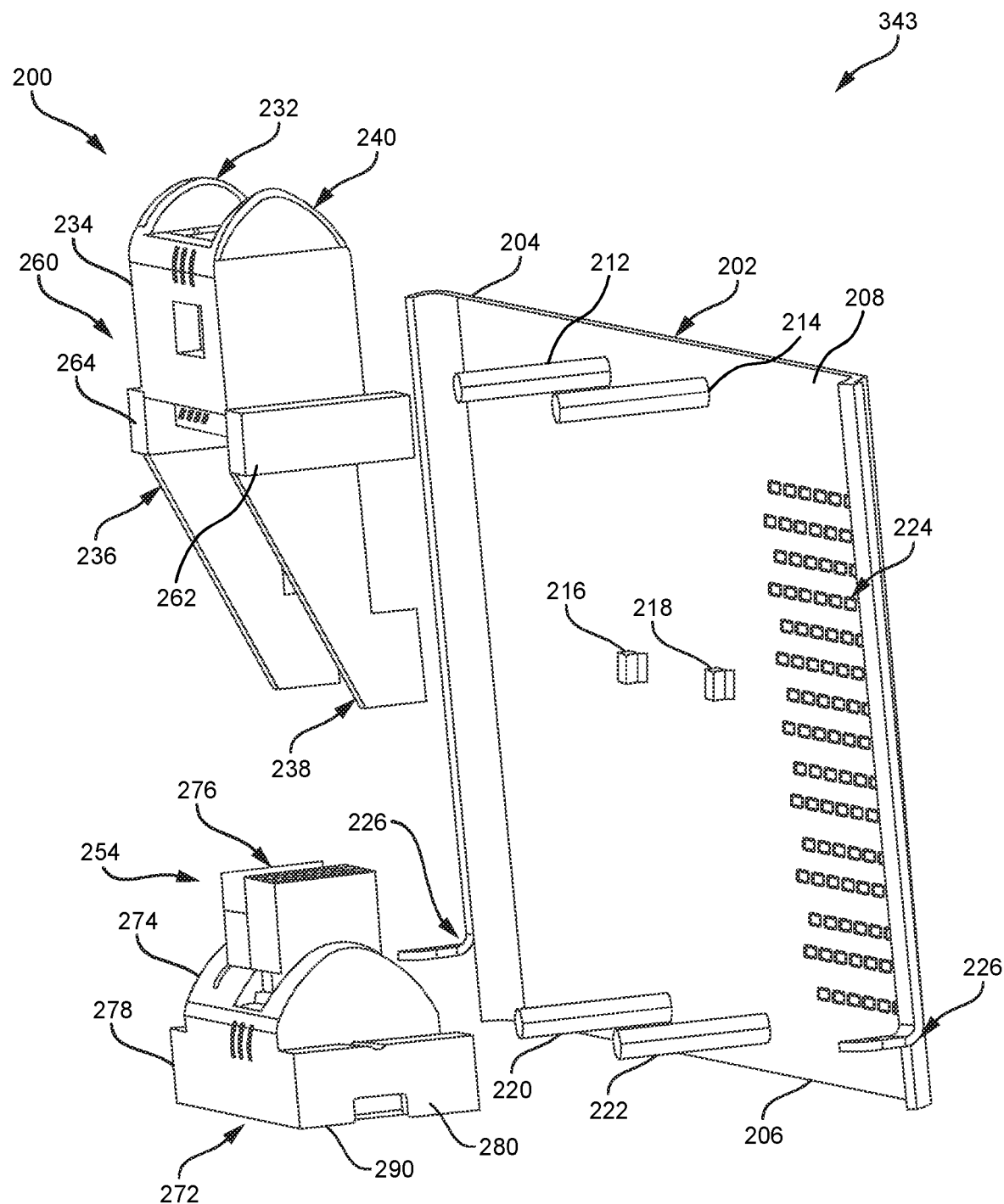
FIG. 17 is an exploded view of a backplane connector subassembly for a module of a modular energy system, in accordance with at least one aspect of the present disclosure.
Figure 18:
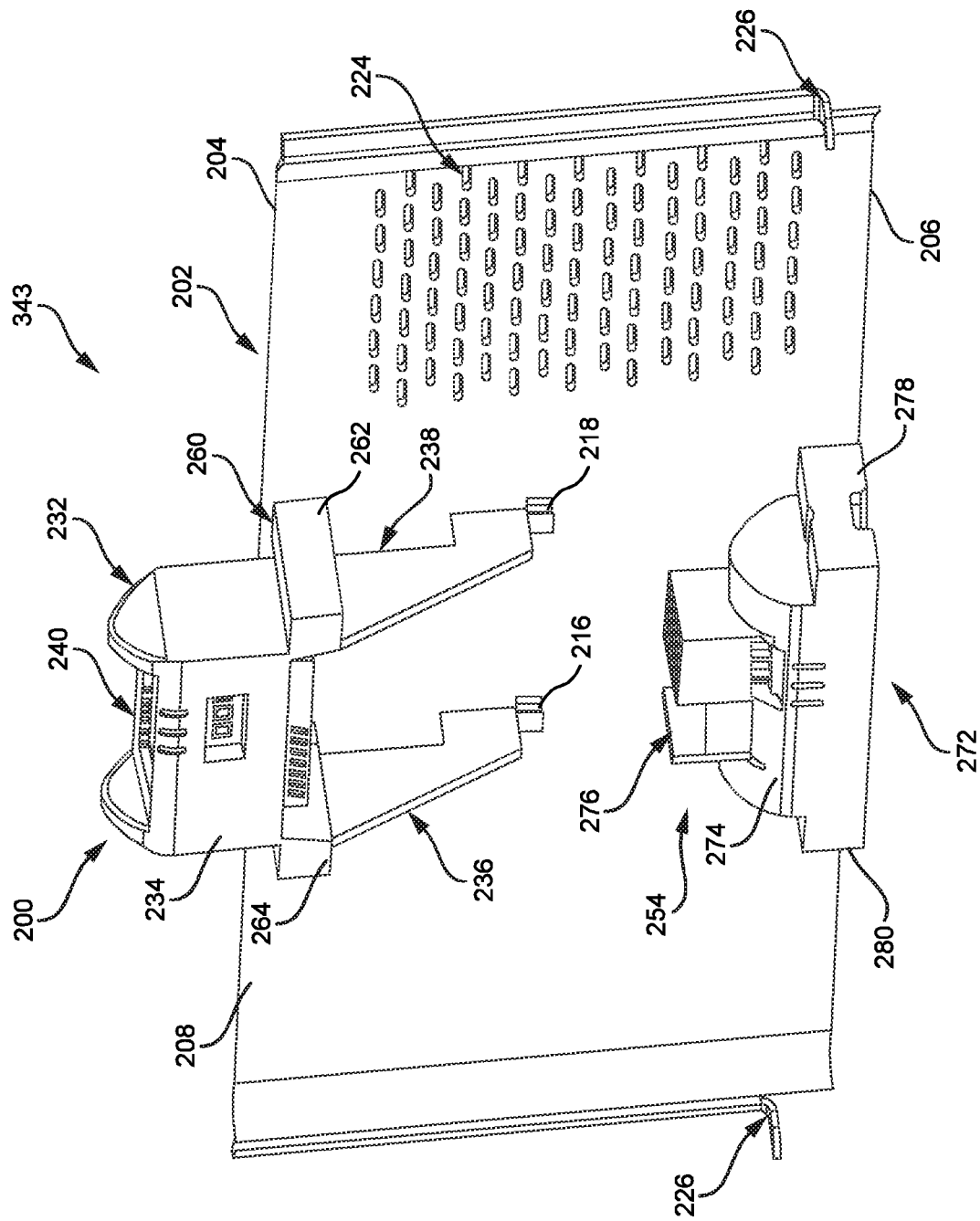
FIG. 18 is an elevated view of a backplane connector subassembly for a module of a modular energy system, in accordance with at least one aspect of the present disclosure.
Figure 19:
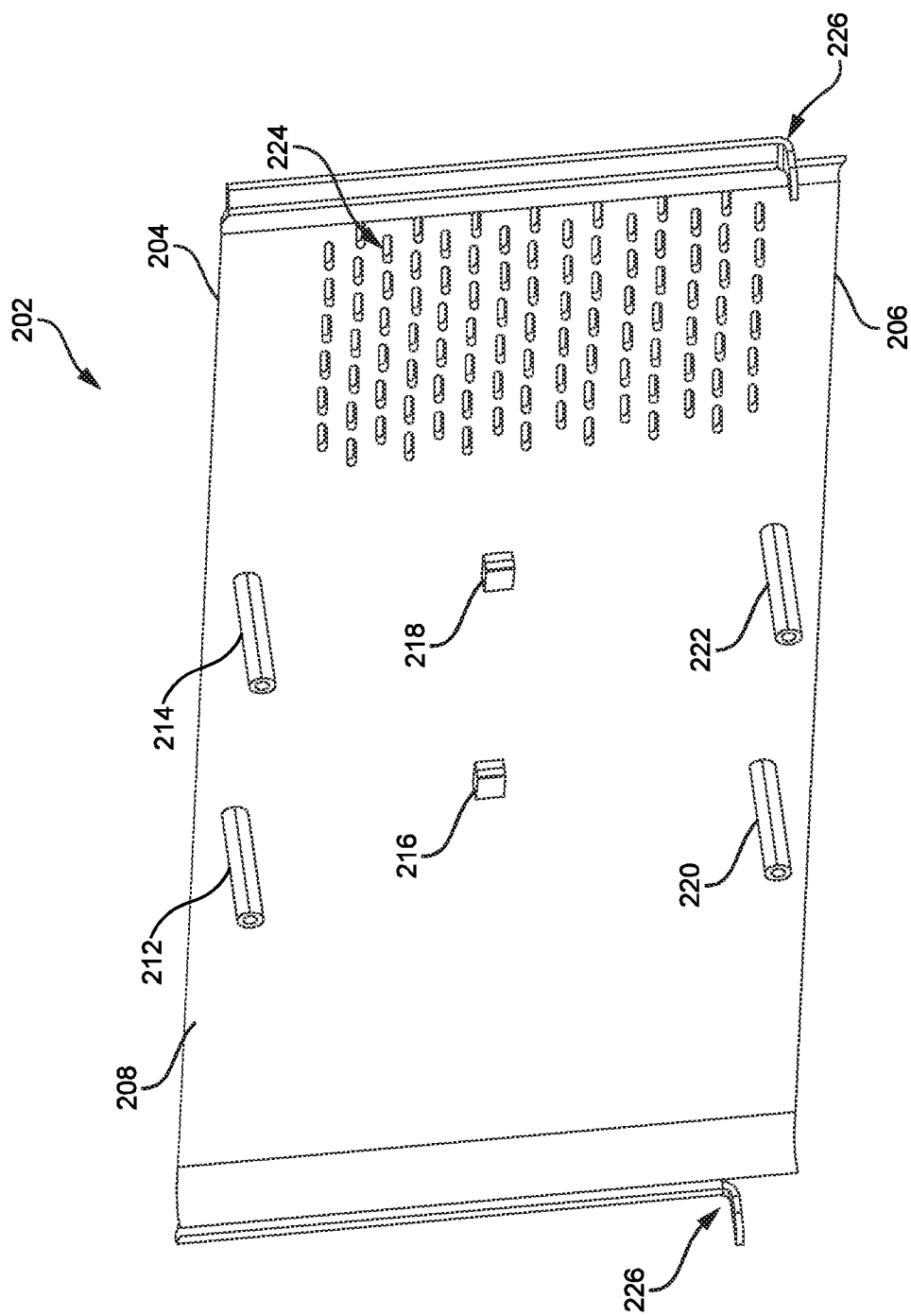
FIG. 19 is an elevated view of a panel of the backplane connector subassembly, in accordance with at least one aspect of the present disclosure.

In one aspect, FIGS. 17-19 show a backplane connector subassembly 343. Referring primarily to FIG. 17, the back panel 202 has 2 sets of support members attached to the inner surface 208 of the back panel 202. A first set of support members 212, 214 to attach an upstream connector 200 and a second set of support members 220, 222 to attach a downstream connector 280. In one aspect, there could be 4 support members to attach the upstream and downstream connectors, such as support members 212, 214, 220, 222. In another aspect, there could be any number of support members used to attach the upstream and down connectors, such as 1 support member for the upstream and 1 support member for the downstream.

Referring primarily to FIG. 19, the support members 212, 214, 220, 222 are attached to and extending away from the back panel 202. For example, the support members 212, 214, 220, 222 could be fastener inserts that are attached to a surface 208 of the back panel 202. In one aspect, the support members could extend perpendicularly away from the back panel 202. In other aspects, the support members 212, 214, 220, 222 could extend away at any angle from the back panel 202. Support ledges 216, 218 may be attached to the back panel 202 between the first set of support members 212, 214 and the second set of support members 220 222. The support ledges 216, 218 may be offset from the first set of support member 212, 214. The back panel 202 may have vent holes 224 to allow air flow into the module. Additionally the back panel 202 may have side edges 226 to allow the back panel to be attached to the enclosure of the module.

Referring to FIGS. 17 and 18, the upstream connector 200 can attach to the back panel 202 by sliding mating holes onto support members 212, 214. The downstream connector 254 attaches to the back panel 202 by a similar means as the upstream connector 200. For example, the downstream connector 254 can attach to the back panel 202 by sliding mating holes onto the support members 220, 222. FIG. 17 shows the upstream connector 200 and the downstream connector 254 detached from the back panel 202. FIG. 18 shows the upstream connector 200 and the downstream connector 254 attached to the back panel 202.

Still referring to FIGS. 17 and 18, the upstream connector 200 may attach to the back panel 202 by sliding mating holes onto support members 212, 214 of the back panel 202. The mating holes may be located on the lower portion 260 of the upstream connector 200, for example there may be a mating hole located in each protrusions 262, 264. The housing 234 may extend away from the lower portion 260 ending in the upper portion 232. Referring primarily to FIG. 18, when the upstream connector 200 is attached to the back panel 202 a portion of the housing 234 and upper portion 232 extends past the top edge 204 of the back panel 202. A hole 240 is where the electrical components may pass from the module above in the stack to the physically connected module below in the stack. Power and electrical communications may pass between the two modules. Support ribs 236, 238 can extend away from the lower portion 260 in the opposite direction of the housing 234. The support rib 236 may attach to the upstream connector 200 at the protrusion 264 and the support rib 238 may attach to the upstream connector 200 at the protrusions 262. Referring primarily to FIG. 18, when the upstream connector 200 is attached to the back panel 202, the support ribs 236, 238 may rest on the support ledges 216, 218. The support rib 236 may rest on the support ledge 216 and the support rib 238 may rest on the support ledge 218. It is noted that a design without the support ribs may also be possible.

Still referring to FIGS. 17 and 18, the downstream connector 254 may attach to the back panel 202 by sliding mating holes onto support members 220, 222 of the back panel 202. The mating holes may be located in the protrusions 278, 280. The housing 274 may extend away from the protrusions 278, 280. Referring primarily to FIG. 18, when the downstream connector 254 is attached to the back panel 202, the bottom 290 of the downstream connector 254 may align with the bottom edge 206 of the back panel 202. The hole 276 is where the electrical components may pass through the module to the next module down in the stack. The downstream connector 254 may have a cavity 272 at the bottom surface 290 of the downstream connector 254. The cavity 272 may be made to mate with the upper portion 232 of an upstream connector during stacking of modules.

When stacking a module the upper portion 232 of the upstream connector 200 of the lower module may enter the cavity 272 of the downstream connector 254 located in the upper module to electrically and physically connect the two modules. For example, when the modules are stacked the upper portion 232 may enter the cavity 272 and a plug inside of the downstream connector 254 may enter the hole 240 and connect with a plug inside of the upstream connector 200 to electrically connect the modules. In one aspect, the plug may be integrated into the connector assembly such that it is one molded component and not two separate components. In another aspect, the plug could be a separate component inserted into the connector. In yet another aspect, electrical pins/contacts may be integrated into the connector, for example pressed into. In one aspect, electrical wires may start at the plug inside of the upstream connector 230 and terminate at a printed circuit board in the module. In one aspect, similarly, electrical wires may start at the plug inside of the downstream connector 270 and terminate at a printed circuit board in the module. Multiple modules can be stacked on top of one another no matter the height of the module. Each module may have the same upstream connector 200 and downstream connector 254, which may allow the modules to be physically and electrically connected when the modules are stacked. When the modules are stacked and connected, power may transfer through the upstream connector 200 into the module and then through the downstream connector 254 to the next module lower in the stack. Electrical communications can pass through the upstream connector 200 and downstream connector 254 both ways.

To better understand the stacking the following is an example of stacking 3 modules. A first module can be on the bottom of the stack, a second module can be in the middle of the stack, and a third module can be on the top of the stack. The second module may be stacked on top of the first module. Then the upper portion 232 of the upstream connector 200 of the first module may enter the cavity 272 of the downstream connector 254 of the second module. The first and second modules may then be physically and electrically connected. Then the third module may be stacked on top of the second module. Then the upper portion 232 of the upstream connector 200 of the second module may enter the cavity 272 of the downstream connector 254 of the third module. The first, second, and third modules may then be physically and electrically connected. The upstream connector 200 and downstream connector 254 can be the same in each module. The height of the modules may vary since the upstream connector 200 and the downstream connector 254 are connected to the back panel 202 of the modules themselves.

Mechanical Attachment Feature of Backplane Connector

Figure 20:
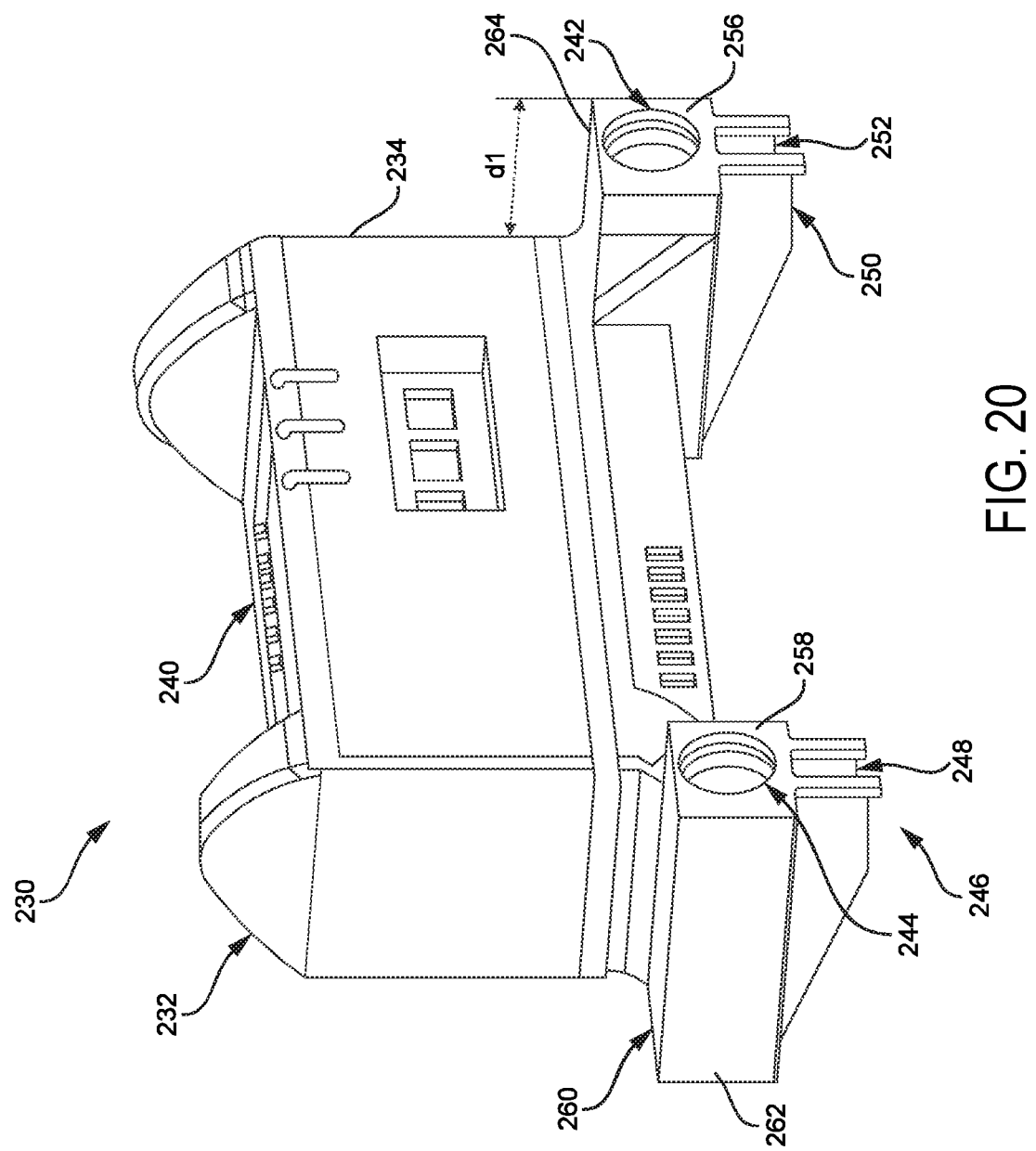
FIG. 20 is an elevated view of an upstream connector for a backplane connector subassembly, in accordance with at least one aspect of the present disclosure.

FIGS. 20-29 show different views of an alternate backplane connector subassembly 345 that is substantially similar to the back plane connector subassembly 343 of FIGS. 17-19. FIG. 20 shows an alternative upstream connector 230 that may be substantially similar to upstream connector 200. For the sake of brevity, not all of the details that are the same will be reiterated. The upstream connector 230 may comprise an upper portion 232, a hole 240, a housing 234, a lower portion 260, two protrusions 262, 264, and holes that mate with support members 212, 214, where each of these features are the substantially similar to the upstream connector 200. The upstream connector 230 may have a hole 244 located on the surface 258 of protrusion 262 and a hole 242 located on the surface 256 of the protrusion 264. The surface 256 may be offset from the housing 234 by a distance d1, and the surface 258 may be offset the same distance d1 from the housing 234. The upstream connector 230 may comprise 4 support ribs that extend away from the lower portion 260. There may be two support ribs 246, 248 that extend away from the protrusion 262 and two support ribs 250, 252 that extend away from the protrusion 264. A hole 240 is where the electrical components may pass from the module above in the stack to the physically connected module below in the stack.

Figure 21:
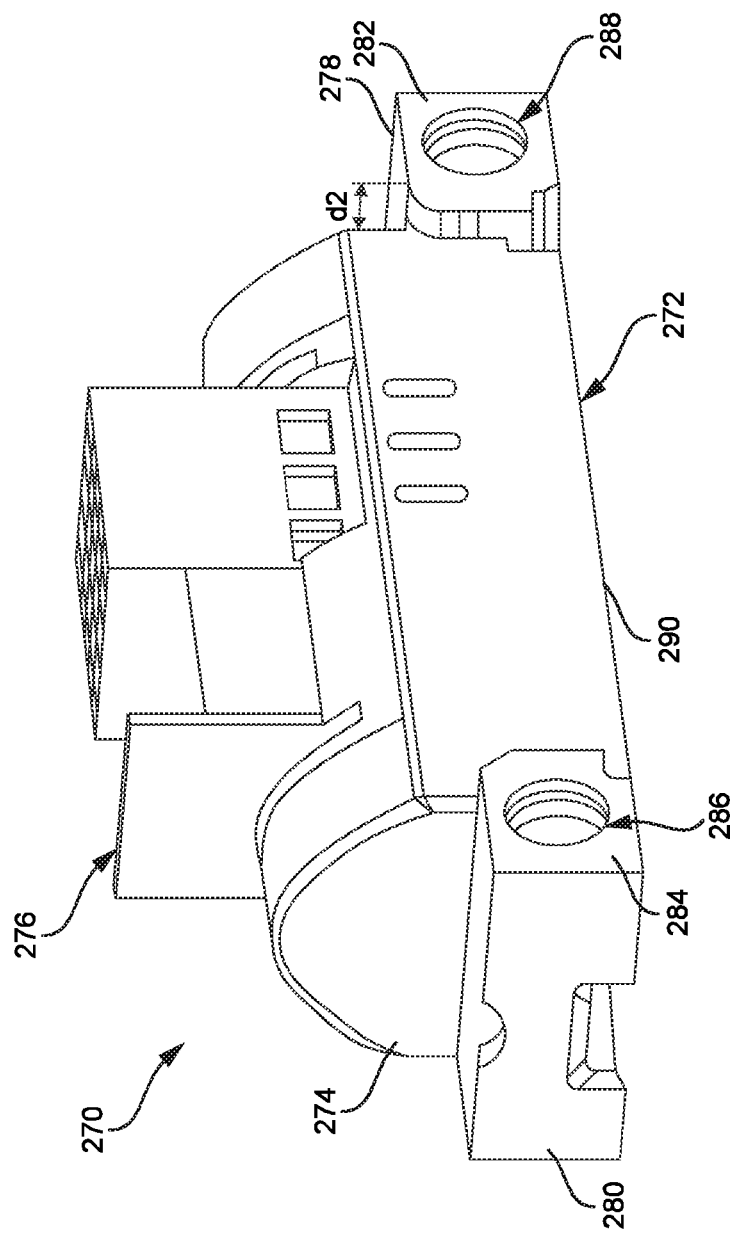
FIG. 21 is an elevated view of a downstream connector for a backplane connector subassembly, in accordance with at least one aspect of the present disclosure.

FIG. 21 shows an alternate downstream connector 270 that may be substantially similar to downstream connector 254. For the sake of brevity, not all of the details that are the same will be reiterated. The downstream connector 270 may comprise a housing 274, two protrusions 278, 280, a cavity 272, and holes that mate with support members 220, 222, where each of these features are substantially similar to the downstream connector 254. The downstream connector 270 may have a hole 286 located on a surface 284 of protrusion 280 and a hole 288 located on a surface 282 of the protrusion 278. The surface 282 may be offset from the housing 274 by a distance d2, and the surface 258 may be offset the same distance d2 from the housing 274. Hole 276 is where the electrical components may pass from the current module the stack to the physically connected module below in the stack. The downstream connector 270 may have a bottom surface 290 and on that surface there may be a cavity 272. The cavity 272 may be made to mate with the upper portion 232 of the upstream connector 230 during module stacking. In one aspect, when the modules are stacked the downstream connector 270 of the upper module mates with the upstream connector 230 of the lower module to physically and electrically connect the two modules. For example, when the downstream connector 270 and the upstream connector 230 are mated the hole 240 and hole 276 allow electrical components to connect between the upper module and the lower module.

Figure 22:
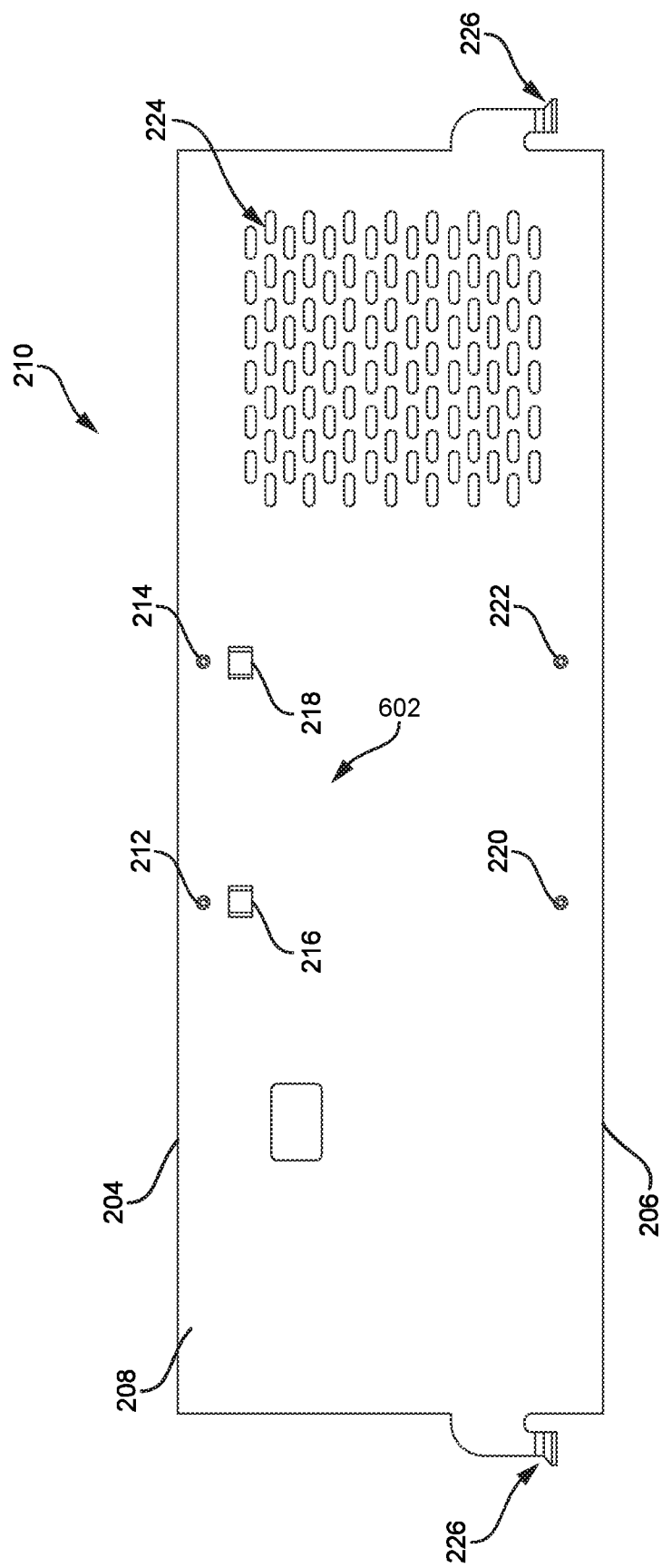
FIG. 22 is a front view of a panel for a backplane connector subassembly, in accordance with at least one aspect of the present disclosure.

FIG. 22 shows an alternate back panel 210 that may be substantially similar to downstream connector 254. For the sake of brevity, not all of the details that are the same will be reiterated. The back panel 210 may have a top edge 204, a bottom edge 206, a first set of support members 212, 214, a second set of support members 220, 222, a surface 208, side edges 226, vent holes 224, and support ledges 216, 218, where each of these features are substantially similar to the back panel 202. The support ledges 216, 218 may be attached to the surface 208 between the first set of support members 212, 214 and the second set of support members 220, 222. In one aspect, the support ledges 216, 218 may be attached closer to the first set of support members 212, 214 than the second set of support members 220, 222. In one aspect, the support members 212, 214, 220, 222 could extend perpendicularly away from the back panel 202. In other aspects, the support members 212, 214, 220, 222 could extend away at any angle from the back panel 202.

Figure 23:
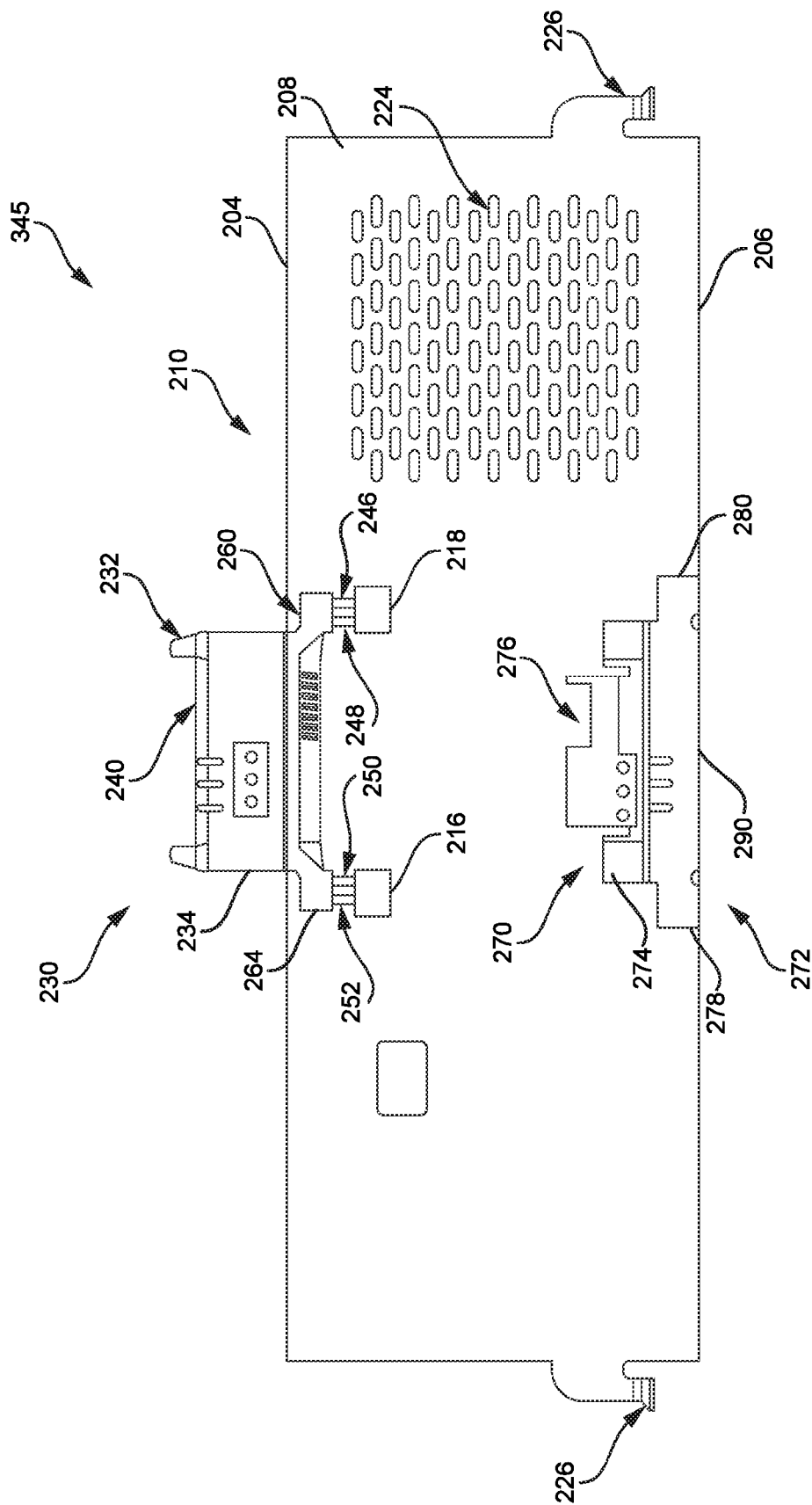
FIG. 23 is a front view of the panel for a backplane connector subassembly shown in FIG. 22 with the upstream and downstream connectors attached, in accordance with at least one aspect of the present disclosure.

Referring to FIG. 23, the upstream connector 230 and the downstream connector 270 are connected to the back panel 210. The upstream connector 230 may be attach to the back panel 210 by sliding the holes 242, 244 onto the support members 212, 214. For example, the hole 242 slides onto the support member 212 and the hole 244 slides onto the support member 214. For example, the upstream connector 230 may slide the holes 242, 244 onto the support members 212, 214 such that the surfaces 256, 258 touch surface 208. Once the upstream connector 230 is slide onto the support members 212, 214 the upstream connector 230 may be attached to the back panel 210. The support ribs 246, 248, 250, 252 may rest on the support ledges 216, 218 once the upstream connector 230 is attached to the back panel 210. For example, the support ribs 250, 252 may rest on support ledge 216 and the support ribs 246, 248 may rest on the support ledge 218. In one aspect, the support ribs 246, 248, 250, 252 provide additional physical support when modules are stacked. The upstream connector 230 may have upper portion 232 that extends past the top edge 204 of the back panel 210. A hole 240 is where the electrical components may pass from the module above in the stack to the physically connected module below in the stack.

Still referring to FIG. 23, the downstream connector 270 may be attach to the back panel 210 by sliding the holes 288, 286 onto the support members 220, 222. For example, the hole 288 slides onto the support member 220 and the hole 286 slides onto the support member 222. For example, the downstream connector 270 may slide the holes 288, 286 onto the support members 220, 222 such that the surfaces 282, 284 touch surface 208. Once the downstream connector 270 is slide onto the support members 220, 222, the downstream connector 270 may be attached to the back panel 210. The downstream connector 270 may have a surface 290 that aligns with the bottom edge 206 such that nothing extends past the bottom edge 206 of the back panel 210. The hole 276 is where the electrical components from the current module may pass to the next module below in the stack.

Figure 24:
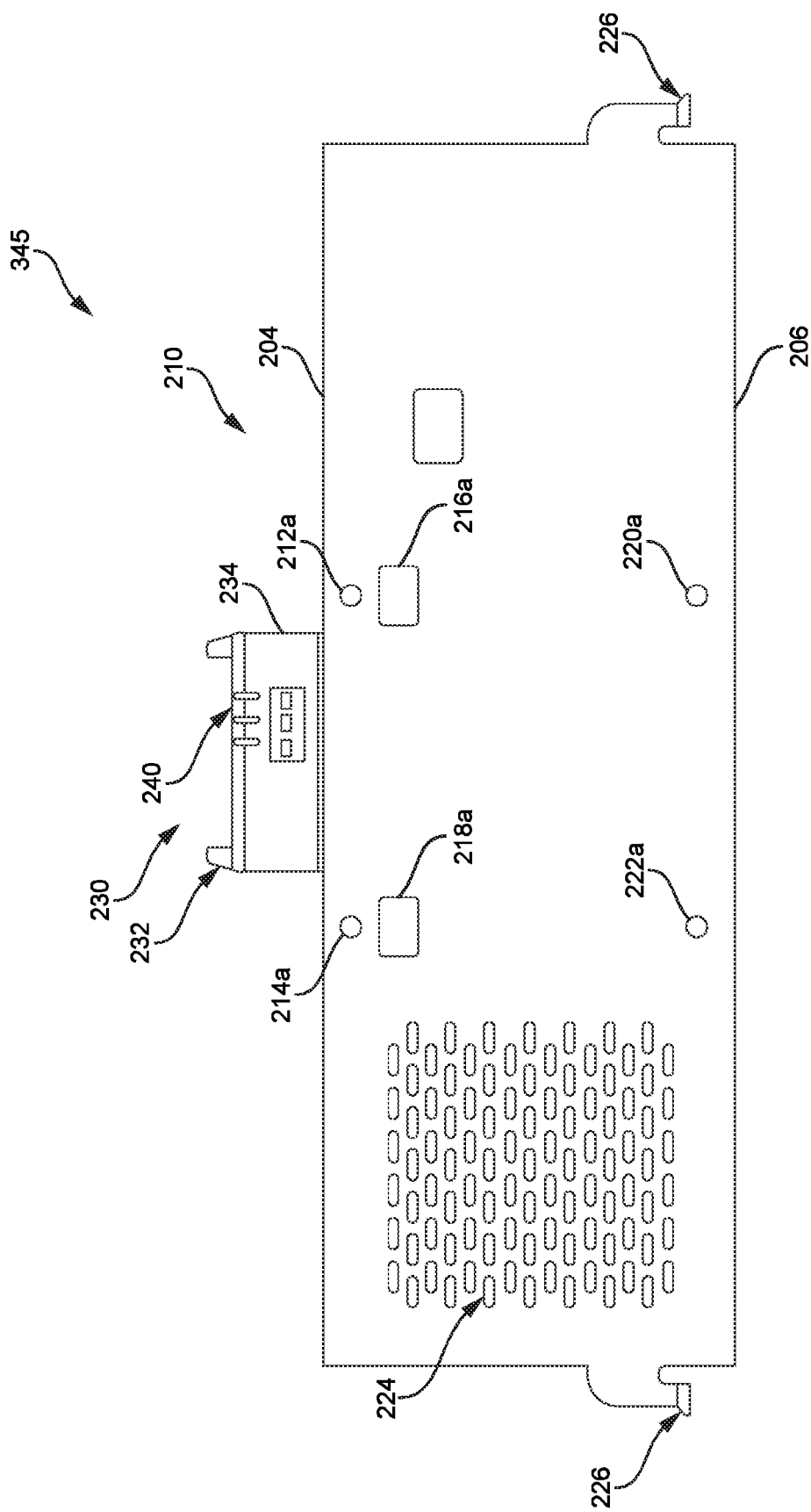
FIG. 24 is a back view of the panel shown in FIG. 23 with the upstream and downstream connectors attached, in accordance with at least one aspect of the present disclosure.

FIG. 24 shows a back view of the back panel 210 shown in FIG. 23. Stated another way FIG. 24 shows the view of the back of the module from the outside, where FIG. 23 shows the view of the back panel 210 from the inside of the module. Referring to FIG. 24, the upper portion 232 may extend past the top edge 204 of the back panel 210. The indents 212a, 214a may be all that is seen from the outside of the module from the attachment of the support members 212, 214. The indents 216a, 218a may be all that is seen from the outside of the module from the attachment of the support ridges 216, 218. The indents 220a, 222a may be all that is seen from the outside of the module of the attachment of the support members 220, 222. From the outside of the module, the downstream connector 270 may not be seen.

Figure 25:
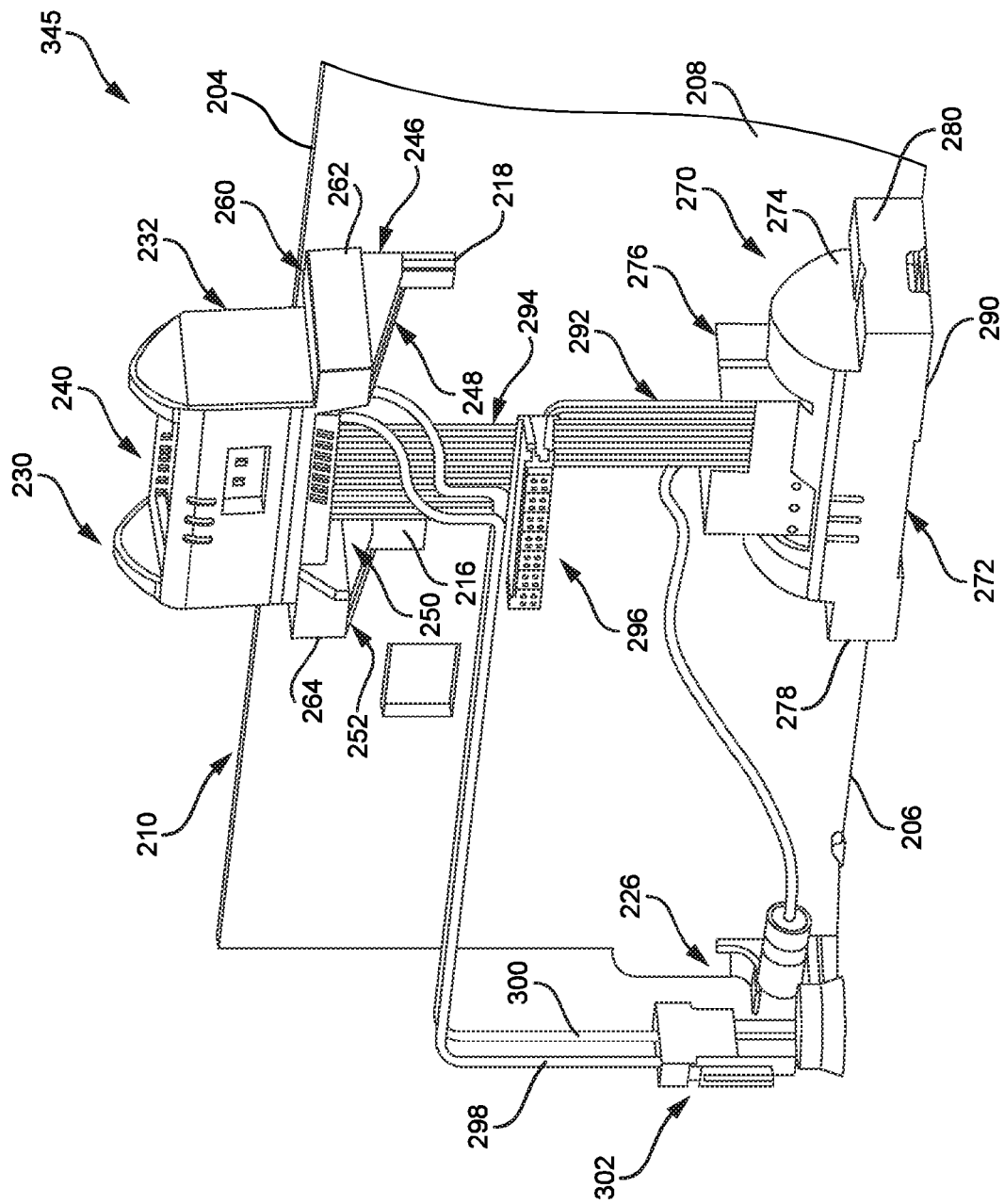
FIG. 25 is an elevated view of the backplane connector subassembly shown in FIG. 7 with connection wires added, in accordance with at least one aspect of the present disclosure.
Figure 26:
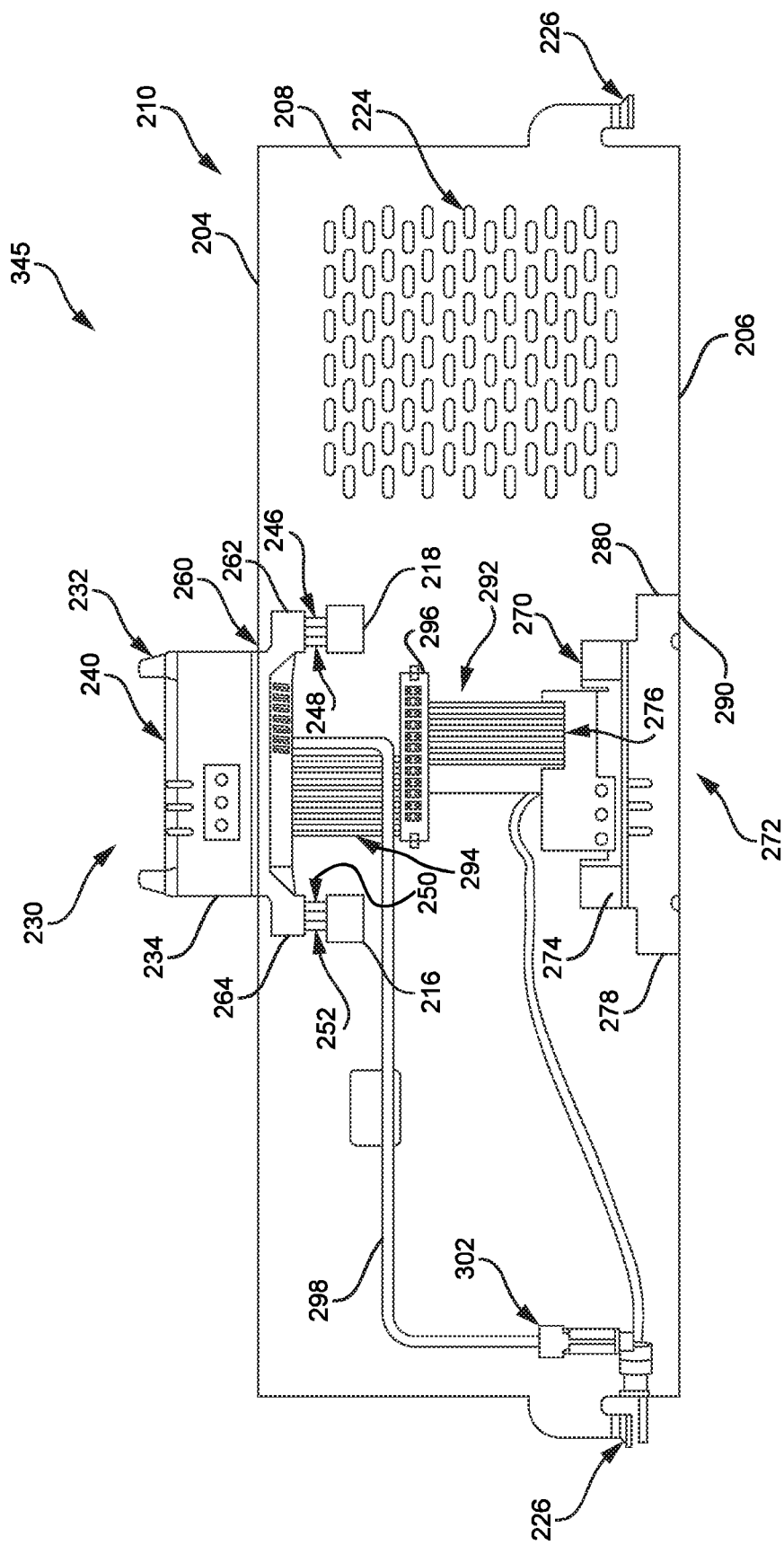
FIG. 26 is a front view of the backplane connector subassembly shown in FIG. 7 with connection wires added, in accordance with at least one aspect of the present disclosure.
Figure 27:
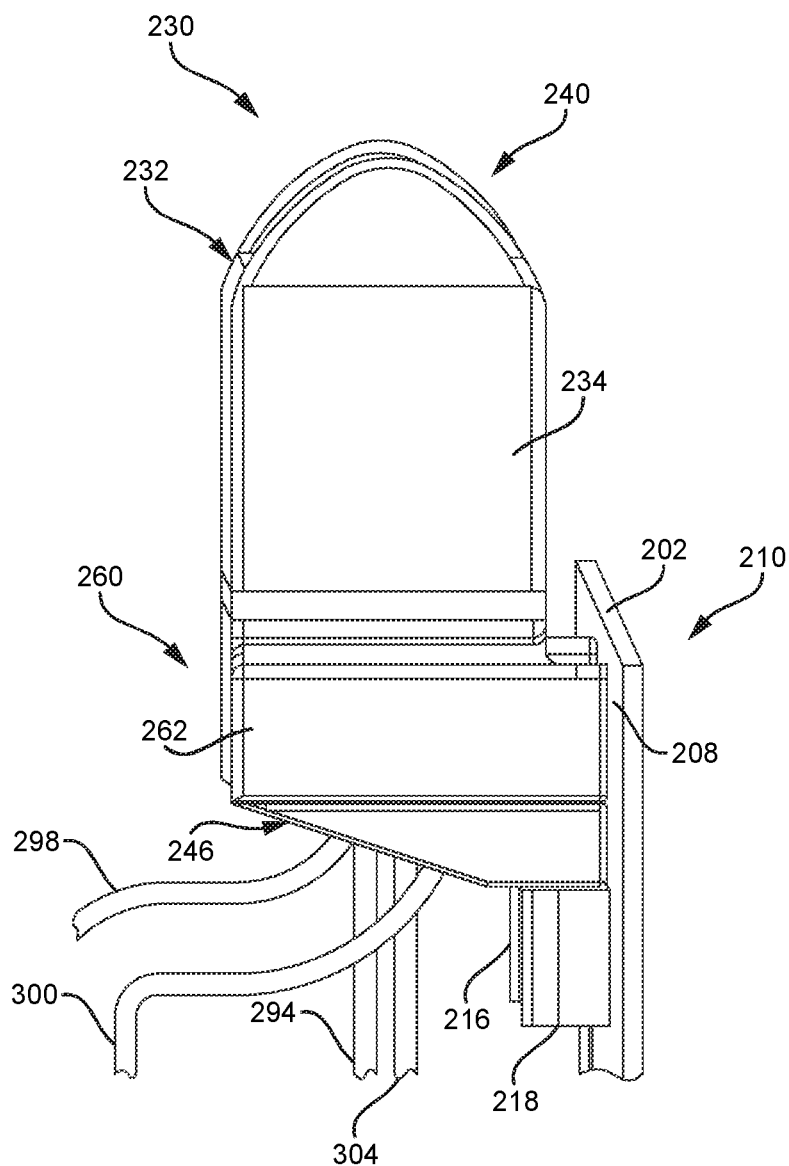
FIG. 27 is a side view of the upstream connector attached to the panel of the backplane subassembly, in accordance with at least one aspect of the present disclosure.
Figure 28:
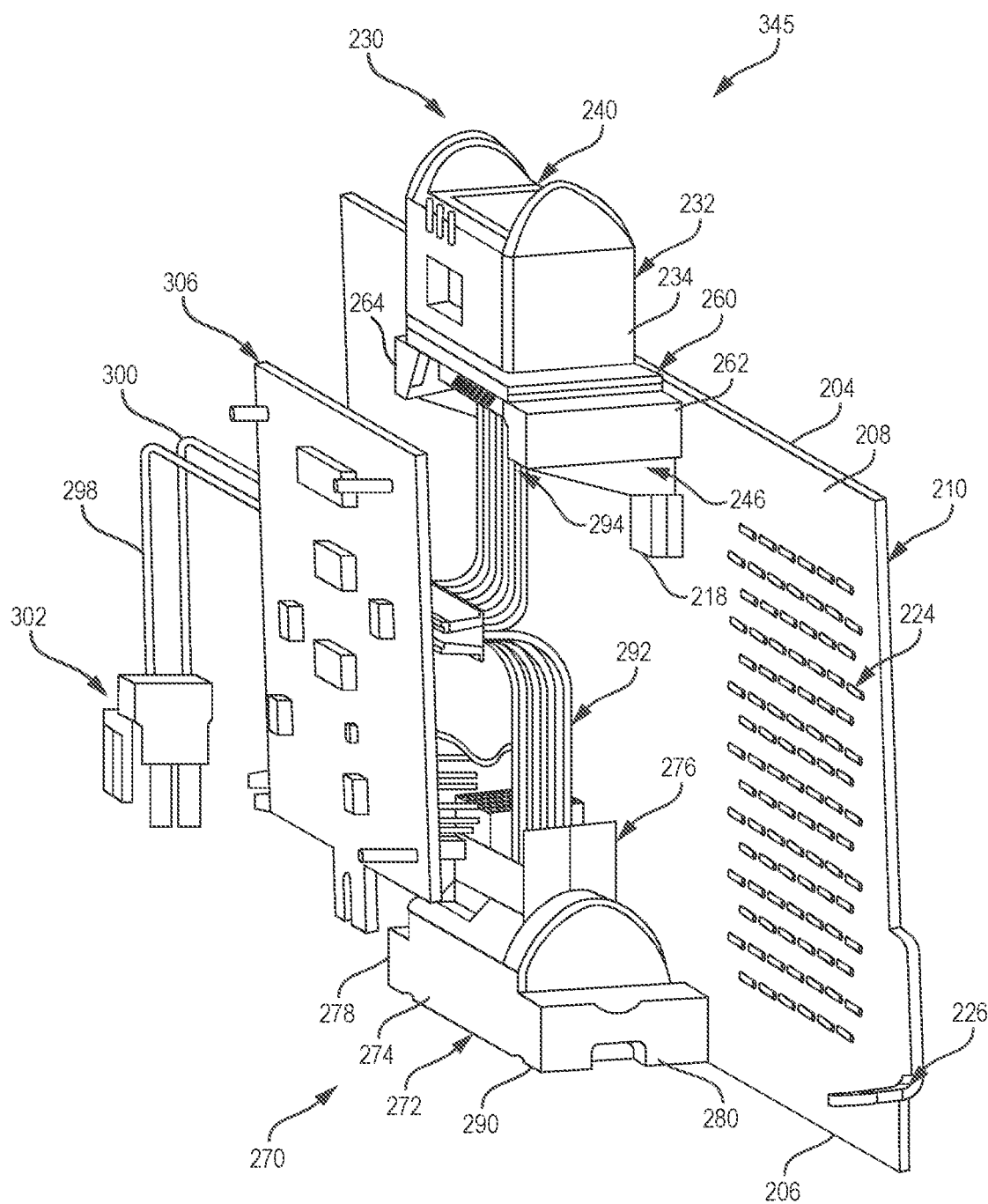
FIG. 28 is an elevated view of the backplane connector subassembly of FIG. 9 with the circuit board added, in accordance with at least one aspect of the present disclosure.
Figure 29:
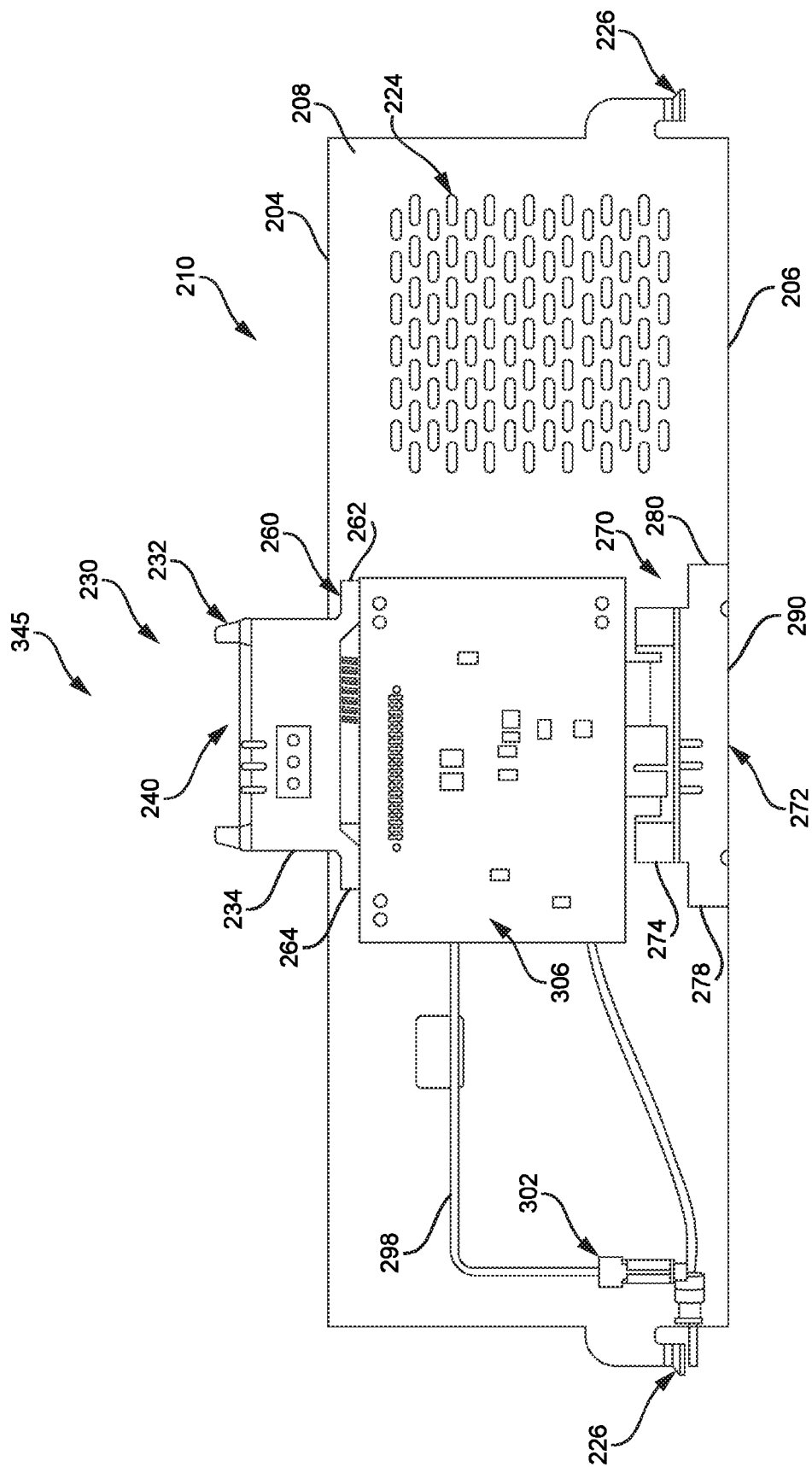
FIG. 29 is a front view of the backplane connector subassembly of FIG. 9 with the circuit board added, in accordance with at least one aspect of the present disclosure.

FIGS. 25-27 show some of the wires of the back plane connector subassembly. Referring to FIGS. 25 and 26, in one aspect, the electrical wires 294 may come down from a plug inside of the upstream connector 230 and terminate at plug 296. In one aspect, the electrical wires 294 can be used to send data between the stacked modules, for example sending data back and forth from the module higher in the stack to the current module. Referring to FIG. 27, the electrical wires 304 may come down from a plug inside of the upstream connector 230 and terminate at plug 296. In one aspect, the electrical wires 304 can be used to send data between the stacked modules, for example sending data back and forth from the module higher in the stack to the current module. Referring to FIGS. 25 and 26, the electrical wires 292 may come from a plug inside of the downstream connector 270 and terminate at the plug 296. In one aspect, the electrical wires 292 can be used to send data between the stacked modules, for example sending data back and forth from the module lower in the stack to the current module. Referring to FIGS. 28 and 29, a printed circuit board 306 for the module may connect with plug 296. In one aspect, the printed circuit board 306 controls the module and receives the transmits signals through the sets of wires 294, 304, 292. For example, the printed circuit board may be able to send data to and from the modules that are stacked above and below the current module. Referring to FIGS. 25-29, the electrical wire 298 and the electrical wire 300 may come from a plug in the upstream connector 230 and terminate at plug 302. In one aspect, the electrical wires 298 and 300 can be used to transport power to the current module.

When stacking a module, the upper portion 232 of the upstream connector 230 of the lower module may enter a cavity 272 of the downstream connector 270 located in the upper module electrically and physically connecting the two modules. In one aspect, a plug inside of the upstream connector 230 may connect with a plug inside of the downstream connector 270 to electrically connect the modules that are stacked. For example, when the modules are stacked the upper portion 232 may enter the cavity 272 and a plug inside of the downstream connector 270 may enter the hole 240 and connect with a plug inside of the upstream connector 230 to electrically connect the modules. In one aspect, the plug may be integrated into the connector assembly such that it is one molded component and not two separate components. In another aspect, the plug could be a separate component inserted into the connector. In yet another aspect, electrical pins/contacts may be integrated into the connector, for example pressed into. In one aspect, electrical wires may start at the plug inside of the upstream connector 230 and terminate at a printed circuit board in the module. In one aspect, similarly, electrical wires may start at the plug inside of the downstream connector 270 and terminate at a printed circuit board in the module. Multiple modules can be stacked on top of one another no matter the height the modules. Each module may have the same upstream connector 230 and downstream connector 270, which allow the modules to be physically and electrically connected when the modules are stacked. When the modules are stacked and connected, power transfers through the upstream connector 230 into the module and then through the downstream connector 270 to the next module lower in the stack. Electrical communications can pass through the upstream connector 230 and downstream connector 270 both ways.

To better understand the stacking, the following is an example of stacking 3 modules. A first module can be on the bottom of the stack, a second module can be in the middle of the stack, and a third module can be on the top of the stack. The second module may be stacked on top of the first module. Then the upper portion 232 of the upstream connector 230 of the first module may enter the cavity 272 of the downstream connector 270 of the second module. The first and second modules may then be physically and electrically connected. Then the third module may be stacked on top of the second module. The upper portion 232 of the upstream connector 230 of the second module may enter the cavity 272 of the downstream connector 270 of the third module. The first, second, and third modules may then be physically and electrically connected. The upstream connector 230 and downstream connector 270 can be the same in each module. The height of the modules may vary since the upstream connector 230 and the downstream connector 270 are connected to the back panel 210 of the modules themselves.

Energy Module Bridge Connector

In various aspects, an end user is permitted to assemble any suitable number of modules into a variety of different stacked configurations that support electrical energy flow therebetween. Each of the different types of modules provides different functionality, thereby allowing individuals to customize the functions provided by each surgical platform by customizing the modules that are included in each surgical platform. The modular energy system is assembled or is modified by an end user either prior to or during a surgical procedure. Since the manufacturer is not involved with the final assembly of a modular energy system, suitable precautions are taken to ensure proper stacking of an assembled modular energy system and/or alignment of modules within the modular energy system.

As discussed above, the one or more modules can be connected together in a variety of different stacked configurations to form various modular energy systems. When positioned in the variety of different stacked configurations, the surgical modules are configured to communicate and transmit power therebetween. It is contemplated that external wiring connections can be utilized in order to electrically couple the modules when stacked together to facilitate the transmission of communication signals and power. However, it is desirable that the modules be connectable together without the need for external wiring to facilitate safe assembly and disassembly by an end user. To that end, the modules can include bridge connectors that are configured to transmit power and/or communication signals between the modules in the modular energy system when the modules are assembled or engaged together.

In one general aspect, the present disclosure provides a connector positioned on the top and a socket on the bottom of a stackable energy module, which can carry communication and power through multiple units (i.e., modules). The connector shape facilitates mechanical alignment, then grounding, then electrical contact of a series of power and communication lines when multiple energy modules are assembled together into a modular energy system.

In another general aspect, the present disclosure provides a bridge circuit that is segmented into identical boards residing within each module and is connected by connectors shaped to align and connect a variable number of stacked modules together (including a header module).

In another general aspect, the present disclosure provides a module connector configured to have a first or stowed configuration and second or extended configuration. The modular connectors for energy modules (and/or other modules of a modular energy system) can carry both communication and power between modules, where the connector is configured to be transitioned between the stowed configuration, which has a first low profile, and the extended configuration, which provides for both an electrical and mechanical connection between modules.

In yet another general aspect, the present disclosure provides a surgical platform comprising a first surgical module and a second surgical module. The first surgical module is configured to be assembled in a stack configuration with the second surgical module. The first surgical module includes a first bridge connector portion, which comprises a first outer housing and first electrical connection elements. The second surgical module comprises a second bridge connector portion, which comprises a second outer housing and second electrical connection elements. The second outer housing is shaped and configured to engage the first outer housing during the assembly before second electrical connection elements engage the first electrical connection elements.

In yet another general aspect, the present disclosure provides a surgical platform comprising a first surgical module and a second surgical module. The first surgical module comprises a first enclosure comprising a bottom surface, a first bridge connector, wherein the first bridge connector comprises a recess, a first printed circuit board (PCB), and a first wire assembly connected to the first PCB. The first wire assembly extends from the first PCB to the first bridge connector and the first wire assembly is operably coupled to the first bridge connector. The second surgical module comprises a second enclosure comprising a top surface, a second bridge connector, a second PCB, and a second wire assembly connected to the second PCB. The second bridge connector extends away from the top surface and the second bridge connector is configured to be positioned in the recess of the first bridge connector of the first surgical module. The second wire assembly extends from the second PCB to the second bridge connector and the second wire assembly is operably coupled to the second bridge connector. When the second bridge connector is positioned in the first bridge connector, the second wire assembly is electrically coupled with the first wire assembly.

Figure 30:
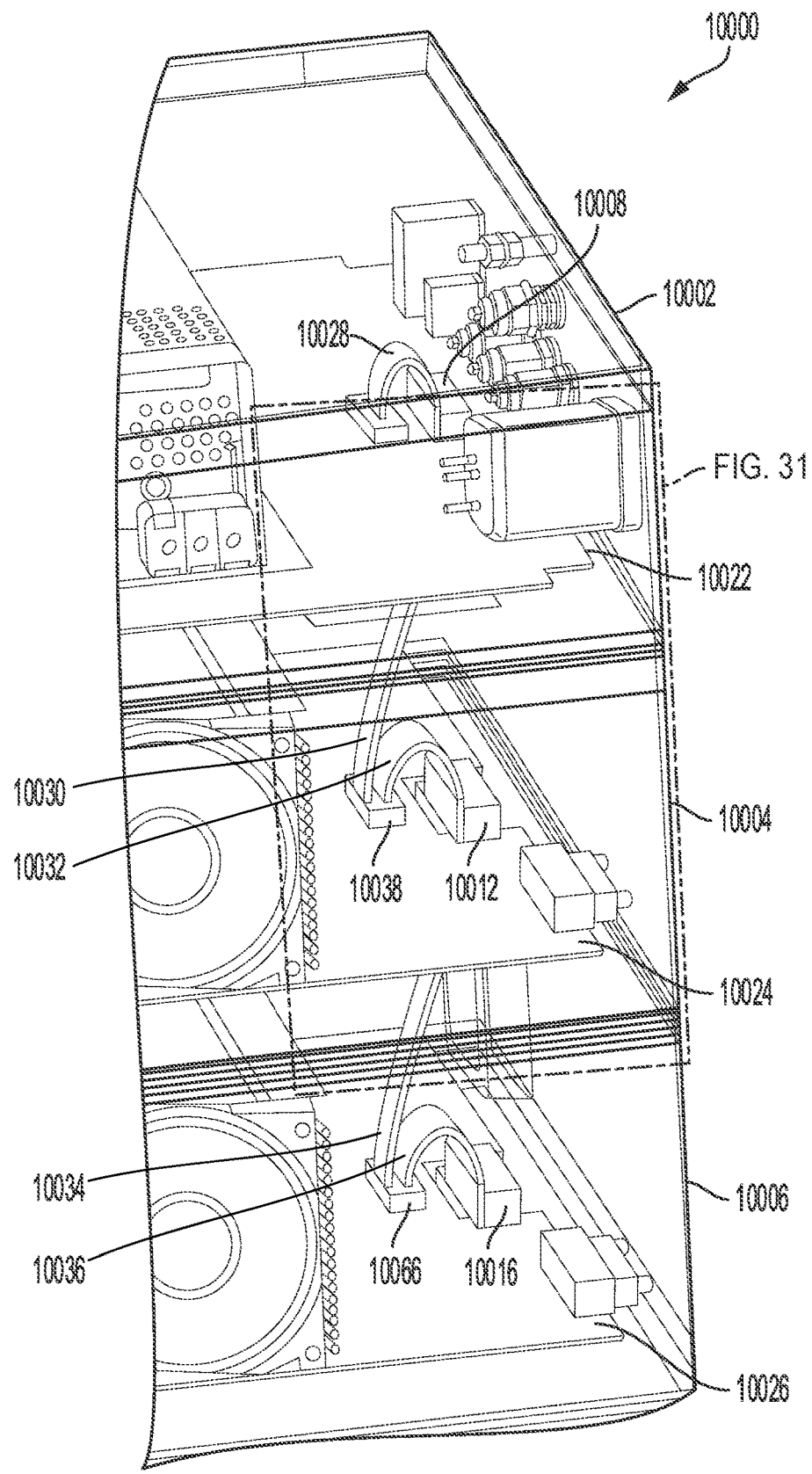
FIG. 30 illustrates a modular energy system, in accordance with at least one aspect of the present disclosure.
Figure 31:
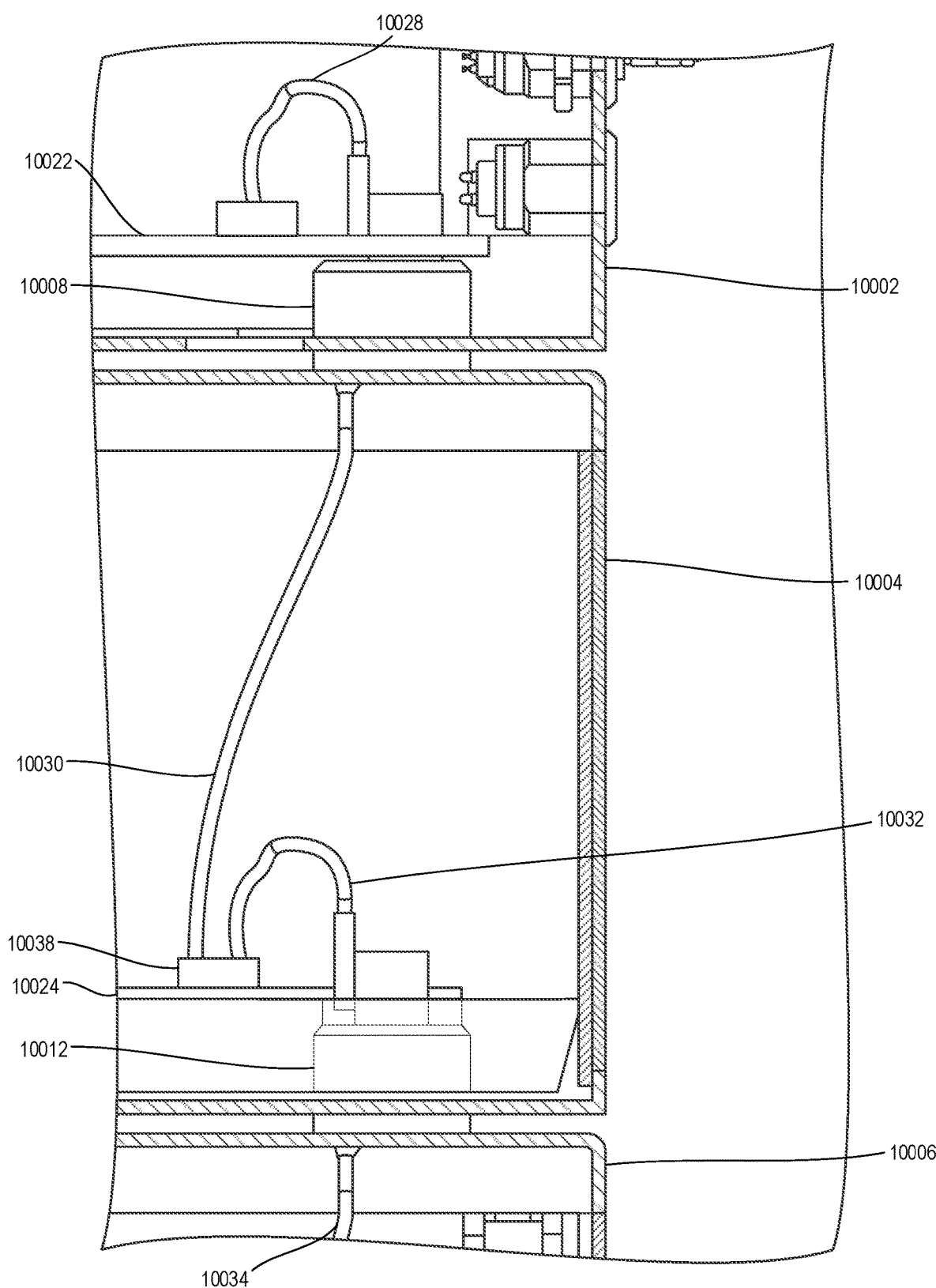
FIG. 31 illustrates various electrical connections in the modular energy system of FIG. 30, in accordance with at least one aspect of the present disclosure.

Referring now to FIGS. 30 and 31, a configuration is shown in which three surgical modules, a first module 10002, a second module 10004, and a third module 10006, are assembled together in a stacked configuration by an end user utilizing an internal wiring arrangement to facilitate the transmission of communication signals and power between modules in a modular energy system 10000. Each module 10002, 10004, and 10006, can be the same type of surgical module or different types of surgical modules. For example, each module 10002, 10004, and 10006, can be a header module, an energy module, a generator module, an imaging module, a smoke evacuation module, a suction/irrigation module, a communication module, a processor module, a storage array, a surgical device coupled to a display, a non-contact sensor module, or other modular device. These and other such modules are described above under the headings SURGICAL HUBS and MODULAR ENERGY SYSTEM.

Each module 10002, 10004, and 10006, can include a bridge connector. For example, the first module 10002 can comprise a lower bridge connector 10008, the second module 10004 can comprise an upper bridge connector 10010 (FIG. 32) and a lower bridge connector 10012, and the third module 10006 can comprise an upper bridge connector (not shown) and a lower bridge connector 10016. Each bridge connector, 10008, 10010, 10012, and 10016, can include an outer housing extending at least partially around electrical connection elements of the respective bridge connector.

Figure 32:
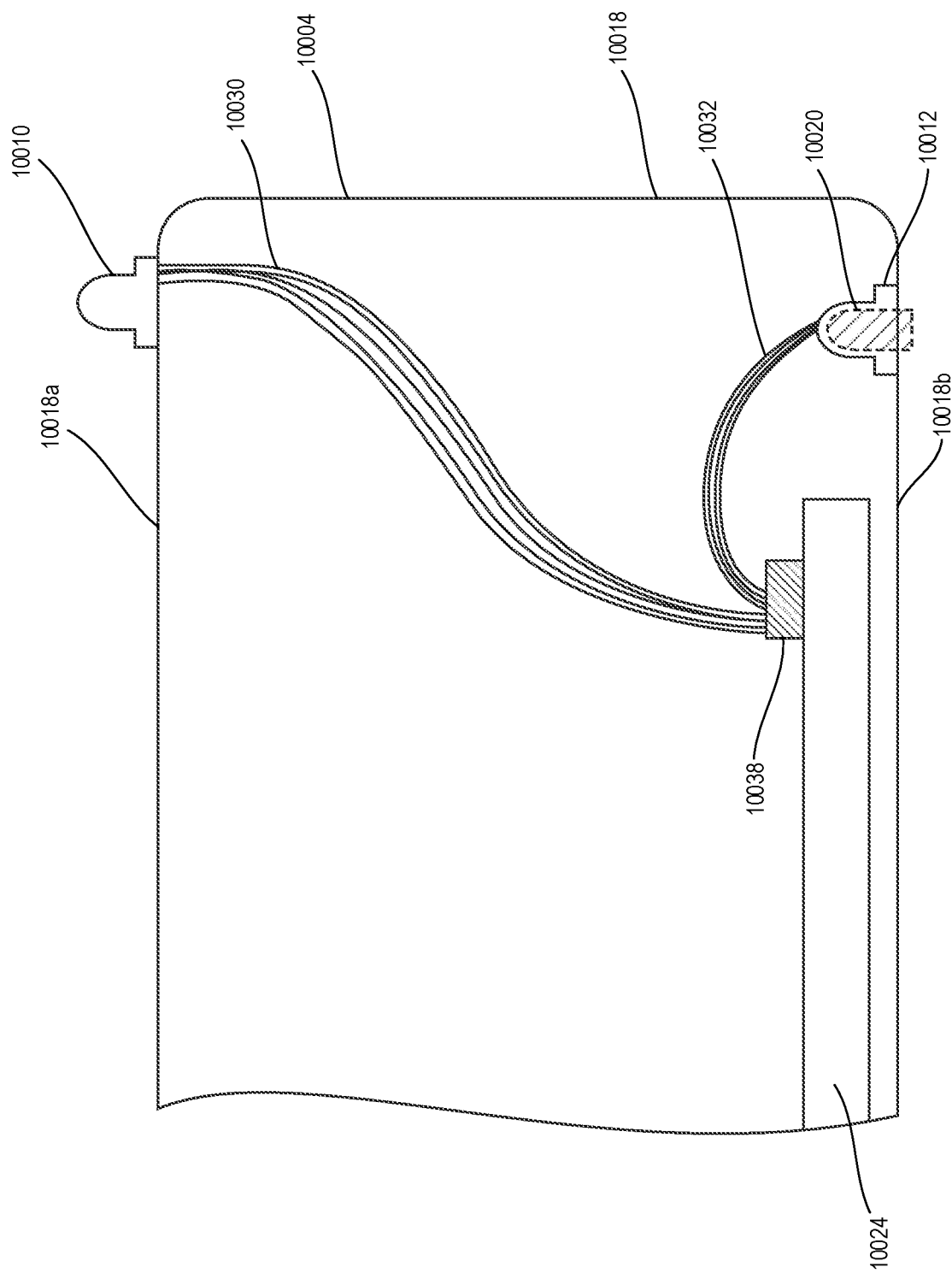
FIG. 32 illustrates a module of the modular energy system of FIG. 30, in accordance with at least one aspect of the present disclosure.

Referring to FIG. 32, a detailed view of an aspect of the second module 10004 is provided. It is understood the first module 10002 and the third module 10006 can be configured as the second module 10004 illustrated in FIG. 32. The upper bridge connector 10010 of the second module 10004 is mounted to a top surface 10018*a* of the enclosure 10018 and extends away from the second module 10004. The lower bridge connector 10012 of the second module 10004 is mounted to the bottom surface 10018*b* of the enclosure 10018 of the second module 10004. The lower bridge connector 10012 includes a recess 10020 that is shaped and configured to receive an upper bridge connector from a separate module. For example, when the second module 10004 is stacked on top of the third module 10006, the upper bridge connector of the third module 10006 is inserted into the recess 10020 of the lower bridge connector 10016 of the second module 10004, thus, aligning the second module 10004 with the third module 10006.

Referring to back to FIGS. 30 and 31, each module, 10002, 10004, and 10006, further includes a PCB. For example, the first module 10002 includes a first PCB 10022, the second module 10004 includes a second PCB 10024, and the third module 10006 includes a third PCB 10026.

Additionally, each module, 10002, 10004, and 10006, includes a flexible wire harness (e.g., flexible cable) electrically connected to the respective PCB, 10022, 10024, and 10026, by any suitable number of connections. For example, the first module 10002 includes a first flexible wire harness 10028 extending from the first PCB 10022 and operably coupled to the lower bridge connector 10008 of the first module 10002 to connect the first PCB 10022 with electrical connection elements of the lower bridge connector 10008. The first flexible wire harness 10028 is positioned within the first module 10002 and, thus, may facilitate quicker assembly of a modular energy system.

The second module 10004 includes a second flexible wire harness 10030 and a third flexible wire harness 10032 extending from the second PCB 10024. The second flexible wire harness 10030 is operably coupled to the upper bridge connector 10010 of the second module 10004 to connect the second PCB 10024 with electrical connection elements of the upper bridge connector 10010. The third flexible wire harness 10032 is operably coupled to the lower bridge connector 10012 of the second module 10004 to connect the second PCB 10024 with electrical connection elements of the lower bridge connector 10012. The second and third flexible wire harnesses 10030 and 10032 are positioned within the second module 10002 and, thus, may facilitate quick assembly of a modular energy system.

The third module 10006 includes a fourth flexible wire harness 10034 and a fifth flexible wire harness 10036 extending from the third PCB 10026. The fourth flexible wire harness 10034 is operably coupled to the upper bridge connector of the third module 10006 to connect the third PCB 10026 with electrical connection elements of the upper bridge connector of the third module 10006. The fifth flexible wire harness 10036 is operably coupled to the lower bridge connector 10016 of the third module 10006 to connect the third PCB 10026 with the electrical connection elements of the lower bridge connector 10016. The fourth and fifth flexible wire harnesses 10034 and 10036 are positioned within the third module 10002 and thus, may facilitate quick assembly of a modular energy system.

When an upper bridge connector of a lower module is positioned in a lower bridge connector of an upper module (e.g., the electrical connection elements of the bridge connectors are electrically coupled), the upper flexible wire harness connected to the upper bridge connector of the lower module is electrically coupled with the lower flexible wire harness connected to the lower bridge connector of the upper module. When coupled, power and communication signals are able to flow from the lower module to the upper module (and/or from the upper module to the lower module) by way of the internal flexible wire harnesses and the PCBs. For example, when the upper bridge connector 10014 of the third module 10006 is positioned in the lower bridge connector 10012 of the second module 10004, the fourth flexible wire harness 10034 is electrically coupled with the third flexible wire harness 10032. Thus, power and communications signals are able to flow from the third module 10006 to the second module 10004 by way of the third and fourth flexible wire harnesses, 10032 and 10034, and the respective PCBs, 10023 and 10026.

Referring back to FIGS. 30-32, in one instance, a board connector 10038 is mounted on the second PCB 10024 and a board connector 10066 is mounted on the third PCB 10026. The second flexible wire harness 10030 is configured to extend from the upper bridge connector 10010 and connect to the board connector 10038, while the third flexible wire harness 10032 is configured to extend from the lower bridge connector 10012 and connect to the board connector 10038. The fourth flexible wire harness 10034 is configured to extend from the upper bridge connector of the third module 10006 and connect to the board connector 10066, while the fifth flexible wire harness 10036 is configured to extend from the lower bridge connector 10016 and connect to the board connector 10066.

Similar to the scenario described above, when an upper module is connected with a lower module by way of respective bridge connectors, the upper and lower modules are able to communicate and transmit power therebetween by way of the PCBs, the board connectors, and the flexible wire harnesses. For example, referring to FIG. 31, power and communications signals are able to flow from the third module 10006 to the second module 10004 by way of the third and fourth flexible wire harnesses, 10032 and 10034, the board connectors, 10038 and 10066, and the respective PCBs, 10024 and 10026.

Figure 33:
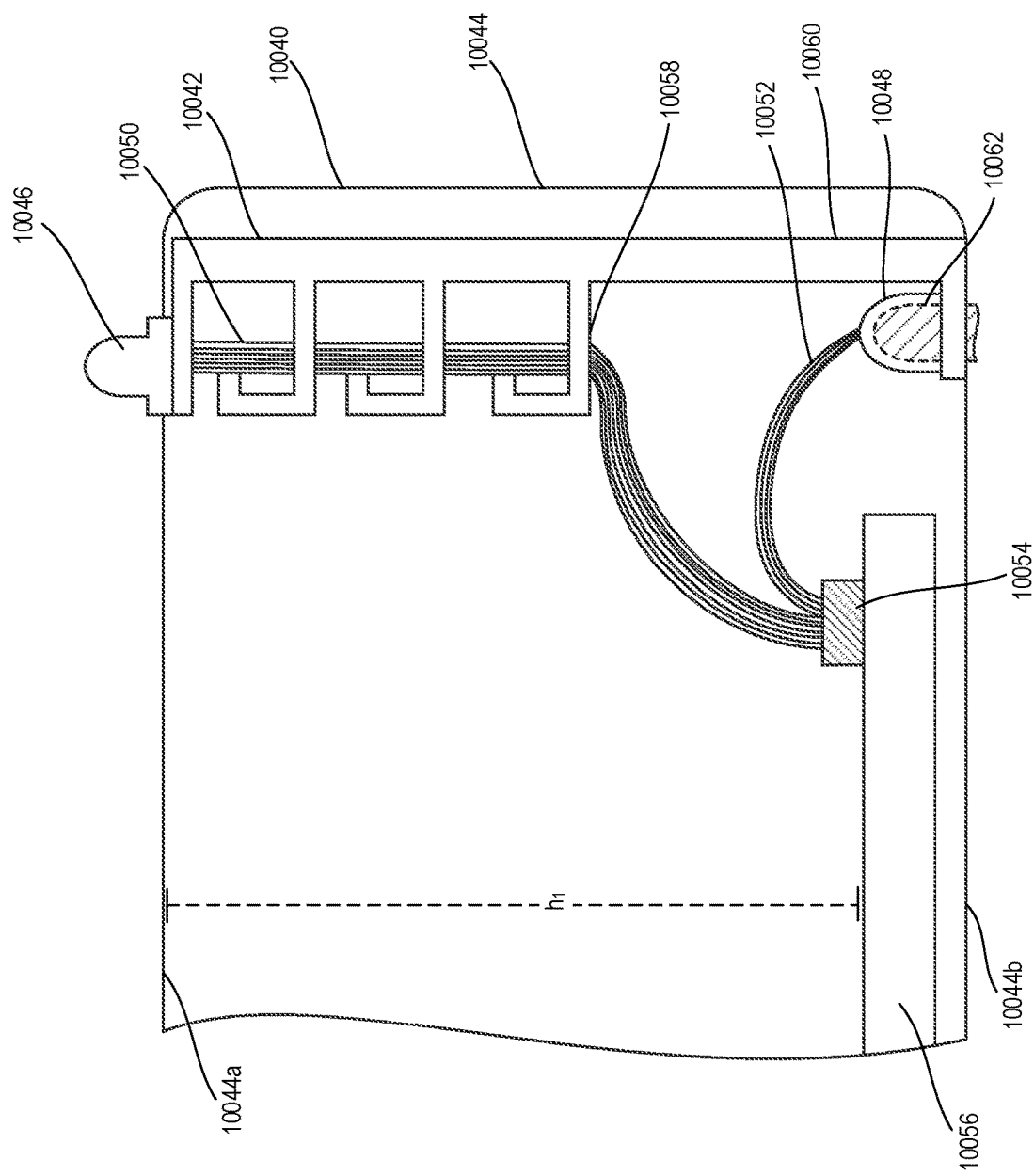
FIG. 33 illustrates a module of a modular energy system, which includes a rigid wire harness, in accordance with at least one aspect of the present disclosure, in accordance with at least one aspect of the present disclosure.

Referring now to FIG. 33, a separate aspect of a module 10040 is shown. The module 10040 illustrated in FIG. 33 is similar in many respects to the second module 10004 shown and described in FIGS. 30-32. However, instead of a flexible wire harness, a rigid wire harness 10042 is utilized. The rigid wire harness 10042 can be sized and configured to stand between a top surface 10044a of an enclosure 10044 of the module 10040 and a bottom surface 10044b of the enclosure 10044 of the module 10040. The rigid wire harness 10042 can extend the full, or at least substantially the full, height, $h_1$, of the module 10040. Further, the upper and lower bridge connectors, 10046 and 10048, are operably coupled (e.g., directly mated) to the rigid wire harness 10042 rather than to the enclosure 10044 of the module 10040. In at least one example, the upper and lower bridge connectors, 10046 and 10048, are integrated with the rigid wire harness 10042.

In the example of FIG. 33, upper wires 10050 extend from a board connector 10054 on the PCB 10056, along the rigid wire harness 10042, and connect to the upper bridge connector 10046. In addition, lower wires 10052 extend from the board connector 10054 and connect to the lower bridge connector 10048. The lower bridge connector 10048 includes a recess 10062 that is shaped and configured to receive an upper bridge connector from a separate module.

A series of holding members 10058 can extend from the rigid wire harness 10042, which are configured to wrap, or at least partially wrap, around the upper wires 10050 to support the upper wires 10050 within a predetermined distance from the rigid wire harness 10042. In the example of FIG. 33, the holding members 10058 extend from a backbone column 10060 that supports the upper and lower bridge connectors, 10046 and 10048.

The ability to mate the rigid wire harness 10042 with the upper bridge connector 10046 and lower bridge connector 10048 provides a distinct advantage when assembling the module 10040. As the rigid wire harness 10042 is one piece and extends the full, or at least substantially the full, height, $h_1$, of the module 10040, the rigid wire harness 10042 can be inserted into the module 10040 during assembly of the module 10040 and stand free. Once assembled into the module 10040, the upper and lower bridge connecters, 10046, 10048, can be mated directly with the rigid wire harness 10042, thereby eliminating the need to mount the upper and lower bridge connectors, 10046, 10048, to the top and bottom surfaces, 10044a, 10044b, of the enclosure 10044, respectively, thus, reducing assembly time. The rigid wire harness 10042 can limit force applied to an enclosure 10044 of the module 10040 during assembly of a modular energy system and can reliably establish and/or maintain connections between bridge connectors.

Modular Energy Backplane Connector Internal Flex Circuit

In a general aspect, the modular energy backplane upstream connector and downstream connector may need to electrically connect to the module in an area where space is limited. In another general aspect, the electrical connection may be required to be flexible to accommodate future modules that may be different heights. In one aspect, the backplane upstream and downstream connectors can electrically connects to the module via a flex ribbon cable which is low profile and space efficient.

Figure 34:
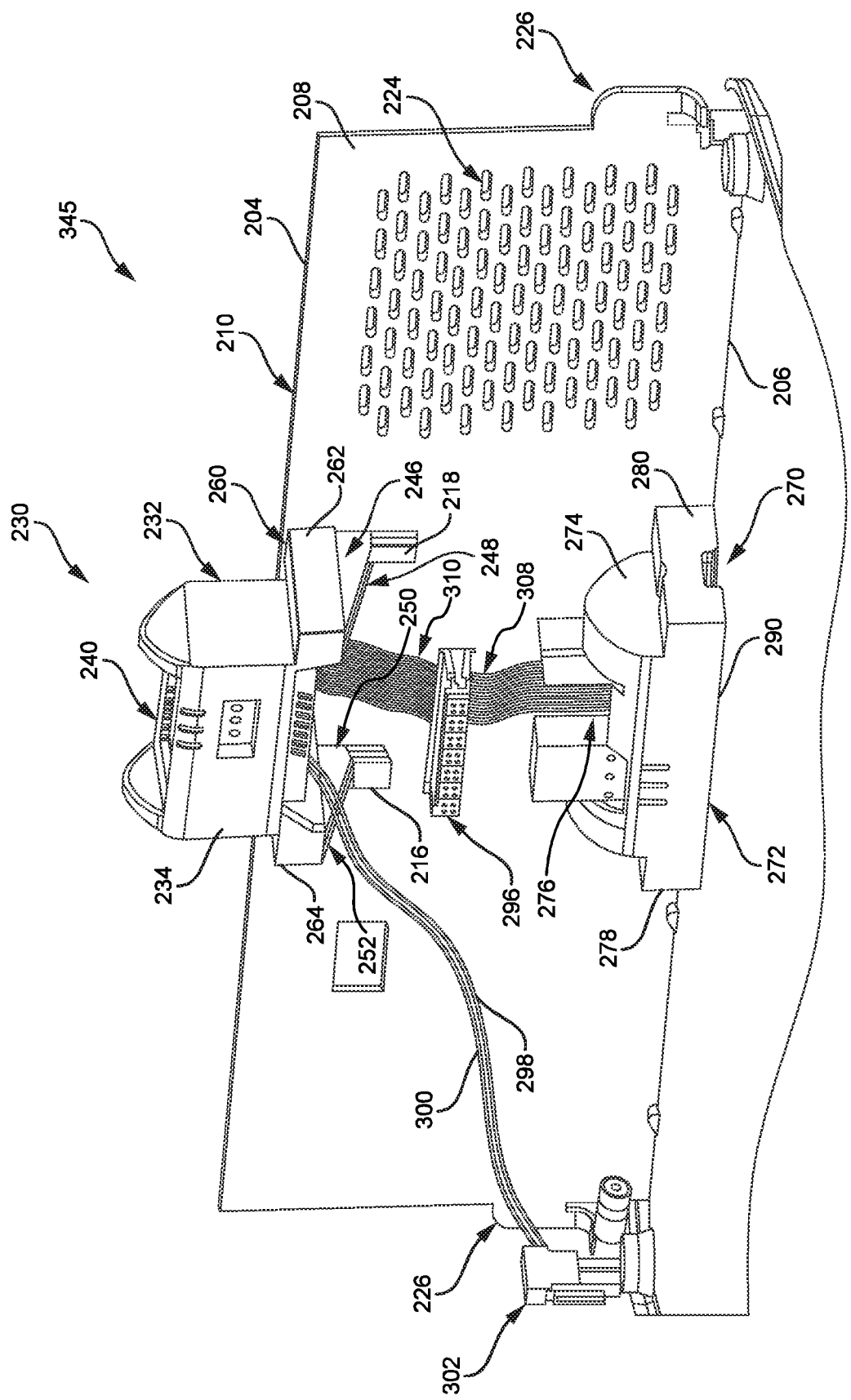
FIG. 34 is an elevated view of the backplane connector subassembly showing the connection wires as wire ribbons, in accordance with at least one aspect of the present disclosure.

In one general aspect, the backplane connector subassembly 345 may require the upstream connector 230 and downstream connector 270 to electrically connect into the main printed circuit board of the module in a way that is space efficient and flexible in height to accommodate future modules of different heights. Referring to FIG. 34, in one aspect, the signals from the upstream connector 230 may be taken to the module printed circuit board through a flexible ribbon cable 310. The signals from the downstream connector 270 may be taken to the module printed circuit board through a flexible ribbon cable 308. In one aspect, the flexible ribbon cables 310, 308 may be flexible and low profile accommodating a limited space environment. The flexibility of the flexible ribbon cables 310, 308 may allow for any additional cable length to be pushed aside in smaller sized modules. In one aspect, having additional cable length provides the needed cable length for modules of varying height.

In an alternative aspect, the module printed circuit board could be a flexible circuit with flexible cable coming off of it to attach to the upstream connector 230 and the downstream connector 270. For example, the upstream connector 230 would have flexible ribbon cable that connected to a flexible circuit board and the downstream connector 270 would have flexible ribbon cable that connected to the flexible circuit board. In one aspect, this aspect could reduce the number of electrical connections needed between the backplane and the printed circuit board, which may have the potential to reduce any possible voltage drop in the system that could occur.

Mechanical Attachment of Backplane Connector of Back Panel

In one general aspect, the modular energy backplane connector may be rigidly mounted so it can withstand abuse loads from misaligning modules while stacking. In an alternate back plane connector subassembly the upstream and downstream connectors can be attached to part of the back panel, which offers assembly benefits and eliminates the need to add additional components for mechanical mounting of the upstream connector.

Figure 35:
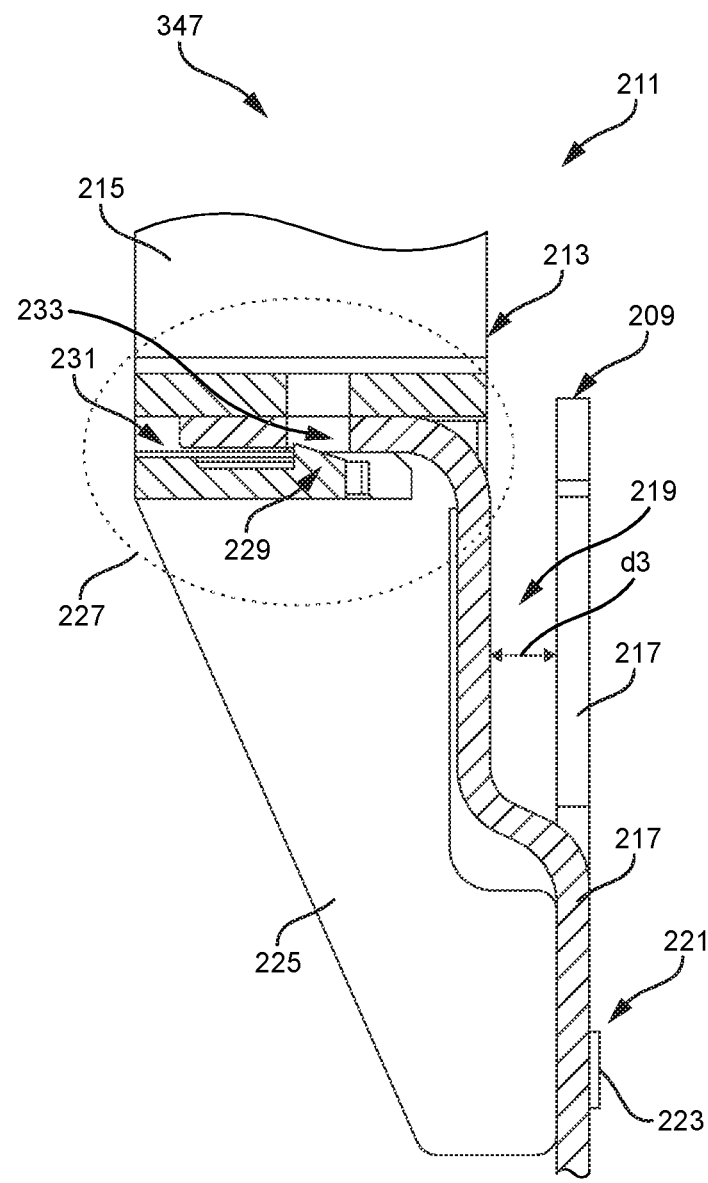
FIG. 35 is a side view of a method to connect the upstream connector to the panel of the backplane subassembly, in accordance with at least one aspect of the present disclosure.
Figure 36:
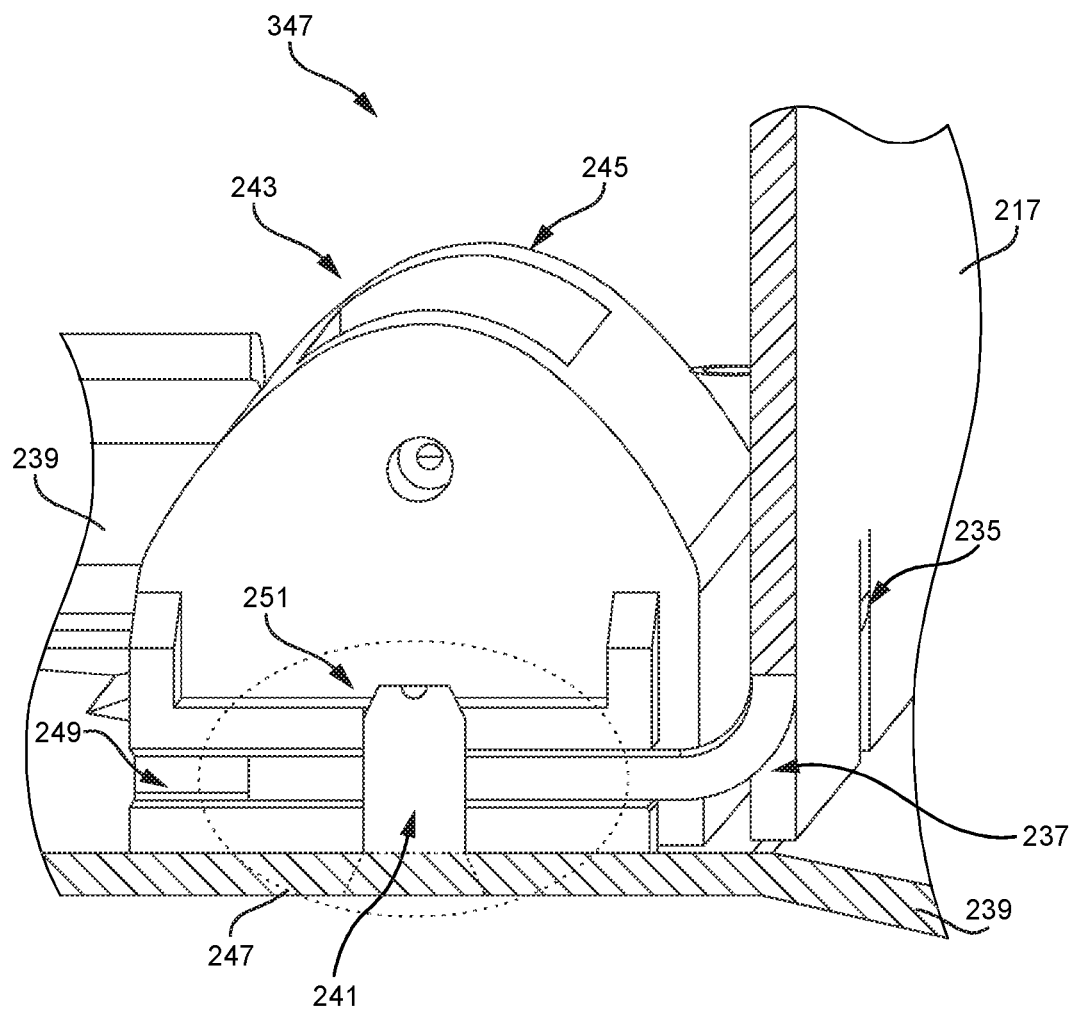
FIG. 36 is a side view of a method to connect the downstream connector to the panel of the backplane subassembly, in accordance with at least one aspect of the present disclosure.

FIGS. 35 and 36 show different views of an alternate backplane connector subassembly 347 that is substantially similar to the back plane connector subassemblies 343, 345. FIG. 35 shows an alternative upstream connector 211 that may be substantially similar to upstream connectors 200, 230. For the sake of brevity, not all of the details that are the same will be reiterated. In one aspect, upstream connector 211 may differ from the previous upstream connectors 200, 230 in how it attaches to the back panel 217. The back panel 217 may have two bent flanges 219 located toward the middle of edge 209 of the back panel 217. Referring to FIG. 35, a cross-section of the back panel 217 is shown with the cross section location being at the bent flange 219. For example, the two bent flanges 219 are located such that each one may slide along an opposing side of the upstream connector 213 to place the upstream connector 213 in the middle of the back panel 217. The back panel 217 may define a first vertical plane along the back panel. The bent flanges 219 may move away from the first plane by a distance d3 and then turn vertical along a second vertical plane. The first vertical plane and the second vertical plane may be parallel to each other. Then the bent flange may turn at an angle perpendicular to the first plane and second plane prior to reaching the edge 209, as shown in FIG. 35. The upstream connector 211 may slide onto the two bend flanges 219. For example, the upstream connector 211 may have 2 slots 231 on each side of the upstream connector 211, the two slots 231 may slide over the bend flanges 219. Each bent flange 219 may have a hole 233. In one aspect, when the bent flanges 219 slide into the slots 231 of the upstream connector the protrusions 229 snap into the holes 233, which may attach the upstream connector 211 to the back panel 217. In one aspect, the hole 233 also aligns with a hole in the upstream connector 211. In one aspect, to remove the upstream connector 211 the protrusion 229 can be pressed down and out of the hole 231 so it can be slid off of the flange 219. Circle 227 may highlight the area of FIG. 35 where the protrusion 229 snaps into the hole 233.

Referring to FIG. 35, the upstream connector 211 may contain a housing and upper portion that extends vertically past the edge 209 similarly to the upstream connectors 200, 230. The upstream connector 211 also may contain a support rib or support ribs 225 that extend down to rest against the back panel 217. The back panel 217 may contain holes 221 that are located below the bent flanges 219. Upon attaching the upstream connector 211 to the back panel 217 the support ribs 225 may come down in line with the holes 221 such that a protrusion 223 on the support rib 225 may enter the hole 221. In one aspect, the support ribs 225 resting against the back panel 217 and the protrusions 223 entering the holes 221 may provide additional mechanical support. In one aspect, there can be two support ribs 225 and two holes 221, one on each side of the upstream connector 211. In an alternate aspect, there could be any number of holes 221 and support ribs 225 that rest against them.

FIG. 36 shows an alternative downstream connector 243 that may be substantially similar to downstream connectors 254, 270. For the sake of brevity, not all of the details that are the same will be reiterated. In one aspect, downstream connector 243 may differ from the previous downstream connectors 254, 270 in how it attaches to the back panel 217. The back panel 217 may have two bent flanges 237 and 235 located toward the middle of edge of the back panel 217. Referring to FIG. 36, a cross-section of the back panel 217 is shown with the cross section location being at the bent flange 237. For example, the two bent flanges 237, 235 are located such that each one may slide into a slot in the downstream connector 243 to place the downstream connector 243 in the middle of the back panel 217. For example the flange 237 may slide into slot 249 of the downstream connector and on the opposite side of the downstream connector the flange 235 may slide into a similar slot that is not shown. The back panel 217 may then be attached to the bottom of the module enclosure 239 and a standoff 241 on the enclosure may slide into a slot 251 that is located in both the flange 237 and downstream connector 243. In one aspect the slot 251 may only be located in the downstream connector 243. On the opposing side of the downstream connector 243, there may be a similar standoff 241 that may slide into a second slot located on the flange 235 and downstream connector 243. In one aspect the second slot may only be located in the downstream connector 243. In one aspect, the standoffs 241 may allow the downstream connector to be located in the appropriate place in the bottom enclosure. Circle 247 may highlight the area of FIG. 36 where the flange 241 slides into the slot 251.

Stacking modules using the back plane connector subassembly 347 is substantially similar to the stacking of modules using the back plane connector subassembly 343, 345. For the sake of brevity, not all of the details that are the same will be reiterated. When stacking a module, the upper portion 213 of the upstream connector 211 of the lower module may enter a cavity of the downstream connector 243 located in the upper module electrically and physically connecting the two modules. In one aspect, a plug inside of the upstream connector 211 may connect with a plug inside of the downstream connector 243 to electrically connect the modules that are stacked. For example, when the modules are stacked the upper portion 213 may enter the cavity and a plug inside of the downstream connector 243 may enter a hole in the upstream connector 211 and connect with a plug inside of the upstream connector 211 to electrically connect the modules. In one aspect, the plug may be integrated into the connector assembly such that it is one molded component and not two separate components. In another aspect, the plug could be a separate component inserted into the connector. In yet another aspect, electrical pins/contacts may be integrated into the connector, for example pressed into. In one aspect, electrical wires may come down from a hole in the upstream connector 213, where the electrical wires may start at the plug inside of the upstream connector 211 and may terminate at a printed circuit board. In one aspect, electrical wires may come up from a hole 245 in the downstream connector 243, where the electrical wires may start at the plug inside of the downstream connector 243 and may terminate at a printed circuit board. Multiple modules can be stacked on top of one another no matter the height the modules. Each module may have the same upstream connector 211 and downstream connector 243, which allow the modules to be physically and electrically connected when the modules are stacked. When the modules are stacked and connected, power may transfer through the upstream connector 211 into the module and then through the downstream connector 243 to the next module lower in the stack. Electrical communications can pass through the upstream connector 211 and downstream connector 243 both ways.

Figure 37A:
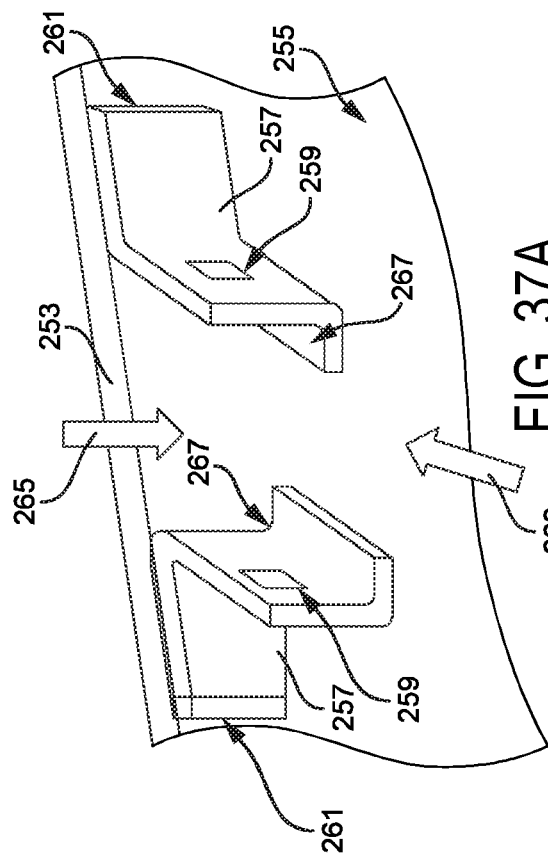
FIG. 37A is an elevated view of a method to connect the upstream and downstream connectors to a panel for the backplane connector subassembly, in accordance with at least one aspect of the present disclosure.

In various aspects, alternative methods of attaching an upstream connector and a downstream connector to a back panel are envisioned. Referring to FIG. 37A, flanges 261 could be attached to the back panel 255 such that they may be aligned or offset from edge 253 of the back panel 255. The flanges 261 may bend 257 away from the back panel 255 to provide an area between them to slide an upstream connector or downstream connector. The flanges 261 may comprise holes 259 where the upstream or downstream connector may have features that could snap into the holes 259. Similar to the protrusion 229 of upstream connector 211. The upstream or downstream connector could be slid in direction 265 until the bottom of the connector sat on the support ledges 267 and then slid in direction 263 until the connector snapped into holes 259. In one aspect, the flanges 261 could be attached to the back panel 255 by welding. In an alternative aspect, the flanges 261 could be attached to the back panel 255 by any means that would allow the mechanical support needed. In yet another aspect, the back panel 255 may require two sets of flanges 262 to be attached to allow one set to attach an upstream connector and one set to attach a downstream connector.

Figure 37B:
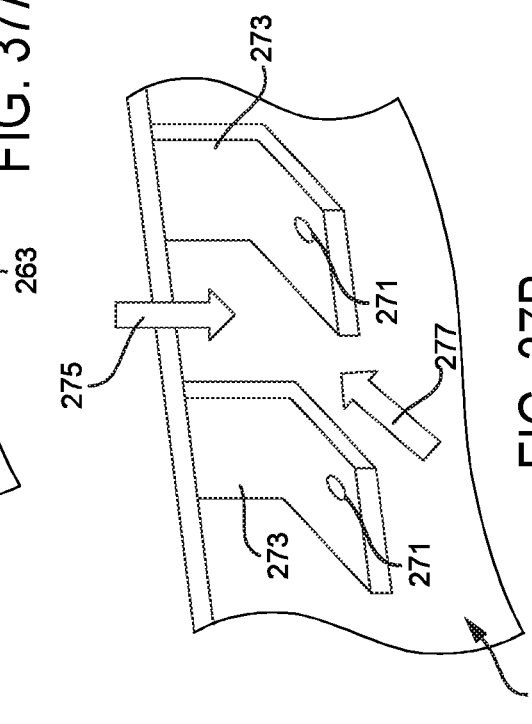
FIG. 37B is an elevated view of a method to connect the upstream and downstream connectors to a panel for the backplane connector subassembly, in accordance with at least one aspect of the present disclosure.

Referring to FIG. 37B, flanges 273 could be attached to the back panel 269 such that they may be aligned or offset from an edge of the back panel 269. The flanges 273 may be substantially similar to the flanges 261. The flanges 273 may bend away from the back panel 269 to provide an area between them to slide an upstream connector or downstream connector. The flanges 273 comprise holes 271 where the upstream or downstream connector may have features that could snap into the holes 271. Similar to the protrusion 229 of upstream connector 211. The upstream or downstream connector could be slid in direction 275 until the bottom of the connector sat on the flanges 273 and then slid in direction 277 until a feature on the connector snapped into holes 271. In one aspect, the flanges 273 could be attached to the back panel 269 by welding. In an alternative aspect, the flanges 273 could be attached to the back panel 269 by any means that would provide the mechanical support needed. In yet another aspect, the back panel 269 may require two sets of flanges 271 to be attached to allow one set to attach an upstream connector and one set to attach a downstream connector. In yet another aspect, the 2 types of flanges 273, 271 could be used together to attach an upstream connector and a downstream connector to a back panel of a module.

Figure 37C:
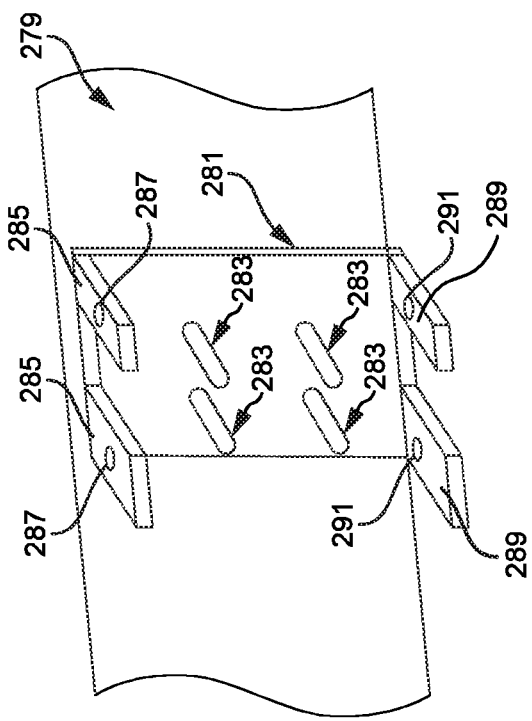
FIG. 37C is an elevated view of a method to connect the upstream and downstream connectors to a panel for the backplane connector subassembly, in accordance with at least one aspect of the present disclosure.

Referring to FIG. 37C, a panel 281 could be attached to the back panel 279 such that the panel 281 is in the middle of the back panel 279. The panel 281 may have flanges 285 located at the top of the panel 281. The flanges 285 may comprise holes 287. An upstream connector may attach to the flanges 287 in a manner similar to flanges 261 or flanges 271. For example, an upstream connector may slide onto the flanges 287 until a feature on the upstream connector snaps into the holes 287. The feature could be similar to the protrusion 229 of upstream connector 211. The panel 281 may have flanges 289 located at the top of the panel 281. The flanges 289 may comprise holes 291. A downstream connector may attach to the flanges 289 in a manner similar to flanges 261 or flanges 271. For example, a downstream connector may slide onto the flanges 289 until a feature on the downstream connector snaps into the holes 291. The feature could be similar to the protrusion 229 of upstream connector 211. In one aspect, the panel 281 could be attached to the back panel 279 by welding. In another aspect, the panel 281 could be attached to the back panel 279 by fastener inserts 283. In yet another aspect, the panel 281 could be attached to the back panel 279 by any means that would provide the mechanical support needed.

In various aspects, once the upstream and downstream connectors are attached to the back panel, the back panel connector subassembly may work substantially similar to back panel connector subassemblies 343, 345, 347. Stacking of modules may electrically and physically connect the modules and the module height may vary between the modules being stacked. In one aspect, the upstream and downstream connectors may be interchanged between the backplane connector subassemblies and still connect properly. For example, a module with backplane connector subassembly 343 my connect with a module that has the backplane connector subassembly 345 or backplane connector subassembly 347. In an alternative aspect, the modules may only connect with modules that contain the same backplane connector subassembly.

Using Enclosures to Fasten Backplane

In various general aspects, the backplane connector subassembly may be integrated to the system in a robust mechanical manner with the ability to withstand substantial mechanical forces pressing downward on the connector. In one aspect, another consideration is to create a design that does not add complexity of assembly or additional parts such as screws etc. In yet another aspect, another consideration is to provide a solution that enables flexibility of attachment that accounts for varying heights of modules.

In various general aspects, the modular energy system features a backplane connector subassembly that supplies communication and power to the modules in the system. For example, one aspect for integrating the backplane into mechanical architecture is to create a backplane subassembly similar to a cartridge style design such it attaches to the lower enclosure. In one aspect, this could be implemented by attaching the backplane subassembly on a framework shown in FIG. 38, or by snapping features in the subassembly into tabs on the lower enclosure shown in FIG. 39.

In various general aspects, both aspects would enable ease and simplicity of assembly by eliminating any additional assembly parts such as screws etc. In various aspects, the backplane connector subassembly cartridge design would enable use of this design in a modular system provided modules were similar in height or that the cartridge height could be extended or reduced.

Figure 38:
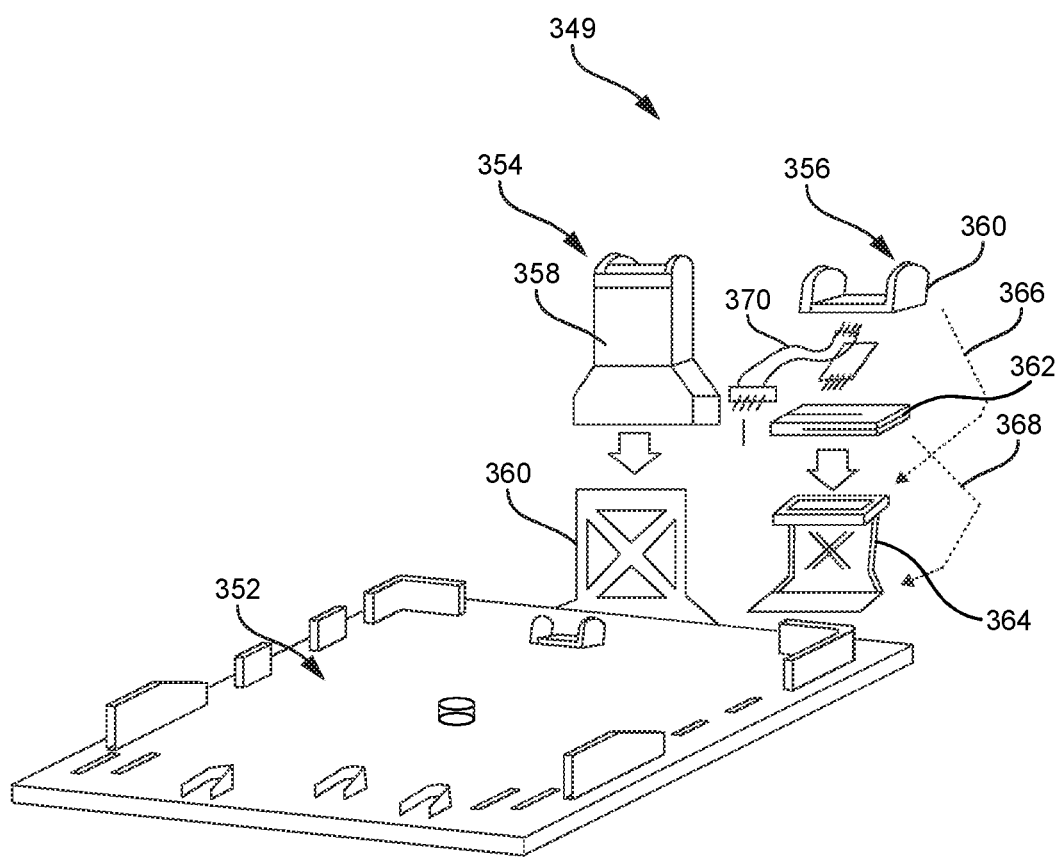
FIG. 38 is an elevated view of a cartridge system to allow a backplane connector to be connected to a module, in accordance with at least one aspect of the present disclosure.

Referring to FIG. 38, a cartridge style back plane connector subassembly 349 is shown. FIG. 38 illustrates 2 cartridge style back plane connectors 354, 356. In one aspect, both cartridge style back plane connectors 354, 356 may connect to the bottom 352 of the module enclosure. In back plane connector 354, a framework 360 may be attached to the bottom 352 of the module enclosure. In one aspect, the cartridge style connector 358 of the back plane connector 354 is in one piece and slides on to the framework 360 to attach the cartridge style connector 358 to the bottom 352 of the enclosure. When the cartridge style back plane connectors 354 is assembled and attached to the bottom 352 of the lower enclosure, then the top of the cartridge style connector 358 may extend outside of the top of the module enclosure, not shown. To accommodate varying heights of modules, the height of the components in the cartridge style backplane connector 354 may vary based on the height of the module.

Still referring to FIG. 38, an alternate cartridge style backplane connector 356 is shown, where the backplane connector 356 is in multiple pieces. For example lower portion 364, middle portion 362, and upper portion 356. The lower portion 364 may connect to a framework on the bottom 352 of the enclosure. The middle portion 362 may attach to the lower portion as indicated by arrow 368. The upper portion may attach to the lower portion as indicated by arrow 366. When the cartridge style back plane connectors 356 is assembled and attached to the bottom 352 of the lower enclosure, then the upper portion 360 may extend outside of the top of the module enclosure, not shown. To accommodate varying heights of modules, the height of the components in the cartridge style backplane connector 356 may vary based on the height of the module.

Modules using the cartridge style back plane connector subassembly 349 can stack in a substantially similar manner to the back plane connector subassemblies 343, 345, 347. For example, the stacking of the modules has the top portion of the connector in the lower module enter the lower portion of the connector in the upper module. Stacking of modules may electrically and physically connect the modules and the module height may vary between the modules being stacked.

Figure 39:
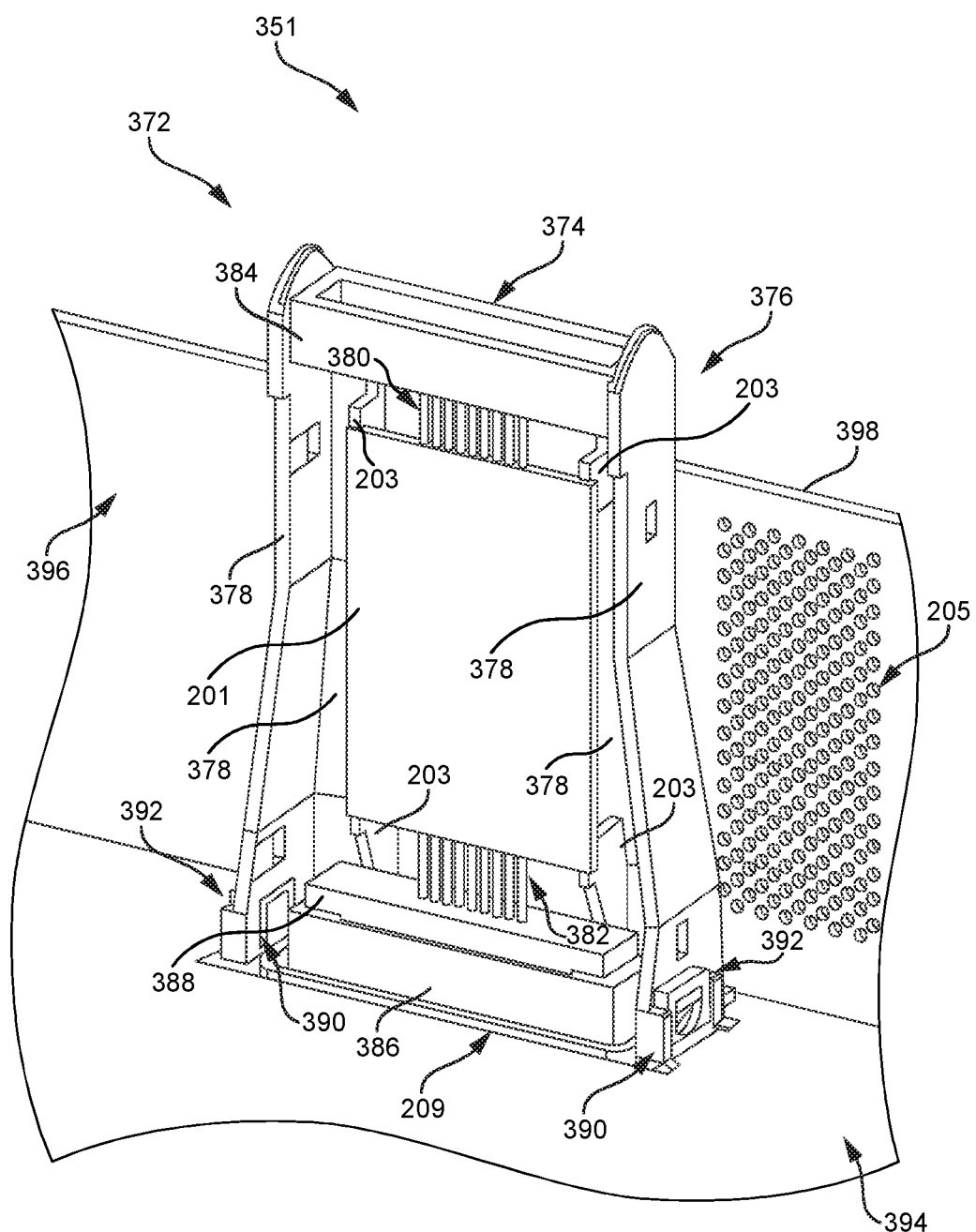
FIG. 39 is an elevated view of a backplane connector that snaps into the bottom of the module enclosure, in accordance with at least one aspect of the present disclosure.

Referring to FIG. 39, a cartridge style back plane connector subassembly 351 is shown. The cartridge 372 of the cartridge style back plane connector subassembly 351 may attach to the bottom 394 of the enclosure. In one aspect, the attachment may be made by snapping features 290 on the cartridge 372 that snap into tabs 392 on the bottom 394 of the enclosure. The snapping features 290 are located at the bottom of frame 378. The frame 378 may run the length of the cartridge 378 on either side of the cartridge 372. The bottom of the cartridge 378 may have a first connector enclosure 386 that may extend into an enclosure 209 that can receive a connection from a cartridge of a lower module. The frame 378 may contain protrusions 203 that can hold a printed circuit board 201. A plug 388 may be connected to the first connector enclosure 386 and electrical wires can extend from the plug 388 to the circuit board 201. The electrical wires 380 extend away from the circuit board 201 and into a plug located in the second connector enclosure 384. The hole 374 in the second connector enclosure 380 allows a plug from a module higher in the stack to connect with the plug located in the second connector enclosure 384 of the current module. The back panel 396 of the current module may comprise vent holes 205 to allow air flow into the module. When the cartridge 372 is connected to the bottom 394 of the enclosure, the cartridge 372 extends vertically past the edge 398 of the back panel such that the upper portion 376 of the cartridge 372 extends outside of the module. To accommodate varying heights of modules, specific cartridges 273 of varying heights can be created to account for the varying heights of the module.

Modules using the cartridge style back plane connector subassembly 351 can stack in a substantially similar manner to the back plane connector subassemblies 343, 345, 347, 349. For example, the staking of the modules may have an upper portion 376 of the back plane connector in the lower module enter the lower portion of a back plane connector in the upper module. Stacking of modules may electrically and physically connect the modules and the module height may vary between the modules being stacked.

Using Crush Ribs to Capture Backplane Housing

In various general aspects, the modular energy system features a backplane that supplies communication and power to the modules in the system. In one aspect, the backplane may be integrated to the system in a robust mechanical manner with the ability to withstand substantial mechanical forces pressing downward on the connector. In another aspect, another consideration is to create a design that does not add complexity of assembly or additional parts such as screws etc. In yet another aspect, another consideration is to provide a solution that enables flexibility of attachment that accounts for varying heights of modules.

One aspect for integrating the backplane connector into the mechanical architecture may be to utilize the pre-existing interface of a crush ribs. In various aspects, crush ribs are protruding features that are added to an injection molding design to aid in the stability of a press-fit connection. These structures are used in holes or other components into which another part may be press-fit. For plastic crush rib design, crush ribs may define either a pointed or rounded form. In one aspect, crush ribs may be formed of a foam like material with high tolerances, and the thixoformed enclosure to sandwich the upstream and downstream connectors between the crush ribs and enclosure. This process could be implemented by adding crush ribs and guide bosses in the crush ribs to secure and fix the backplane connector. This aspect would eliminate any complex assemble features or additional components for assembly purposes (such as screws, etc.), and allow for a similar implementation among all modules in the system.

Figure 40:
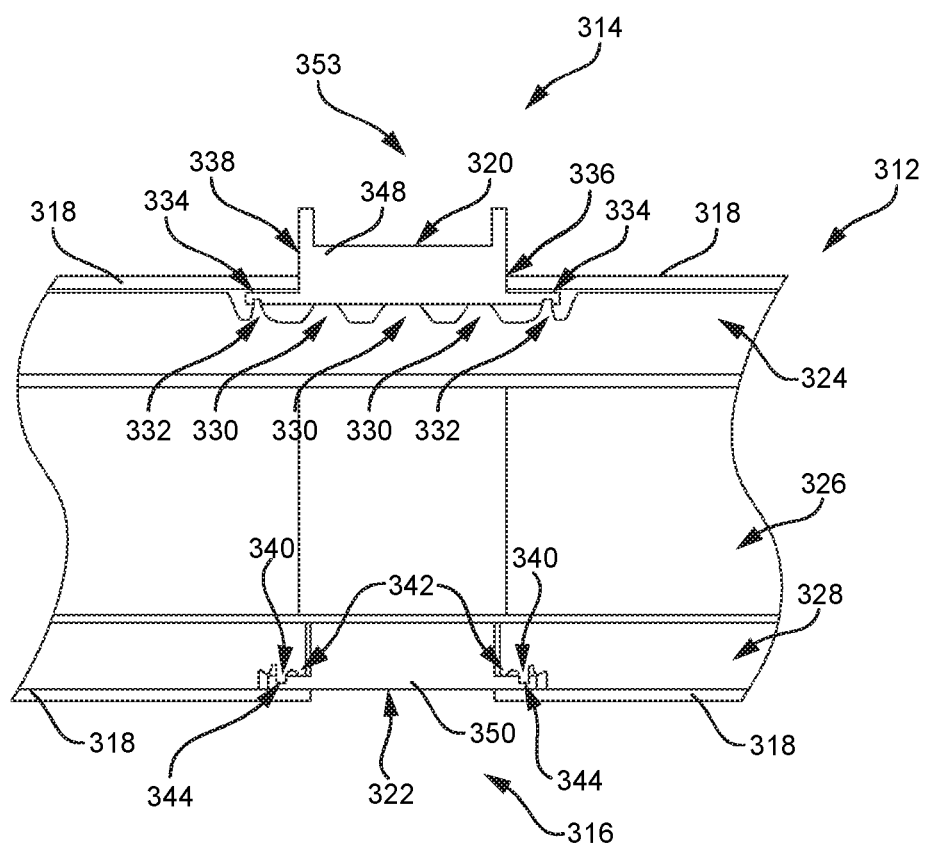
FIG. 40 is a front view of a backplane connector subassembly that is built into a module enclosure, in accordance with at least one aspect of the present disclosure.
Figure 41:
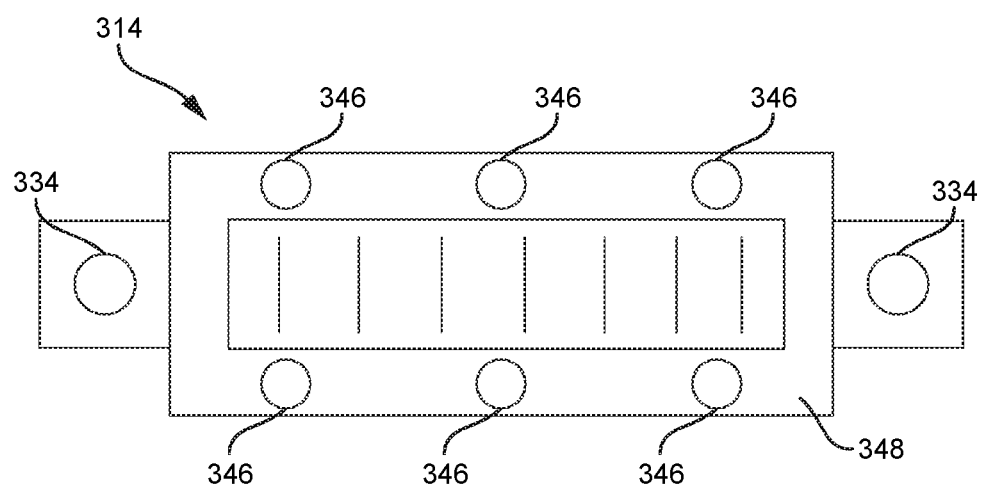
FIG. 41 is a bottom view of the upstream connector shown in FIG. 18, in accordance with at least one aspect of the present disclosure.

Referring to FIGS. 40 and 41, a back plane connector subassembly 353 is shown. In one aspect, the crush rib 312, which is a foam like material with high tolerances, sits inside of the back of the enclosure 318. The crush rib may be viewed as broke up into 3 sections a top crush rib 324, a middle crush rib 326, and a lower crush rib 328. The upstream connector 314 may be slid between the crush rib 312 and the top of the enclosure 318. The upstream connector 314 may be similar in many aspects to upstream connectors 211, 230, 200. For the sake of brevity, not all of the details that are the same will be reiterated. The upstream connector 314 rests on top of the crushed ribs 330 of the crush rib 312. The upstream connector 314 may be placed on the crushed ribs 330 so that the alignment bosses 332 of the crush rib 312 enter into the guide holes 334 on the upstream connector 314. FIG. 41 illustrates the bottom of the upstream connector 314. Referring primarily to FIG. 41, the guide holes may be located on either side of the housing 348 of the upstream connector 314 and the indents 346 may be touch points for the crushed ribs 330. A hole 320 may be the location where electrical component can pass information and power between the modules. For example, a plug that may be located inside of the hole 320, where the plug can connect the upstream connector with a downstream connector of another module that may be stacked on top of the current module.

Referring to FIG. 40, the downstream connector 316 may be slid between the crush rib 312 and the bottom of the enclosure 318. The downstream connector 316 may be similar in many aspects to downstream connectors 254, 270, 234. For the sake of brevity, not all of the details that are the same will be reiterated. The downstream connector 316 may rest on the bottom of the enclosure 318 with crushed ribs 342 of the crush rib 312 holding the downstream connector 316 against the enclosure 318. The downstream connector 316 may be placed in the correct location by sliding the guide holes 344 on to the alignment bosses 340. The downstream connector may comprise a housing 350 that contains a cavity 322 that is made to receive an upper portion 338 of an upstream connector during stacking of modules.

Modules using the back plane connector subassembly 353 can stack in a substantially similar manner to the back plane connector subassemblies 343, 345, 347, 349, 351. For example, when stacking a module, the upper portion 338 of the upstream connector 314 of the lower module may enter a cavity 322 of the downstream connector 316 located in the upper module electrically and physically connecting the two modules. In one aspect, a plug inside of the upstream connector 314 may connect with a plug inside of the downstream connector 316 to electrically connect the modules that are stacked. For example, when the modules are stacked the upper portion 338 may enter the cavity 322 and a plug inside of the downstream connector 316 may enter the hole 320 and connect with a plug inside of the upstream connector 338 to electrically connect the modules. In one aspect, the plug may be integrated into the connector assembly such that it is one molded component and not two separate components. In another aspect, the plug could be a separate component inserted into the connector. In yet another aspect, electrical pins/contacts may be integrated into the connector, for example pressed into. In one aspect, electrical wires may start at the plug inside of the upstream connector 338 and terminate at a printed circuit board in the module. In one aspect, similarly, electrical wires may start at the plug inside of the downstream connector 316 and terminate at a printed circuit board in the module. Multiple modules can be stacked on top of one another no matter the height the modules. Each module may have the same upstream connector 314 and downstream connector 316, which allow the modules to be physically and electrically connected when the modules are stacked. When the modules are stacked and connected, power may transfer through the upstream connector 338 into the module and then through the downstream connector 316 to the next module lower in the stack. Electrical communications can pass through the upstream connector 314 and downstream connector 316 both ways.

Back Panel Support of Backplane

In various general aspects, the modular energy system backplane assembly requires a connector out both the top and bottom with a wire harness in the middle. In one aspect, the design and assembly can be complicated based on the requirements.

In one aspect of a back plane subassembly, ribs may be added to the back panel that stick out to support both the downstream and upstream connectors back plane subassembly. The bottom enclosure may be used to locate the downstream connector and then the back panel may be placed over the top to secure the downstream connector in place. The upstream connector may be placed on the back panel ribs and then the whole assembly could be sandwiched together by the top enclosure. In one aspect, this process eliminates the need for screws into the two enclosures and ensures a robust backplane connector with a simplistic design.

Figure 42:
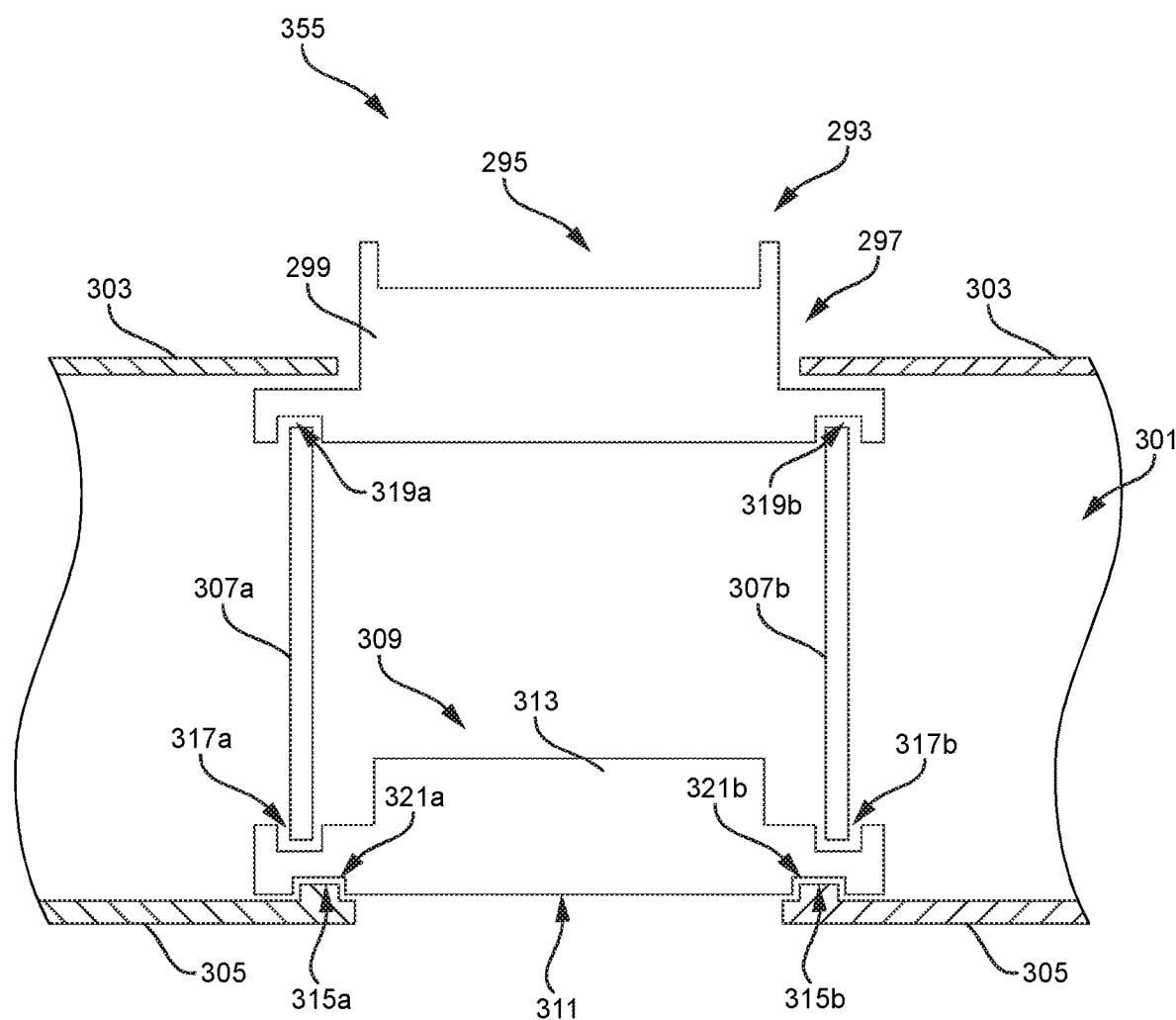
FIG. 42 is a front view of a backplane connector subassembly that is built into a module enclosure, in accordance with at least one aspect of the present disclosure.

Referring to FIG. 42, a back plane connector subassembly 355 is shown. In one aspect, the upstream connector 293, support ribs 307a, 307b, and downstream connector 309 may be sandwiched together inside of the enclosure bottom 305 and enclosure top 303. The upstream connector 293 and the downstream connector 309 may be-similar to upstream connectors 211, 230, 200, 314 and downstream connectors 254, 270, 234, 316. For the sake of brevity, not all of the details that are the same will be reiterated. The downstream connector 309 may comprise a housing 313 and a cavity 311 and the upstream connector 293 may comprise a housing 299, an upper portion 297, and a hole 295. The downstream connector 309 may rest on the enclosure bottom 305. In one aspect, the downstream connector 309 may be placed so that protrusions 315a, 315b of the enclosure bottom 305 rest inside holes 321a, 321b of the downstream connector 309. Support ribs 307a, 307b may be attached to the back panel 301. The back panel 301 may be placed against the enclosure bottom 305 so that the support ribs 307a, 307b may rest on top of indents 317a, 317b of the downstream connector 309. The upstream connector 293 may rest on the support ribs 307a, 307b so that the support ribs 307a, 307b rest inside of holes 319a, 319b of the upstream connector 293. The enclosure top 303 may rest against the upstream connector 293 to keep the back plane connector subassembly 355 together. Varying heights in modules may be accommodated by attaching support ribs 307a, 307b that are an appropriate length to account for the height of the module.

Modules using the back plane connector subassembly 355 stack in a substantially similar manner to the back plane connector subassemblies 343, 345, 347, 349, 351, 353. For example, when stacking a module, the upper portion 297 of the upstream connector 293 of the lower module may enter a cavity 311 of the downstream connector 309 located in the upper module electrically and physically connecting the two modules. In one aspect, a plug inside of the upstream connector 293 may connect with a plug inside of the downstream connector 309 to electrically connect the modules that are stacked. For example, when the modules are stacked the upper portion 297 may enter the cavity 311 and a plug inside of the downstream connector 309 may enter the hole 295 and connect with a plug inside of the upstream connector 293 to electrically connect the modules. In one aspect, the plug may be integrated into the connector assembly such that it is one molded component and not two separate components. In another aspect, the plug could be a separate component inserted into the connector. In yet another aspect, electrical pins/contacts may be integrated into the connector, for example pressed into. In one aspect, electrical wires may start at the plug inside of the upstream connector 293 and terminate at a printed circuit board in the module. In one aspect, similarly, electrical wires may start at the plug inside of the downstream connector 309 and terminate at a printed circuit board in the module. Multiple modules can be stacked on top of one another no matter the height the modules. Each module may have the same upstream connector 293 and downstream connector 309, which allow the modules to be physically and electrically connected when the modules are stacked. When the modules are stacked and connected, power may transfer through the upstream connector 293 into the module and then through the downstream connector 309 to the next module lower in the stack. Electrical communications can pass through the upstream connector 293 and downstream connector 309 both ways.

Isolating Features in a Modular System

In various general aspects, in a modular capital system power may be distributed through a common backplane interface. In the modular energy system, the main power supply may be in the Header Module which can distribute 60V DC to downstream modules. This architecture may be designed to reduce the number of AC power cords in the OR. The system may be only as extensible as the AC power coming from the walls. External standards and known variation by country limit this to approximately 12A and approximately 1200 watts per power cord. A solution may be needed to add additional power supplies while meeting external standards once 1200 watts is exceeded.

In one aspect, a module may be added to the stack of modules that can supply additional power. For example a "power module" can be added to the stack which has an additional 1200 W AC to DC power supply that can provide back plane power. In one aspect, to add a power module to the modular energy system, its power domain may be required to be isolated from the Header module's power domain as well as the domain of any upstream modules. By having the largest possible power supply (1200 W) the power module may power itself, as well as other downstream modules. In one aspect, the power module could be a stand-alone module that provides power, or it could be a module that provides some other clinical function as well, such as Visualization, Smoke Evac/Insufflation, Fluid Management, etc.

Figure 43:
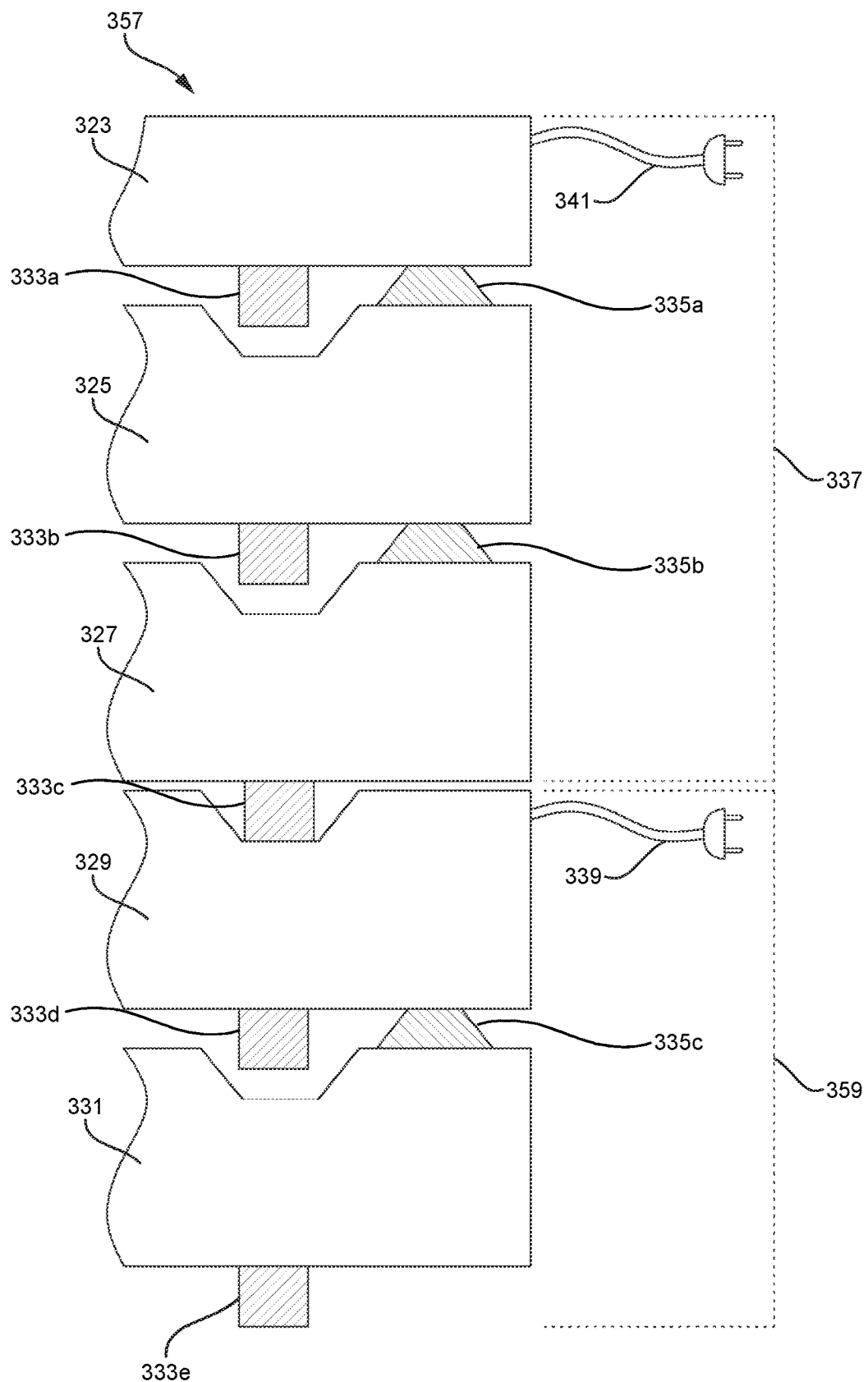
FIG. 43 illustrates a modular energy system that contains a power module, in accordance with at least one aspect of the present disclosure.

FIG. 43 illustrates a cross-section of a corner of a modular energy system 357. The modular energy system 357 may comprise a header module 323 that can provide power to any module below it in the module stack. For example, the header module 323 may provide power to a first generator module 325 and a second generator module 327. The header module 323 may comprise a power cable 341 that may bring power to the header module 323. The modular energy system 357 may also comprise a power module 329 that can provide power to any module below it in the module stack. For example, the power module 329 may provide power to a future module. In one aspect, the future module 331 could be another generator module. In another aspect the future module could be any type of module. The power module 329 may comprise a power cable 339 that may bring power to the power module 329. In one aspect, the power cable 339 and the power cable 341 may be required to be connected to separate branch circuits. All the modules in the modular energy system 357 comprise rubber isolating feet at the bottom corners of the modules. For example, modules 323, 325, 327, 329, 331 in the modular energy system 357 may have rubber isolating feet 333a-e at the bottom corners of the modules. Modules that require power from an upstream module may have metal grounding pads attached to the top corners. For example, the modules 325, 327, 331 may have metal grounding pads 335a-c attached to the top corners. In one aspect, the metal grounding pads make contact with the module stacked above them so that the isolating feet do not make contact. In one aspect, metallic grounding feet may not be present on the top surface of the power module such that the rubber isolating feet 333c of the module upstream of the power module make contact, which provides an isolation distance between the power domain of the header module 323 and the power domain of the power module 329.

In the modular energy system 357 there may be multiple power domains. For example, the header module has a first power domain 337 and the power module has a second power domain 359. The two power domains 337, 359 may be isolated by the rubber isolating feet 333c making contact the with the last module in the first power domain 337 and the first module in the second power domain 359. The last module in the first power domain 337 may be the second generator module 327 and the first module in the second power domain 359 may be the power module 329. Modules that require power from an upstream module may have a metal grounding pad attached to the top corners. The metal grounding pads may rest against the modules above and below the grounding pad providing a common ground between the modules in the power domain. In one aspect, the metal grounding pad of the module below may keep the rubber isolating feet of the module above from resting on the module below. For example, the metal grounding pads 335b may lift the first generator module 325 so that the rubber isolating feet 333b do not rest against the second generator module 327 and the first generator module 325 may rests solely on the metal grounding pads 335b.

In the modular energy system 357 power may flow through the power cords 341, 339 to their respective power domains 337, 359. Power may flow into the header module 323 and then may be provided down the stack to the first generator module 325 and the second generator module 327. Power and communication electrical wires may begin at the header module 323 and go into a downstream connector of the header module 325 that is connected to an upstream connector of the first generator module 325. The power and communication electrical wires may then continue into the first generator module 325 from the upstream connector of the first generator module 325. The power and communication electrical wires may then continue from the first generator module 325 into a downstream connector of the first generator module 325 that is connected to an upstream connector of the second generator module 327. The power and communication electrical wires may then continue into the second generator module 327 from the upstream connector of the second generator module 327. The power and communication electrical wires may then continue from the second generator module 327 into a downstream connector of the second generator module 327 that is connected to an upstream connector of the power module 329. The communication electrical wires may then continue from the upstream connector of the power module 329 and into the power module 329. The upstream connector of the power module 329 may only contain communication electrical wires and no power electrical wires. Power electrical wires may enter the power module 329 through the power cord 339. Power electrical wires may start at the power module 329 and go to the downstream connector of the power module 329. The communication electrical wires may continue from the power module 329 and go to the downstream connector of the power module 329. The downstream connector of the power module 329 may be connected to the upstream connector of the future module 331. The power and communication electrical wires may continue from the upstream connector of the future module 331 into the future module 331. If more modules were connected below the future module 331, then the power and communication electrical wires may continue in a similar manner to that described above.

The communication electrical wires connect all the modules in the modular energy system 357 and the communication electrical wires are isolated between the modules. The first and second generator modules 325, 327 may be power by the header module 323 and have metal grounding pads 335*a*, 335*b* to maintain a common ground with the header module 323. The future module 331 may be power by the power module 329 and may have metal grounding pads 335*c* to maintain a common ground with the power module 329. The power module 329 may not have a metal grounding pad and the rubber isolating feet 333*c* make contact between the power module 329 and second generator module 327. The contact of the rubber isolating feet 333*c* may provide an isolation distance between the first power domain 337 and the second power domain 359.

In this aspect modules are either independent or dependent. Independent modules may have their own power supply and pass power through their downstream backplane connector. For example, the header module 323 and the power module 329 may be independent modules. Independent modules may not have power lines in their upstream connector. In one aspect, the power passed through their downstream backplane connector may be 60V DC. In another aspect, the power passed through their downstream backplane connector may be any voltage of power not exceeding electrical limitations. Dependent modules may receive their power through the modules above it through the upstream backplane connector and may have the ability to pass that power to the module below via the downstream backplane connector. For example, the first generator module 325, the second generator module 327, and the future module 331 are dependent modules.

EXAMPLES

Various aspects of the subject matter described herein are set out in the following numbered examples.

Example 1. A modular energy system that comprises a first module, comprising a first panel, and a first connector attached to the first panel. A portion of the first connector extends past a first edge of the first panel. The modular energy system further comprises a second module, comprising a second panel, and a second connector attached to the second panel. The second connector is aligned with a second edge of the second panel, and the second connector defines a cavity. The second module is coupled to the first module, wherein the portion of the first connector that extends past the first edge of the first panel is positioned within the cavity defined by the second connector.

Example 2. The modular energy system of Example 1, further comprising a third module, comprising a third panel and a third connector attached to the third panel. The third connector is aligned with a third edge of the third panel and the third connector defines a second cavity. The second module further comprises a fourth connector attached to the second panel, wherein a portion of the fourth connector extends past a fourth edge of the second panel. The fourth edge of the second panel is opposite the second edge of the second panel. The third module is coupled to the second module, wherein the portion of the fourth connector that extends past the fourth edge of the second panel is positioned within the second cavity of the third connector.

Example 3. The modular energy system of Example 2, wherein the first, second, and third modules can be different sizes.

Example 4. The modular energy system of any one or more of Examples 1 through 3, wherein the first panel comprises a first support member attached to and extending away from the first panel. The first connector further defines a first hole in the first connector. The first connector is slidably attachable to the panel, wherein the first support member is slidably receivable into the first hole defined by the first connector.

Example 5. The modular energy system of Example 4, wherein the first panel further comprises a support ledge attached to the panel, wherein the support ledge is offset from the first support member. The first connector further comprises a support rib that extends away from the first connector, and wherein the support rib is configured to rest against the support ledge in a configuration defined by the first connector attached to the first panel.

Example 6. The modular energy system of Example 4, wherein the first panel further comprises a second support member attached to and extending away from the first panel, wherein the second support member is offset from the first support member. The second connector further defines a second hole in the second connector. The second connector is slidably attachable to the first panel, wherein the second support member is slidably receivable into the second hole defined by the second connector.

Example 7. The modular energy system of any one or more of Examples 1 through 6, wherein in the coupled configuration, the first module and the second module are physically and electrically connected.

Example 8. The modular energy system of any one of Examples 4 through 7, wherein the first support member comprises a fastener insert.

Example 9. The modular energy system of Example 5, wherein the support rib comprises multiple support ribs extending away from the first connector.

Example 10. A modular energy system, comprising a first module. The first module comprises a first panel. The first panel comprises a first support member attached to the panel, and a second support member attached to the panel, wherein the second support member is offset from the first support member. The first panel further comprises a support ledge attached to the first panel, wherein the support ledge is located between the first support member and the second support member. The first module further comprises a first connector, defining a first hole in the first connector. The first connector comprises a support rib that extends away from the first connector. The first connector is slidably attachable to the first panel, wherein the first support member is slidably insertable into the first hole. In the attached configuration, the support rib is configured to rest against the support ledge. In the attached configuration, a portion of the first connector extends past a first edge of the first panel. The first module further comprises a second connector defining a cavity and a second hole. The second connector is slidably attachable to the first panel, wherein the second support member is slidably receivable into the second hole. In the attached configuration the second connector is aligned with a second edge of the first panel, wherein the second edge of the first panel is opposite the first edge of the first panel.

Example 11. The modular energy system of Example 10, further comprising a second module. The second module comprises a second panel. The second panel comprises a third support member attached to the second panel, a fourth support member attached to the second panel, wherein the fourth support member is offset from the third support member. The second panel further comprises a second support ledge attached to the second panel, wherein the support ledge is located between the third support member and the fourth support member. The modular energy system further comprises a third connector defining a third hole in the third connector. The third connector comprises a second support rib that extends away from the third connector. The third connector is slidably attachable to the second panel, wherein the third support member is slidably receivable into the third hole define by the third connector. In the attached configuration, the second support rib is configured to rest against the second support ledge. In the attached configuration, a second portion of the third connector extends past a third edge of the second panel. The modular energy system further comprises a fourth connector defining a second cavity and a fourth hole in the fourth connector. The fourth connector is slidably attachable to the second panel, wherein the fourth support member is slidably receivable into the fourth hole defined by the fourth connector. In the attached configuration, the second connector is aligned with a fourth edge of the second panel, and wherein the third edge is opposite the fourth edge.

Example 12. The modular energy system of Example 11, wherein the first module is coupled to the second module, and in the coupled configuration the second portion of the third connector that extends past the second panel is positioned within the cavity defined by the second connector.

Example 13. The modular energy system of Example 11, wherein the second module is coupled to the first module, and in the coupled configuration the portion of the first connector that extends past the first panel is positioned within the cavity defined by the fourth connector.

Example 14. The modular energy system of any one or more Examples 11 through 13, wherein in the coupled configuration, the first module and the second module are physically and electrically connected.

Example 15. A module for a modular energy system, the module comprises a panel. The panel comprises a first support member attached to and extending away from the panel, a second support member attached to and extending away from the panel, wherein the second support member is offset from the first support member. The module further comprises a first connector defining a first hole in the first connector. The first connector is slidably attachable to the panel, wherein the first support member is slidably receivable into the first hole. In the attached configuration a portion of the first connector extends past a first edge of the panel. The module further comprises a second connector defining a cavity and a second hole. The second connector is slidably attachable to the first panel, wherein the second support member is slidably receivable into the second hole. In the attached configuration the second connector is aligned with a second edge of the panel, and wherein the second edge of the first panel is opposite the first edge of the panel.

Example 16. The module of Example 15, wherein the panel further comprises a support ledge attached to the panel. The support ledge is located between the first support member and the second support member. The first connector further comprises a support rib that extends away from the first connector. In the attached configuration the support rib rests against the support ledge.

Example 17. The module of any one of Examples 15 through 16, wherein the module is one of a plurality of modules and the plurality of modules are stackable by inserting the portion of a first connector that extends past one module inside the cavity defined by a second connector of another module, wherein in the stacked configuration, the plurality of modules are physically and electrically connected.

Example 18. A modular energy system that comprises a header module, wherein the header module is configured to supply power to one or more connected dependent modules. The modular energy system further comprises at least one dependent module connected to the header module and powered by the header module, and a power module connected to the dependent module, wherein the power module is configured to supply power to one or more other connected dependent modules.

Example 19. The modular energy system of Example 18, wherein the dependent module comprises grounding feet at the top corners of the dependent module, and wherein the header module rests on the grounding feet.

Example 20. The modular energy system of any one of Examples 18 through 19, wherein the dependent module comprises isolating feet at the bottom corners of the dependent module, wherein the isolating feet rest between the dependent module and the power module, and wherein the isolating feet separate the dependent module from the power module.

Example 21. The modular energy system of any one or more of Examples 18 through 20, wherein the header module and the dependent module are part of a first power domain and the power module is part of a second power domain, and wherein the first power domain is separate from the second power domain.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A modular energy system, comprising:
a first module, comprising:
a first panel comprising a first surface; and
a first connector removably attachable to the first panel and positioned against the first surface upon attachment to the first panel, wherein a portion of the first connector extends laterally past a first edge of the first surface of the first panel; and
a second module, comprising:
a second panel comprising a second surface; and
a second connector removably attachable to the second panel and positioned against the second surface upon attachment to the second panel, wherein the second connector is aligned with a second edge of the second surface of the second panel, and wherein the second connector defines a cavity,
wherein the second module is coupled to the first module in a laterally stacked configuration, wherein the portion of the first connector extending past the first edge of the first panel is positioned within the cavity defined by the second connector, wherein the first surface is aligned with the second surface in the stacked configuration, wherein the first panel comprises a first support member attached to and extending away from the first panel, wherein the first connector further defines a first hole in the first connector, wherein the first support member is slidably receivable into the first hole defined by the first connector during attachment of the first connector to the first panel, and wherein the first panel further comprises:
a support ledge attached to the first panel, wherein the support ledge is offset from the first support member,
wherein the first connector further comprises a support rib that extends away from the first connector, and wherein the support rib is configured to rest against the support ledge in a configuration defined by the first connector attached to the first panel.

2. The modular energy system of claim 1, further comprising:
a third module, comprising:
a third panel; and
a third connector attached to the third panel, wherein the third connector is aligned with a third edge of the third panel, wherein the third connector defines a second cavity;
wherein the second module further comprises:
a fourth connector attached to the second panel, wherein a portion of the fourth connector extends past a fourth edge of the second panel, wherein the fourth edge of the second panel is opposite the second edge of the second panel; and
wherein the third module is coupled to the second module, wherein the portion of the fourth connector that extends past the fourth edge of the second panel is positioned within the second cavity of the third connector.

3. The modular energy system of claim 2, wherein the first, second, and third modules can be different sizes.

4. The modular energy system of claim 1, wherein in the stacked configuration, the first module and the second module are physically and electrically connected.

5. The modular energy system of claim 1, wherein the first support member comprises a fastener insert.

6. The modular energy system of claim 1, wherein the support rib comprises multiple support ribs extending away from the first connector.

7. A modular energy system, comprising:
a first module, comprising:
a first panel comprising a first surface; and
a first connector removably attachable to the first panel and positioned against the first surface upon attachment to the first panel, wherein a portion of the first connector extends laterally past a first edge of the first surface of the first panel; and
a second module, comprising:
a second panel comprising a second surface; and
a second connector removably attachable to the second panel and positioned against the second surface upon attachment to the second panel, wherein the second connector is aligned with a second edge of the second surface of the second panel, and wherein the second connector defines a cavity, wherein the second module is coupled to the first module in a laterally stacked configuration, wherein the portion of the first connector extending past the first edge of the first panel is positioned within the cavity defined by the second connector, wherein the first surface is aligned with the second surface in the stacked configuration, wherein the first panel comprises a first support member attached to and extending away from the first panel, wherein the first connector further defines a first hole in the first connector, wherein the first support member is slidably receivable into the first hole defined by the first connector during attachment of the first connector to the first panel, and wherein the first panel further comprises:
a second support member attached to and extending away from the first panel, wherein the second support member is offset from the first support member;
wherein the second connector further defines a second hole in the second connector; and
wherein the second connector is slidably attachable to the first panel, wherein the second support member is slidably receivable into the second hole defined by the second connector.

8. A modular energy system, comprising:
a first module, comprising:
a first panel, comprising:
a first support member attached to the panel;
a second support member attached to the panel, wherein the second support member is offset from the first support member;
a support ledge attached to the first panel, wherein the support ledge is located between the first support member and the second support member;
a first connector, defining a first hole in the first connector, the first connector comprising a support rib that extends away from the first connector, wherein the first connector is slidably attachable to the first panel, wherein the first support member is slidably insertable into the first hole, and wherein in an attached configuration, the support rib is configured to rest against the support ledge, and wherein in the attached configuration, a portion of the first connector extends past a first edge of the first panel; and
a second connector defining a cavity and a second hole, wherein the second connector is slidably attachable to the first panel, wherein the second support member is slidably receivable into the second hole, wherein in the attached configuration, the second connector is aligned with a second edge of the first panel, and wherein the second edge of the first panel is opposite the first edge of the first panel.

9. The modular energy system of claim 8, further comprising:
a second module, comprising:
a second panel, comprising:
a third support member attached to the second panel;
a fourth support member attached to the second panel, wherein the fourth support member is offset from the third support member;
a second support ledge attached to the second panel, wherein the support ledge is located between the third support member and the fourth support member;
a third connector defining a third hole in the third connector, wherein the third connector comprises a second support rib that extends away from the third connector, wherein the third connector is slidably attachable to the second panel, wherein the third support member is slidably receivable into the third hole define by the third connector and in the attached configuration, the second support rib is configured to rest against the second support ledge, and wherein in the attached configuration, a second portion of the third connector extends past a third edge of the second panel; and
a fourth connector defining a second cavity and a fourth hole in the fourth connector, wherein the fourth connector is slidably attachable to the second panel, wherein the fourth support member is slidably receivable into the fourth hole defined by the fourth connector, wherein in the attached configuration, the second connector is aligned with a fourth edge of the second panel, and wherein the third edge is opposite the fourth edge.

10. The modular energy system of claim 9, wherein the first module is coupled to the second module in a coupled configuration, and in the coupled configuration the second portion of the third connector that extends past the second panel is positioned within the cavity defined by the second connector.

11. The modular energy system of claim 9, wherein the second module is coupled to the first module in a coupled configuration, and in the coupled configuration the portion of the first connector that extends past the first panel is positioned within the cavity defined by the fourth connector.

12. The modular energy system of claim 9, wherein in a coupled configuration, the first module and the second module are physically and electrically connected.

13. A module for a modular energy system, the module comprising:
a panel, comprising:
a first support member attached to and extending away from the panel;
a second support member attached to and extending away from the panel, wherein the second support member is offset from the first support member;
a first connector defining a first hole in the first connector, wherein the first connector is slidably attachable to the panel, wherein the first support member is slidably receivable into the first hole, and wherein in an attached configuration a portion of the first connector extends past a first edge of the panel; and
a second connector defining a cavity and a second hole, wherein the second connector is slidably attachable to the panel, wherein the second support member is slidably receivable into the second hole, wherein in the attached configuration the second connector is aligned with a second edge of the panel, and wherein the second edge of the panel is opposite the first edge of the panel.

14. The module of claim 13, wherein the panel further comprises a support ledge attached to the panel, wherein the support ledge is located between the first support member and the second support member, and wherein the first connector further comprises a support rib that extends away from the first connector, wherein in the attached configuration the support rib rests against the support ledge.

15. The module of claim 13, wherein the module is one of a plurality of modules and the plurality of modules are stackable by inserting the portion of a first connector that extends past one module inside the cavity defined by a second connector of another module, wherein in a stacked configuration, the plurality of modules are physically and electrically connected.

* * * * *